United States Patent
Kesimer

(10) Patent No.: US 12,078,640 B2
(45) Date of Patent: Sep. 3, 2024

(54) METHODS FOR DIAGNOSING OR PREDICTING CHRONIC BRONCHITIS

(71) Applicant: The University of North Carolina at Chapel Hill, Chapel Hill, NC (US)

(72) Inventor: Mehmet Kesimer, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1339 days.

(21) Appl. No.: 16/609,282

(22) PCT Filed: May 3, 2018

(86) PCT No.: PCT/US2018/030820
§ 371 (c)(1),
(2) Date: Oct. 29, 2019

(87) PCT Pub. No.: WO2018/204598
PCT Pub. Date: Nov. 8, 2018

(65) Prior Publication Data
US 2020/0191802 A1 Jun. 18, 2020

Related U.S. Application Data

(60) Provisional application No. 62/500,781, filed on May 3, 2017.

(51) Int. Cl.
*G01N 33/68* (2006.01)
*G16B 5/00* (2019.01)

(52) U.S. Cl.
CPC .......... *G01N 33/6893* (2013.01); *G16B 5/00* (2019.02); *G01N 2333/4725* (2013.01); *G01N 2800/00* (2013.01); *G01N 2800/122* (2013.01); *G01N 2800/127* (2013.01); *G01N 2800/50* (2013.01); *G01N 2800/52* (2013.01); *G01N 2800/60* (2013.01)

(58) Field of Classification Search
USPC .......................................................... 702/19
See application file for complete search history.

(56) References Cited

PUBLICATIONS

Kim, Young S., and Samuel B. Ho. "Intestinal goblet cells and mucins in health and disease: recent insights and progress." Current gastroenterology reports 12 (2010): 319-330. (Year: 2010).*

Britto, Clemente J., and Lauren Cohn. "Bactericidal/permeability-increasing protein fold-containing family member A1 in airway host protection and respiratory disease." American journal of respiratory cell and molecular biology 52.5 (2015): 525-534. (Year: 2015).*

Thornton, David J., and John K. Sheehan. "From mucins to mucus: toward a more coherent understanding of this essential barrier." Proceedings of the American Thoracic Society 1.1 (2004): 54-61. (Year: 2004).*

International Search Report and Written Opinion corresponding to International Patent Application No. PCT/US2018/030820, mailed Sep. 6, 2018, 10 pages.

Henderson et al. "Cystic fibrosis airway secretions exhibit mucin hyperconcentration and increased osmotic pressure" J Clin Invest., 124(7):3047-60 (2014).

Kim V. et al. "Chronic bronchitis and chronic obstructive pulmonary disease" American Journal of Respiratory and Critical Care Medicine, 187(3):228-237 (2012).

Rademacher et al. "Bronchlectasis—Diagnosis and Treatment" Deutsches Aerzteblatt Online, 108(48):809-816 (2011).

Redding et al. "Physical and transport properties of sputum from children with idiopathic bronchiectasis" Chest, 134 (6): 1129-1134 (2008).

Notification and International Preliminary Report on Patentability corresponding to International Application No. PCT/US2018/030820, dated Nov. 5, 2019, 9 pages.

* cited by examiner

*Primary Examiner* — Lori A. Clow
(74) *Attorney, Agent, or Firm* — Myers Bigel, P.A.

(57) ABSTRACT

The present invention is directed to the use of (1) mucin concentration in sputum; (2) individual airway mucins MUC5AC and MUC5B ratio (MUC5AC/MUC5B) in sputum; and (3) combination of both measurements (Kesimer MUCQuant index) that can be used as an objective biomarker for differential diagnosis of smoking status and chronic bronchitis (CB), disease severity of CB (mild, moderate, and severe), exacerbation status, monitoring progression of CB, and guiding of therapies for CB. In addition, the ratio of amount of IgGFc-binding protein (FCGBP) and the amount of bactericidal/permeability-increasing fold-containing family member A1 (BPIFA1 (or SPLUNC1)) present in a sputum sample from a subject may be used in combination with the Kesimer MUCQuant index (Kesimer MUCQuant Plus index) for differential diagnosis of smoking status and CB, disease severity of CB, exacerbation status, p monitoring progression of CB, and guiding of therapies for CB.

11 Claims, 24 Drawing Sheets

Smoking History Asthma (-)

METHODS FOR DIAGNOSING OR PREDICTING CHRONIC BRONCHITIS

PRIORITY

This application is a 35 U.S.C. § 371 national phase application of International Application Serial No. PCT/US2018/030820; Filed: May 3, 2018, which claims the benefit, under 35 U.S.C. § 119 (e), of U.S. Provisional Application No. 62/500,781, filed on May 3, 2017, the entire contents of each of which is incorporated by reference herein.

STATEMENT OF FEDERAL SUPPORT

This invention was made with government support under grant number HL110906 awarded by National Institutes of Health. The government has certain rights to this invention.

FIELD OF THE INVENTION

The present invention relates to methods for diagnosing or identifying a risk of developing chronic bronchitis using airway mucin concentrations.

BACKGROUND OF THE INVENTION

Human airway surfaces are protected from the noxious effects of inhaled insults by a mucus clearance system that traps deposited materials and clears them from the lung. Mucins are the major macromolecules in mucus gel which covers and protects our epithelial surfaces from biological, chemical and physical insults. Mucins are considered as the major gel-forming components of mucus and vital for normal respiratory tract function. The secreted mucins, and in particular the polymeric mucins, MUC5AC and MUC5B, hydrate, lubricate and provide the organizing framework of the airways mucus gel and are major contributors to mucus rheological properties such as viscosity and elasticity. They are produced and released at low levels in the health airways to keep the airways sterile. However, in hypersecretory diseases, such as cystic fibrosis, chronic bronchitis and asthma, these molecules are overproduced leading to impaired rheology that cause poor clearance, impaired gas exchange, bacterial colonization and infection, and lung damage.

Chronic bronchitis affects about 15 million individuals in the United States and is characterized by mucus accumulation in the airways and metaplasia of mucus/mucin secreting goblet cells. Progress has been made in identifying and quantitating emphysema based on CT scanning/scoring. However, the diagnosis of chronic bronchitis, also known as chronic mucus hypersecretion, relies on self-report symptom scores, including the classic and the St. George's Respiratory Questionnaires (SGRQ). Symptoms defined by these questionnaires correlate with duration of cigarette smoking, exacerbation frequency, and FEV1. As yet, there is no objective biomarker to complement self-reporting for the diagnosis of chronic bronchitis.

SUMMARY OF THE INVENTION

One aspect of the present invention relates to a method of diagnosing or identifying a risk of developing chronic bronchitis (CB) in a subject, comprising: measuring the amount of mucin present in a sputum sample from the subject; and diagnosing the subject as having CB or identifying the subject as being at risk of developing CB when the amount of mucin is increased as compared to an amount of mucin measured in a control sputum sample.

Another aspect of the present invention relates to a method of diagnosing or identifying a risk of developing chronic bronchitis (CB) in a subject, comprising: measuring the amount of mucin 5AC (MUC5AC) and/or the amount of mucin 5B (MUC5B) present in a sputum sample from the subject; and diagnosing the subject as having CB or identifying the subject as being at risk of developing CB when the measured amount of MUC5AC in the sputum sample from the subject is increased as compared to an amount of MUC5AC measured in a control sputum sample and/or when the measured amount of MUC5B in the sputum sample from the subject is increased as compared to the amount of MUC5B measured in a control sputum sample.

A further aspect of the present invention relates to a method of diagnosing or identifying a risk of developing chronic bronchitis (CB) in a subject, comprising: measuring the amount of each of (a) mucin, (b) mucin 5AC (MUC5AC) and (c) mucin 5B(MUC5B) in a sputum sample from the subject; calculating a ratio of the measured amount of MUC5AC to the measured amount of MUC5B; calculating a Kesimer MUCQuant index (KMQuant index) by multiplying the ratio by the measured amount of mucin to provide a product and dividing the product by 100 (i.e., mucin× (MUC5AC÷MUC5B))÷100); and diagnosing the subject as having CB or identifying the subject as being at risk of developing CB when the KMQuant index calculated for the sputum sample from the subject is increased as compared to a KMQuant index calculated for a control sputum sample. In some embodiments, the method of diagnosing or identifying a risk of developing chronic bronchitis (CB) in a subject further comprises measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; and calculating a KMQuant plus (+) index (MUCQuant+ index) by multiplying the ratio of the measured amount of FCGBP to the measured amount of SPLUNC1 by the KMQuant index ([mucin]×([MUC5AC]÷[MUC5B])÷100× (FCGBP÷SPLUNC1)), wherein the subject is diagnosed as having CB has a KMQuant+ index that is increase by about 250-fold to about 350-fold as compared to a KMQuant+ index calculated for the control sputum sample or the subject is identified as being at risk of developing CB has a KMQuant+ index that is increased by about 10-fold to about 20-fold over a KMQuant+ index calculated for the control sputum sample.

An additional aspect of the invention relates to a method of diagnosing or identifying a risk of developing chronic bronchitis (CB) in a subject, comprising: measuring the amount of each of (a) mucin 5AC (MUC5AC) and (b) mucin 5B(MUC5B) present in a sputum sample from the subject; calculating a ratio of the measured amount of MUC5AC to the measured amount of MUC5B; diagnosing the subject as having CB or identifying the subject as being at risk of developing CB when the ratio is increased as compared to a ratio of a measured amount of MUC5AC to a measured amount of MUC5 for a control sputum sample.

Another aspect of the invention relates to a method of diagnosing CB or both CB and emphysema in a subject having chronic obstructive pulmonary disease (COPD), comprising: measuring the amount of mucin present in a sputum sample from the subject; and diagnosing the subject as having CB when the amount of mucin in the sputum sample is about 2 times an amount of mucin measured in a control sputum sample or diagnosing the subject as having CB and emphysema when the amount of mucin in the sputum sample is about 3 times the amount of mucin measured in a control sputum sample.

A further aspect relates to a method of diagnosing CB or both CB and emphysema in a subject having chronic obstructive pulmonary disease (COPD), comprising: measuring the amount of mucin 5AC (MUC5AC) present in a sputum sample from the subject; and diagnosing the subject as having CB when the measured amount of MUC5AC in the sputum sample is increased as compared to an amount of MUC5AC measured in a control sputum sample or diagnosing the subject as having CB and emphysema when the measured amount of MUC5AC in the sputum sample is increased as compared to the amount of MUC5AC measured in a sputum sample from a subject having CB only.

An additional aspect of the invention relates to a method of diagnosing CB or both CB and emphysema in a subject having chronic obstructive pulmonary disease (COPD), comprising: measuring the amount of each of (a) mucin, (b) mucin 5AC (MUC5AC) and (c) mucin 5B(MUC5B) present in a sputum sample from the subject; calculating a ratio of the measured amount of MUC5AC to the measured amount of MUC5B; calculating a KMQuant index by multiplying the ratio by the measured amount of mucin to provide a product and dividing the product by 100; and diagnosing the subject as having CB when the KMQuant index is increased as compared to a KMQuant index calculated for a control sputum sample or diagnosing the subject as having CB and emphysema when the KMQuant index is increased as compared to a KMQuant index of a subject having CB only. In some embodiments, the method of diagnosing CB or both CB and emphysema in a subject having chronic obstructive pulmonary disease (COPD), further comprises measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; calculating a KMQuant plus (+) index (MUCQuant+ index) by multiplying the ratio of the measured amount of FCGBP to the measured amount of SPLUNC1 by the KMQuant index; and diagnosing the subject as having CB when the KMQuant+ index calculated for the sputum sample from the subject is increase by about 250-fold to about 350-fold as compared to a KMQuant+ index calculated for the control sputum sample or identifying the subject as being at risk of developing CB when the KMQuant+ index calculated for the sputum sample from the subject is increased by about 10-fold to about 20-fold over a KMQuant+ index calculated for the control sputum sample.

Another aspect of the invention relates to a method for diagnosing an exacerbation of chronic obstructive pulmonary disease (COPD) in a subject diagnosed with COPD, comprising: a) measuring a first amount of mucin present in a first sputum sample taken from the subject at a first time point; b) measuring a second amount of mucin in a second sputum sample taken from the subject at a second time point subsequent to the first time point; and c) comparing the first amount of mucin in the first sputum sample to the second amount of mucin from the second sample, wherein an increase in the amount of mucin between the first sputum sample and the second sputum sample diagnoses an exacerbation of COPD.

A further aspect of the invention relates to a method for diagnosing an exacerbation of chronic obstructive pulmonary disease (COPD) in a subject diagnosed with COPD, comprising: a) measuring a first amount of each of (i) mucin, (ii) mucin 5AC (MUC5AC) and (iii) mucin 5B(MUC5B) in a first sputum sample taken from the subject at a first time point; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring a second amount of each of (i) mucin, (ii) MUC5AC and (iii) MUC5B in a second sputum sample taken from the subject at a second time point subsequent to the first time point; e) calculating a second KMQuant index for the second sputum sample by multiplying the second ratio by the measured amount of mucin from the second sputum sample to provide a product and dividing the product by 100; and f) comparing the first KMQuant index calculated for the first sample (c) to the second KMQuant index calculated for the second sample (e), wherein an increase in the KMQuant index between the first sputum sample and the second sputum sample diagnoses an exacerbation of COPD. In some embodiments, method for diagnosing an exacerbation of chronic obstructive pulmonary disease (COPD) in a subject diagnosed with COPD-further comprises h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a KMQuant plus (+) index for the first sputum sample by multiplying the ratio of the measured amount of FCGBP to the measured amount of SPLUNC1 by the KMQuant index, k) measuring the amount of each of an IgGFc-binding protein (FCGBP) and a bactericidal/permeability-increasing fold-containing family member A1 (BPIFA1 (or SPLUNC1)) present in the second sputum sample from the subject; l) calculating a ratio of the measured amount of FCGBP to the measured amount of SPLUNC1 in the second sputum sample; m) calculating a KMQuant+ index for the second sputum sample by multiplying the ratio of the measured amount of FCGBP to the measured amount of SPLUNC1 by the KMQuant index+; and n) comparing the KMQuant+ index calculated for the first sample (j) to the KMQuant+ index calculated for the second sputum sample (m), wherein an increase in the KMQuan+ index calculated for the second sputum sample as compared to the KMQuant+ index calculated for the first sputum diagnoses an exacerbation of COPD in the subject.

An additional aspect of the invention provides a method of assessing the effectiveness of a treatment for CB in a subject, comprising: a) measuring a first amount of each of mucin and/or mucin 5AC (MUC5AC) present in a first sputum sample taken from the subject at a time prior to treatment for CB or at a defined first time point during treatment of the subject for CB; b) measuring a second amount of each of mucin and/or MUC5AC in a second sputum sample taken from the subject at a second time point subsequent to the first time point or at a second time point during treatment of the subject for CB; and c) comparing the first amount of mucin from the first sputum sample (a) to the second amount of mucin from the second sputum sample (b), wherein a change in the amount of mucin between the first sputum sample and the second sputum sample assesses the effectiveness of the treatment and/or comparing the first amount of MUC5AC from the first sputum sample (a) to the second amount of MUC5AC from the second sputum sample (b), wherein a change in the amount of MUC5AC between the first and the second sample assesses the effectiveness of the treatment.

A further aspect of the invention relates to a method of assessing the effectiveness of a treatment for CB in a subject, comprising: a) measuring a first amount of each of (i) mucin, (ii) mucin 5AC (MUC5AC), and (iii) mucin 5B(MUC5B) in a first sputum sample taken from the subject at a time point prior to treatment for CB or at a first time point during treatment for CB; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring a second amount of each of (i) mucin, (ii) MUC5AC and (iii) MUC5B in a second sputum sample taken from the subject at a second time point subsequent to the first time point or at a second time point during treatment for CB; e) calculating a second ratio of the measured amount of MUC5AC to the measured amount of MUC5B from the second sputum sample; f) calculating a second KMQuant index for the second sputum sample by multiplying the second ratio by the measured amount of mucin from the second sputum sample to provide a product and dividing the product by 100; and g) comparing the first KMQuant index from the first sputum sample (c) to the second KMQuant index from the second sample (f), wherein a change in the KMQuant index between the first sputum sample and the second sputum sample assesses the effectiveness of the treatment. In some embodiments, the method of assessing the effectiveness of a treatment for CB in a subject, further comprises h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a KMQuant plus (+) index for the first sputum sample by multiplying the ratio of the measured amount of FCGBP to the measured amount of SPLUNC1 by the KMQuant index; k) measuring the amount of each of FCGBP and SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and (n) comparing the KMQuant+ index from the first sputum sample (j) to the KMQuant+ index from the second sputum sample (m), wherein an increase or no change in the KMQuant+ index calculated for the second sputum sample as compared to the KMQuant+ index calculated for the first sample indicates that the treatment is not effective, and a decrease in the KMQuant+ index calculated for the second sputum sample as compared to the KMQuant+ index calculated for the first sample indicates that the treatment is effective.

An additional aspect of the invention relates to a method of monitoring the progression of CB or a risk of developing CB in a subject, comprising: a) measuring a first amount of each of (i) mucin, (ii) mucin 5AC (MUC5AC), and (iii) mucin 5B(MUC5B) in a first sputum sample taken from the subject at a first time point; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring a second amount of each of (i) mucin, (ii) MUC5AC and (iii) MUC5B in a second sputum sample taken from the subject at a second time point subsequent to the first time point; e) calculating a second ratio of the measured amount of MUC5AC to the measured amount of MUC5B from the second sputum sample; f) calculating a second KMQuant index for the second sputum sample by multiplying the second ratio of by the measured amount of mucin from the second sputum sample to provide a product and dividing the product by 100; and g) comparing the first KMQuant index from the first sample (c) to the second KMQuant index from the second sample (f), wherein a change in the KMQuant index between the first sputum sample and the second sputum sample shows progression of CB in the subject or an increased risk of developing CB.

In some embodiments, the a method of monitoring the progression of CB or a risk of developing CB in a subject further comprises h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a KMQuant+ index for the first sputum sample by multiplying the ratio of the measured amount of FCGBP to the measured amount of SPLUNC1 by the KMQuant index); k) measuring the amount of each of an FCGBP and a SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and n) comparing the KMQuant+ index from the first sputum sample (j) to the KMQuant+ index from the second sputum sample (m), wherein an increase in the KMQuant+ index calculated for the second sputum sample as compared to the KMQuant+ index calculated for the first sample indicates that CB in the subject is progressing, and a decrease in the KMQuant+ index calculated for the second sputum sample as compared to the KMQuant+ index calculated for the first sample indicates that CB in the subject is stable or improving.

A further aspect of the invention relates to a method of diagnosing asthma and/or asthma severity, comprising: measuring the amount of each of (a) mucin, (b) the amount of mucin 5AC (MUC5AC), and (c) the amount mucin 5B(MUC5B) present in a sputum sample from the subject; calculating a ratio of the measured amount of MUC5AC to the measured amount of MUC5B from the sputum sample; calculating a KMQuant index by multiplying the ratio of the measured amount of MUC5AC to the measured amount of MUC5B by the measured amount mucin to provide a product and dividing the product by 100; and diagnosing the subject as having mild or moderate asthma when the KMQuant index is at least about 20 fold higher than a KMQuant index calculated for a control sputum sample, or as having severe asthma when the KMQuant index is about 100 fold higher than a KMQuant index calculated for a control sputum sample. In some embodiments, the method of diagnosing asthma and/or asthma severity further comprises measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; calculating a MUCQuant plus (+) index (KMQuant+ index) by multiplying the ratio of the measured amount of FCGBP to the measured amount of SPLUNC1 by the Kesimer MUCQuant index (KMQuant index), and diagnosing the subject as having mild or moderate asthma when the KMQuant+ index calculated for the sputum sample is at least about 350 fold higher than a KMQuant+ index calculated for a control sputum sample, or as having severe asthma when the KMQuant+ index calculated for the sputum sample is about 6500 fold higher than a KMQuant+ index calculated for a control sputum sample.

An additional aspect of the invention provides a method of guiding treatment of a subject diagnosed with COPD, comprising: a) measuring an amount of each of (i) mucin, (ii) mucin 5AC (MUC5AC) and (iii) mucin 5B(MUC5B) in a first sputum sample taken from the subject at a first time point; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) total mucin, (ii) MUC5AC and (iii) MUC5B in a second sputum sample taken from the subject at a subsequent time point (e.g., subsequent to the first time point); e) calculating a second ratio of the measured amount of MUC5AC to the measured amount of MUC5B from the second sputum sample; f) calculating a second KMQuant index for the second sputum sample by multiplying the second ratio by the measured amount of mucin from the second sputum sample to provide a product and dividing the product by 100; and g) comparing the first KMQuant index calculated for the first sample (c) to the second KMQuant index calculated for the second sputum sample (f), wherein an increase in the KMQuant index calculated for the second sputum sample as compared to the KMQuant index calculated for the first sputum sample indicates that the treatment is not effective and the treatment is discontinued or changed, and a decrease in the KMQuant index calculated for the second sputum sample as compared to the KMQuant index calculated for the first sputum sample indicates that the treatment is effective and the treatment is continued. In some embodiments, the method of guiding treatment of a subject diagnosed with COPD may further comprise measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a MUCQuant plus (+) index (KMQuant+ index) for the first sputum sample by multiplying the ratio of the measured amount of FCGBP to the measured amount of SPLUNC1 by the Kesimer MUCQuant index (KMQuant index); k) measuring the amount of each of an FCGBP and a SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and n) comparing the first KMQuant+ index from the first sputum sample (j) to the second KMQuant+ index from the second sputum sample (m), wherein an increase in the KMQuant+ index calculated for the second sputum sample as compared to the KMQuant+ index calculated for the first sputum sample indicates that the treatment is not effective and the treatment is discontinued or changed, and a decrease in the KMQuant+ index calculated for the second sputum sample as compared to the KMQuant+index calculated for the first sputum sample indicates that the treatment is effective and the treatment is continued.

In a further aspect, the invention provides a method of guiding treatment of a subject diagnosed with CB, the method comprising: a) measuring an amount of each of mucin and/or mucin 5AC (MUC5AC) present in a first sputum sample taken from the subject at first time point prior to treatment for CB or during treatment of the subject for CB; b) measuring an amount of each of mucin and/or MUC5AC in a second sputum sample taken from the subject at a subsequent time point (e.g. subsequent to the first time point) during treatment of the subject for CB; and c) comparing the amount of mucin from the first sputum sample (a) to the amount of mucin from the second sputum sample (b), wherein an increase or no change in the amount of mucin or in the amount of MUC5AC in the second sputum sample as compared to the amount of mucin or the amount of MUC5AC in the first sputum sample indicates that the treatment is not effective and the treatment is discontinued or changed, and a decrease in the amount of mucin or in the amount of MUC5AC in the second sputum sample as compared to the amount of mucin or the amount of MUC5AC in the first sputum sample indicates that the treatment is effective and the treatment is continued. In some embodiments, the In an additional aspect, a method of guiding treatment of a subject diagnosed with CB is provided, the method comprising: a) measuring an amount of each of (i) mucin, (ii) mucin 5AC (MUC5AC), and (iii) mucin 5B(MUC5B) in a first sputum sample taken from the subject at a first time point prior to treatment for CB or during treatment for CB; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) mucin, (ii) MUC5AC and (iii) MUC5B in a second sputum sample taken from the subject at a subsequent time point (e.g., subsequent to the first time point) during treatment of the subject for CB; e) calculating a second ratio of the measured amount of MUC5AC to the measured amount of MUC5B in the second sputum sample; f) calculating a second KMQuant index for the second sputum sample by multiplying the second ratio by the measured amount of mucin from the second sputum sample to provide a product and dividing the product by 100; and g) comparing the first KMQuant index from the first sputum sample (c) to the second KMQuant index from the second sputum sample (f), wherein an increase or no change in the KMQuant index calculated for the first sample as compared to the KMQuant index calculated for the second sputum sample indicates that the treatment is not effective and the treatment is discontinued or changed, and a decrease in the KMQuant index calculated for the first sample as compared to the KMQuant index calculated for the second sputum sample indicates that the treatment is effective and the treatment is continued. In some embodiments, the method of guiding treatment of a subject diagnosed with CB may further comprise h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a MUCQuant plus (+) index (KMQuant+ index) for the first sputum sample by multiplying the ratio of the measured amount of FCGBP to the measured amount of SPLUNC1 by the Kesimer MUCQuant index (KMQuant index), k) measuring the amount of each of an FCGBP and a SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and comparing the first KMQuant+ index from the first sputum sample (j) to the second KMQuant+ index from the second sputum sample (m), wherein an increase in the KMQuant+ index calculated for the second sputum sample as compared to the KMQuant+ index calculated for the first sputum sample indicates that the treatment is not effective and the treatment is discontinued or changed, and a decrease in the KMQuant+ index calculated for the second sputum sample as compared to the KMQuant+ index calculated for the first sputum sample indicates that the treatment is effective and the treatment is continued.

These and other aspects of the present invention are explained in more detail in the description of the invention below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 1A shows a model representing the progression from health to cigarette smoke (CS)-induced Chronic Bronchitis (CB). In health, (far left panel), the balance of active ion absorption ($Na^+$) vs. secretion ($Cl^-$), passive osmotically enhanced water transport, and mucin secretion generates a mucus layer with secreted mucin concentrations lower than the tethered mucins and other glycoconjugate concentration in the periciliary layer (PCL). The result is a well hydrated PCL and efficient mucociliary (MCC) transport. With CB disease/CS exposure, an imbalance of ion transport coupled to mucin hypersecretion increases the mucus layer mucin concentration [mucin]. These events produce osmotic compression of the PCL, adhesion of hyper-concentrated mucus to airway surfaces, and cessation of MCC. The adherent mucus may be expelled as phlegm/sputum by cough (upper right panel). Mucus that cannot be expelled by cough continues to accumulate, concentrates, and ultimately becomes the basis for airflow obstruction and the nidus for intermittent infection (bottom right panel). Several aspects of this model were evaluated in SPIROMICS. FIG. 1B shows mean mucin concentration in never smoker control subjects with no phlegm (N=59), ever-smokers who reported no phlegm (N=397), and ever-smokers who reported bringing up phlegm (N=434). FIG. 1C shows mean mucin concentration in mucoid (N=364) compared to watery sputum (N=350) in ever-smokers. Mucoid and watery were pre-defined by SPIROMICS clinical site technologists at the time of sputum induction. FIG. 1D shows the relationship between technologist-reported mucus plugs and mean mucin concentration in ever-smokers with sparse plugs (N=313), moderate plugs (N-225), and numerous plugs (N=110). The dashed lines in FIGS. 1C and 1D depict the mean concentration of never-smokers (1515 μg/mL). T bars indicate SEM. *P=0.05-0.01, P=0.001-0.0099, *P=0.0001-0.00099, ****P<0.0001. Significance values shown but not connected via a bracket compare the significance of the designated group to the first group shown. Other significant differences between groups are shown with a bracket. All P values are adjusted for multiple comparisons using the Tukey-Kramer method.

FIG. 2A shows mean mucin concentrations with spirometrically-defined disease severity (Control-never-smokers; N=69), GOLD 0 (ever-smokers with no COPD, FEV1/FVC>0.7, N=303), and GOLD 1 (ever-smokers with mild COPD; N=165), GOLD 2 (ever-smokers with moderate COPD; N=293) and GOLD 3 (ever-smokers with severe COPD; N=85). Table 1 defines COPD status. FIG. 2B shows mean mucin concentration versus total prospective annualized exacerbation rate from enrollment to end of study (end of study defined as number of days till follow-up, or death) in Strata 1-4. Rates were classified as zero (N=596), 0<but<2 (N=262) and 2+(N=36) exacerbations/year. FIG. 2C shows mucin concentration and smoking history. (Never-smokers; N=69), past smokers (ever-smokers not currently smoking; N=460) and current smokers (N=374). FIG. 2D shows the mucin concentration in COPD participants (GOLD stages 1-3) with current asthma (N=84) and COPD participants never diagnosed with asthma (N=389). *P=0.05-0.01, P=0.001-0.0099, *P=0.0001-0.00099, ****P<0.0001. T bars indicate SEM. All P values are adjusted for multiple comparisons using the Tukey-Kramer method. Significance values shown but not connected via a bracket compare the participant group with significance to the first group shown. Other significant differences between groups are shown with a bracket.

FIGS. 3A and 3B show mean MUC5B and MUC5AC concentrations, respectively, in control (never-smokers; MUC5B N=19 and MUC5AC N=18), ever-smokers without spirometric evidence of COPD (N=42), ever smokers with Mild/Moderate COPD (N=59) and ever-smokers with severe COPD (N=28). FIG. 3C shows the MUC5AC/MUC5B ratio for the same groups (N as in (B)). FIG. 3D shows the MUC5AC/MUC5B ratio in never-smokers (N=18), past ever-smokers (N=73), and current smokers (N=56). *P=0.05-0.01, P=0.001-0.0099, *P=0.0001-0.00099, ****P<0.0001. T bars indicate SEM. All P values are adjusted for multiple comparisons using the Tukey-Kramer method. Significance values shown but not connected via a bracket compare the participant group with significance to the first group shown. Other significant differences between groups are shown with a bracket.

FIG. 4A shows mean mucin concentrations for ever-smoker participants who completed CB questionnaires. Total mean mucin concentrations are shown for Classic-defined CB (N=199), SGRQ-defined CB (N=382) and control (never-smokers identified with no CB by either questionnaire, N=58). FIG. 4B and FIG. 4C show mean MUC5B and MUC5AC concentration, respectively, for participants who completed CB Classic or SGRQ questionnaires. Total mean MUC5B and MUC5AC concentrations are shown for Classic-defined CB (N=50), SGRQ-defined CB (N=73) and control (never-smokers identified with no CB by either questionnaire, N=18 for MUC5B; N=17 for MUC5AC). FIG. 4D shows mean mucin concentrations in ever-smokers with CB (using the Classic-defined CB) without emphysema (CB+/Em−; N=127), with CB plus emphysema (CB+/Em+; N=66), with no CB and no emphysema (CB−/Em−; N-431), and with no CB but with emphysema (CB−/Em+; N=182). FIG. S8 shows the same analysis using SGRQ-defined CB. FIG. 4E shows mucin concentration relationship to GOLD stage 0 with and without symptoms, as defined by the COPD Assessment Test (CAT) score of <10 or ≥10, respectively. Analysis shows mucin concentration for smokers in GOLD Stage 0 without symptoms (GOLD0-S, FEV1/FVC>0.7 and CAT score<10, N=143) and smokers in GOLD Stage 0 with symptoms (GOLD0+S, FEV1/FVC>0.7 with CAT score≥10, N=131). Mucin concentrations were elevated in smokers with symptoms compared to smokers without symptoms (*P value=0.0291). FIG. 4F shows receiver-operating-characteristics curves for mucin concentration in CB positive subjects diagnosed with the classic questionnaire, compared to the never-smoker controls, in the SPIROMICS cohort (second from the top, area under the curve=0.722 [0.6534 to 0.7905]) and in the independent study (Top curve, AUC=0.822 [0.7252 to 0.9201]). The third ROC curve shows mucin concentration in CB positive subjects diagnosed with the classic questionnaire, compared to all non-CB subjects in the SPIROMICS cohort (blue, AUC=0.6234 [0.5802 to 0.6666]). *P=0.05-0.01, P=0.001-0.0099, *P=0.0001-0.00099, ***P<0.0001. T bars indicate SEM. All P values are adjusted for multiple comparisons using the Tukey-Kramer method. Significance values shown but not connected via a bracket compare the participant group with significance to the first group shown. Other significant differences between groups are shown with a bracket.

FIG. 7A shows MUC5AC is higher in current (N=56) smoker (P value=0.0003) compared to never-smoker (N=18), and past smoker (N=73) were also significantly higher compared to never-smoker (P value=0.0292). FIG. 7B shows MUC5AC/5B ratio and smoking history with the current asthma phenotype removed. Even with asthma removed from this cohort, a current history (N=42) of smoking was associated with a significantly higher MUC5AC/MUC5B ratio compared to never smokers (N=18, P value=0.0009) and past smokers (N=62, P value=0.0026). FIG. 7C shows MUC5AC concentration and self-report of current asthma in Strata 2-4 (defined as past and current smokers with a history of >20 pack-years, with and without airflow obstruction). Participants who reported current asthma (N=20) did not have significantly elevated MUC5AC concentrations (P value=0.6714) when compared to participants that were never diagnosed with asthma (N=100). Participants who reported childhood asthma (N=10) did not have elevated MUC5AC concentrations (P value=0.1911) when compared to participants that were never diagnosed with asthma (N=100, graph not shown).

FIG. 8A shows participants diagnosed with CB using the St. George Questionnaire in Strata 2-4. Participants with diagnosis of both CB and EMPH (N=118) and participants with CB only (N=255) exhibited higher mucin concentrations than participants with no CB and no EMPH (N=298) (**P value<0.0001). Participants with a diagnosis of both CB and EMPH have higher mucin concentration than participants with EMPH only (N=133), P value=0.0073. FIG. 8B is a tukey boxplot representation of panel A.

FIG. 10A shows a ROC curve describing how mucin concentration relates to CB diagnosed by Classic CB in the entire population. While mucin concentration is very significantly associated with Classic CB, the area under the curve=0.6234, P Value=<0.0001. FIG. 10B shows a ROC curve describing how mucin concentration relates to CB diagnosed by SGRQ in the entire population. While mucin concentration is very significantly associated with SGRQ CB, the area under the curve=0.6323, P Value=<0.0001. FIG. 10C shows that the sputum neutrophil count/L was not associated with Classic CB, the area under the curve=0.5072, P value=0.9624. FIG. 10D shows that the sputum neutrophil count/L was not associated with SGRQ CB, the area under the curve=0.5228, P value=0.4260.

FIG. 17A shows mean MUCQ score for never smokers (control, N=19), smokers with no airway disease (N=41), with CB (N=51) and non-CF bronchiectasis (N=29). FIG. 17B shows ROC curves for the MUCQ Plus score for CB. (Second from the top, AUC=0.987) and for non-CF bronchiectasis (Top, AUC=1.000) and smokers with no disease (Third from the top, AUC=0.811) compared to healthy controls. *$P=0.05$-0.01, $P=0.001$-0.0099, *$P=0.0001$-0.00099, ****$P<0.0001$.

DETAILED DESCRIPTION

Figure 1A:
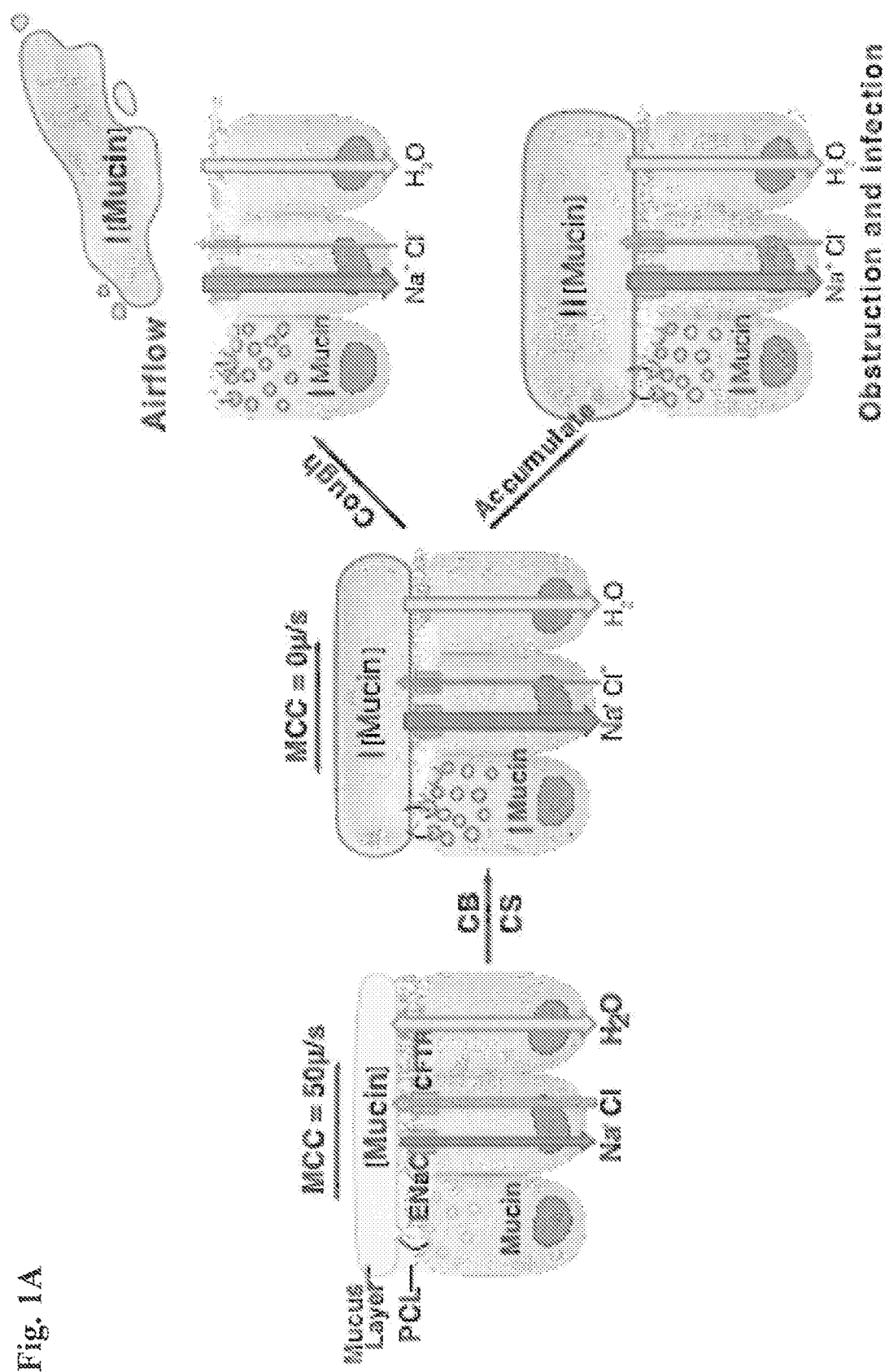
FIGS. 1A-1D are graphs showing the relationship of mucin concentrations with phlegm production, consistency, and mucus plug formation.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein "increase" or "enhance," and grammatical variations thereof, describe an elevation of at least about 10%, 15%, 20%, 25%, 50%, 75%, 100%, 150%, 200%, 300%, 400%, 500% or more as compared to a control.

The term "inhibit" or "reduce" or grammatical variations thereof as used herein refer to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

As used herein, "a subsequent time point" can mean any time point subsequent to a prior time point, e.g., subsequent to a first time point.

An "effective" amount as used herein is an amount that provides a desired effect.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment," it is intended that the severity of the subject's condition is reduced or at least partially improved or modified and that some alleviation, mitigation or decrease in at least one clinical symptom is achieved.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

A "subject" of the invention may be any animal. In some embodiments, it may be any animal that has or is suspected of having chronic bronchitis (CB) or chronic obstructive pulmonary disease (COPD). Such a subject is generally a mammalian subject (e.g., a laboratory animal such as a rat, mouse, guinea pig, rabbit, primate, etc.), a farm or commercial animal (e.g., a cow, horse, goat, donkey, sheep, etc.), or a domestic animal (e.g., cat, dog, ferret, etc.). In some embodiments, the subject is a primate subject, a non-human primate subject (e.g., a chimpanzee, baboon, monkey, gorilla, etc.) or a human. In some embodiments, a subject of the invention can be a subject known to have or believed to have CB. In some embodiments, a subject of the invention can be a subject known or believed to be at risk of developing CB. Alternatively, a subject according to the invention can also include a subject not previously known or suspected to have CB. In some embodiments of the invention, the subject is a current smoker or has been a smoker in the past (i.e., past smoker). Subjects include males and/or females. Subjects can be of any age, but generally are mature and/or geriatric subjects. In some embodiments, a subject may be a current or a past smoker.

In some embodiments, the term "mucin" may refer to all gel forming mucins present in a sputum sample and includes, but is not limited to, mucin 5B (MUC5B) and mucin 5AC. In other embodiments, "mucin" may refer to only MUC5B and MUC5AC. MUC5B and MUC5AC are the major gel forming mucins present in a sputum sample. Thus, in some embodiments, "measuring an amount of mucin" may comprise measuring all gel forming mucins present in the sputum sample.

A number of pulmonary diseases, including chronic obstructive lung disease (COPD), exhibit a failure of the mucus clearance system with intra-pulmonary mucus accumulation. COPD is characterized by chronic bronchitis and emphysematous components. Pulmonary mucus accumulation contributes to the symptoms of sputum/phlegm production, airflow obstruction, and the exacerbations associated with the chronic bronchitis component of COPD.

The mucus that forms a protective barrier on airway surfaces is composed of ions, water (about 98%), globular proteins, and polymeric mucin macromolecules. The high molecular weight ($>10^7$ Da) mucin polymers, predominantly MUC5B and MUC5AC, provide the biophysical properties required for airway mucus transport and generate the perception of mucus as a "gel." A recent biophysical model (the "two gel hypothesis") posits that respiratory mucin concentrations govern mucus transport rates in the lung (Button et al. Science 337:937-41 (2012)) (FIG. 1A). This model predicts that as mucin concentrations rise, a threshold concentration is exceeded, after which mucus transport slows/ceases, and adherent mucus plaques form on airway surfaces. Ultimately, some accumulated mucus may be expectorated as sputum/phlegm. However, accumulated mucus that cannot be expectorated serves as the nidus for airflow obstruction, inflammation, and intermittent infection.

The present inventor has surprisingly discovered that mucin levels alone and in combination with individual mucin levels (e.g., mucin 5AC (MUC5AC) and mucin 5B (MUC5B)) as measured in sputum samples can provide an effective diagnostic tool for chronic bronchitis and asthma as well as for determining whether a patient having COPD has CB only or CB and emphysema.

Thus, in some embodiments, the present invention provides a method of diagnosing or identifying a risk of developing chronic bronchitis (CB) in a subject, comprising: measuring the amount of mucin present in a sputum sample from the subject; and diagnosing the subject as having CB or identifying the subject as being at risk of developing CB when the amount of mucin in the sputum sample is increased as compared to an amount of mucin measured in a control sample. In some embodiments, a control sample is from a control subject that is a "never smoker" (i.e., a subject that has never smoked) and is of a similar age or age group to the subject in need of diagnosis.

In some embodiments, the amount of mucin in the sputum sample from the subject having CB may be at least about 2 times the amount of mucin measured in a sputum sample from a control subject. In some embodiments, a subject may be diagnosed as having CB or identifying the subject as being at risk of developing CB when the amount (e.g., concentration) of mucin in the sputum sample from the subject is about 3000 µg/ml (+/−250 standard error of the mean (SEM)). In some embodiments, the amount of mucin in a control sputum sample may be about 1500 μg/ml (+/−190 SEM).

In some embodiments, the present invention provides a method of diagnosing or identifying a risk of developing chronic bronchitis (CB) in a subject, the method comprising: measuring the amount of mucin 5AC (MUC5AC) and/or the amount of mucin 5B (MUC5B) present in a sputum sample from the subject; and diagnosing the subject as having CB or identifying the subject as being at risk of developing CB when the measured amount of MUC5AC in the sputum sample from the subject is increased as compared to an amount of MUC5AC measured in a control sputum sample and/or when the measured amount of MUC5B in the sputum sample from the subject is increased as compared to the amount of MUC5B measured in a control sputum sample, wherein the control sputum sample is from a control subject that is never a smoker and does not have any acute or chronic lung diseases (e.g., asthma).

In some embodiments, the amount of MUC5AC in the sputum sample from the subject may be about 5 to about 10 times (e.g., 5, 6, 7, 8, 9, 10 times, or any value or range therein) the amount of MUC5AC measured in a control sputum sample and/or wherein the measured amount of MUC5B in the sputum sample from the subject may be about 2 to about 3 times the amount of MUC5B measured in a control sputum sample, wherein the control sputum sample is from a subject is never a smoker and does not have any acute or chronic lung diseases (e.g., asthma). In some embodiments, a subject may be diagnosed as having CB or may be identified as being at risk of developing CB when the measured amount of MUC5AC in the sputum sample from the subject is about 50-100 picomol/ml (e.g., about 50, 55, 60, 65, 70, 75, 80, 85, 90, 95, or 100 picomol/ml, or any range or value therein) and/or when the measured amount of MUC5B in the sputum sample from the subject is about 100-300 picomol/ml (e.g., about 100, 125, 150, 175, 200, 225, 250, 275, or 300 picomol/ml, or any range or value therein). In some embodiments, a control sputum sample may have an amount of MUC5AC of about 10 picomol/ml and/or an amount of MUC5B of about 100 picomol/ml.

An additional aspect of the invention relates to a method of diagnosing or identifying a risk of developing chronic bronchitis (CB) in a subject, comprising: measuring the amount of each of (a) mucin 5AC (MUC5AC) and (b) mucin 5B(MUC5B) present in a sputum sample from the subject; calculating a ratio of the measured amount of MUC5AC to the measured amount of MUC5B; diagnosing the subject as having CB or identifying the subject as being at risk of developing CB when the ratio is increased compared to a ratio of a measured amount of MUC5AC to a measured amount of MUC5 for a control sputum sample, wherein the control sputum sample is from a control subject that is never a smoker and does not have any acute or chronic lung diseases (e.g., asthma). In some embodiments, a subject diagnosed as having CB or identified as being at risk of developing CB may have a ratio of MUC5AC to MUC5B that is about 3-fold to 4-fold over a ratio of a measured amount of MUC5AC to a measured amount of MUC5 in a control sputum sample, wherein the control sputum sample is from a control subject that is never a smoker and does not have any acute or chronic lung diseases (e.g., asthma).

The present inventor has discovered that mucin concentrations and the ratio of MUC5AC and MUC5B, and their combination metric (i.e., (mucin×(MUC5AC÷MUC5B))÷100) may be used to diagnose chronic bronchitis and other muco-obstructive lung diseases such as non-CF bronchiectasis as well as asthma. This has been termed the Kesimer MUCQuant index (KMQuant index). Thus, the KMQuant index=(mucin concentration×(MUC5AC concentration÷MUC5B concentration))÷100).

Accordingly, in some embodiments, the present invention provides a method of diagnosing or identifying a risk of developing chronic bronchitis (CB) in a subject, comprising: measuring the amount of each of (a) mucin, (b) mucin 5AC (MUC5AC) and (c) mucin 5B(MUC5B) in a sputum sample from the subject; calculating a ratio of the measured amount of MUC5AC to the measured amount of MUC5B; calculating a Kesimer MUCQuant index (KMQuant index) by multiplying the ratio by the measured amount of mucin to provide a product and dividing the product by 100 (i.e., (mucin×(MUC5AC÷MUC5B))÷100); and diagnosing the subject as having CB or identifying the subject as being at risk of developing CB when the KMQuant index calculated for the sputum sample from the subject is increased as compared to a KMQuant index calculated for a control sputum sample from a subject that is never a smoker and does not have any acute or chronic lung diseases (e.g., asthma). In some embodiments, a subject may be diagnosed as having CB or identified as being at risk of developing CB when their KMQuant index is increased by about 5-fold to about 10 fold over the KMQuant index of the control sputum sample. In some embodiments, the KMQuant index may be used to diagnose a subject as having CB, wherein the subject is asymptomatic.

The present inventor has further discovered a relationship between particular proteins present in sputum samples with muco-obstructive, chronic-inflammatory, and immunological-allergic conditions. For instance, bactericidal/permeability-increasing fold-containing family member A1 (BPIFA1 (or SPLUNC1)) has been found to decrease, while IgGFc-binding proteins (FCGBP) increase in allergic asthma type2 (IL13) response. In particular, the ratio of these two proteins may reflect the pathogenetic disease specific background in the airways. In view of this unique observation, the ratio of the concentration of these two proteins is integrated into the KMQuant index or score and is named the MUCQuant Plus (+) index or score or the Kesimer MUCQuant+(KMQuant+) score or index. Thus, KMQuant+ index=[mucin]×([MUC5AC]÷[MUC5B])÷100×(FCGBP÷SPLUNC1). The associations between KMQuant and KMQuant+ indices and the pathogenesis of hypersecretory lung diseases suggests that these indices may be used as quantitative biomarker indices for both differential diagnosis and prognosis.

In some embodiments, the sputum sample for measurement of the FCGBP and SPLUNC1 proteins may be the same sputum sample as for measurement of the mucins. In some embodiments, the measurement of the FCGBP and SPLUNC1 proteins may be in a different sputum sample from the sputum sample in which the mucins are measured. When the FCGBP and SPLUNC1 proteins are measured in a different sputum sample than that in which the mucins are measured, the sample in which the proteins are measured may be taken at the same time or within a few minutes to about an hour before or after taking the sample for measuring the mucins (e.g., about 10, 20, 30, 40, 50 sec, about 1, 2, 3, 4, 5, 6, 7, 8, 9, 10, 15, 20, 30, 40, 50, 60, 70, 80, 90 minutes, or any range or value therein).

Accordingly, in some embodiments, the present invention provides a method of diagnosing or identifying a risk of developing chronic bronchitis (CB) in a subject, comprising: measuring the amount of each of (a) mucin, (b) mucin 5AC (MUC5AC) and (c) mucin 5B(MUC5B) in a sputum sample from the subject; calculating a ratio of the measured amount of MUC5AC to the measured amount of MUC5B; calculating a Kesimer MUCQuant index (KMQuant index) by multiplying the ratio by the measured amount of mucin to provide a product and dividing the product by 100 (i.e., (mucin×(MUC5AC÷MUC5B))÷100); measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; and calculating a MUCQuant plus (+) index (KMQant+ index) by multiplying the ratio of the measured amount of FCGBP to the measured amount of SPLUNC1 by the Kesimer MUCQuant index (KMQant index) ([mucin]×([MUC5AC]÷[MUC5B])÷100×(FCGBP÷SPLUNC1)), wherein the subject is diagnosed as having CB has a KMQuant+ index that is increase by about 250-fold to about 350-fold as compared to a KMQuant+ index calculated for a control sputum sample or the subject is identified as being at risk of developing CB has a KMQuant+index that is increased by about 10-fold to about 20-fold over a KMQuant+ index calculated for the control sputum sample.

In some embodiments, a subject having both CB and emphysema may have a higher mucin concentration in their sputum than a subject having CB only.

In some embodiments, the present invention provides a method for differentially diagnosing non-cystic fibrosis related bronchiectasis from CB in a subject, the method comprising: measuring the amount of each of (a) mucin, (b) mucin 5AC (MUC5AC) and (c) mucin 5B(MUC5B) in a sputum sample from the subject; calculating a ratio of the measured amount of MUC5AC to the measured amount of MUC5B; calculating a KMQuant index (Kesimer MUCQuant index) by multiplying the ratio by the measured amount of mucin to provide a product and dividing the product by 100 (mucin×(MUC5AC÷MUC5B))÷100); measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; calculating a MUCQuant plus (+) index (KMQuant+ index) by multiplying the ratio of the measured amount of FCGBP to the measured amount of SPLUNC1 by the KMQuant index ([mucin]×([MUC5AC]÷[MUC5B])÷100×(FCGBP+SPLUNC1)), and diagnosing the subject as having non-cystic fibrosis related bronchiectasis when the KMQuant+ index calculated for the sputum sample from the subject is at least about 2-fold higher than a KMQuant+ index determined for a CB sputum sample.

A KMQuant+ index determined for a CB sputum sample may be a predetermined range based on CB sputum samples from subjects diagnosed with CB. Thus, in some embodiments, a KMQuant+ index determined for a CB sputum sample may be in the range of about 85+/−1.6 and the subject may be differentially diagnosed as having non-cystic fibrosis related bronchiectasis when the KMQuant+ index calculated for the sputum sample from the subject is about 170 or higher.

Another aspect of the invention relates to a method of diagnosing CB or both CB and emphysema in a subject having chronic obstructive pulmonary disease (COPD), comprising: measuring the amount of mucin present in a sputum sample from the subject; and diagnosing the subject as having CB when the amount of mucin in the sample is about 2 times an amount of mucin measured in a control sputum sample or diagnosing the subject as having CB and emphysema when the amount of mucin measured in the sputum sample is about 3 times the amount of mucin measured in a control sputum sample. In some embodiments, the control sputum sample may be from a control subject that is never a smoker and does not have any acute or chronic lung diseases (e.g., asthma). In some embodiments, the subject may be diagnosed as having CB when the amount of mucin in the sputum sample is about 3000 Ag/ml or diagnosed as having CB and emphysema when the amount of mucin in the sputum sample is about 4000 ug/ml. In some embodiments, a control sputum sample may have an amount of mucin of about 1500 ug/ml.

A further aspect of the invention relates to a method of diagnosing CB or both CB and emphysema in a subject having chronic obstructive pulmonary disease (COPD), comprising: measuring the amount of mucin 5AC (MUC5AC) present in a sputum sample from the subject; and diagnosing the subject as having CB when the measured amount of MUC5AC in the sputum sample is increased as compared to an amount of MUC5AC measured in a control sputum sample or diagnosing the subject as having CB and emphysema when the measured amount of MUC5AC in the sputum sample is increased as compared to the amount of MUC5AC measured in a sputum sample from subject having CB only. In some embodiments, the subject may be diagnosed as having CB when the measured amount of MUC5AC in the sputum sample from the subject is about 5-8 times the amount of MUC5AC measured in the control sputum sample, or the subject may be diagnosed as having CB and emphysema when the measured amount of MUC5AC in the sputum sample from the subject is about 10 times the amount of MUC5AC measured in the control sputum sample, wherein the control sputum sample is from a control subject that is never a smoker and does not have any acute or chronic lung diseases (e.g., asthma). In some embodiments, the subject may be diagnosed as having CB when the measured amount of MUC5AC in the sputum sample from the subject is about 80 picomol/ml or may be diagnosed as having CB and emphysema when the measured amount of MUC5AC in the sputum sample from the subject is about 100 picomol/ml. In some embodiments, the measured amount of MUC5A in a control sputum sample may be about 10 picomol/ml.

In some embodiments, a method of diagnosing CB or both CB and emphysema in a subject having chronic obstructive pulmonary disease (COPD) is provided, the method comprising: measuring the amount of each of (a) mucin, (b) mucin 5AC (MUC5AC) and (c) mucin 5B(MUC5B) present in a sputum sample from the subject; calculating a ratio of the measured amount of MUC5AC to the measured amount of MUC5B; calculating a KMQuant index by multiplying the ratio by the measured amount of mucin to provide a product and dividing the product by 100; and diagnosing the subject as having CB when the KMQuant index is increased as compared to a KMQuant index calculated for a control sputum sample or diagnosing the subject as having CB and emphysema when the KMQuant index is increased as compared to a KMQuant index calculated for a sputum sample from a subject having CB only. In some embodiments, the subject may be diagnosed as having CB when the KMQuant index calculated for the sputum sample from the subject is about 5 fold higher than the KMQuant index calculated for the control sputum sample or may be diagnosed as having CB and emphysema when the KMQuant index calculated for the sputum sample from the subject is about 10 fold higher than the KMQuant index calculated for a control sputum sample. In some embodiments a control sputum sample may have a KMQuant index of about 1.

In some embodiments, the present invention further provides a method of diagnosing CB or both CB and emphysema in a subject having chronic obstructive pulmonary disease (COPD), the method comprising: measuring the amount of each of (a) mucin, (b) mucin 5AC (MUC5AC) and (c) mucin 5B(MUC5B) present in a sputum sample from the subject; calculating a ratio of the measured amount of MUC5AC to the measured amount of MUC5B; calculating a KMQuant index by multiplying the ratio by the measured amount of mucin to provide a product and dividing the product by 100; measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; calculating a KMQuant plus (+) index (MUCQuant+ index) by multiplying the ratio of the measured amount of FCGBP to the measured amount of SPLUNC1 by the KMQuant index; and diagnosing the subject as having CB when the KMQuant+ index calculated for the sputum sample from the subject is increase by about 250-fold to about 350-fold as compared to a KMQuant+ index calculated for the control sputum sample; or identifying the subject as being at risk of developing CB when the KMQuant+ index calculated for the sputum sample from the subject is increased by about 10-fold to about 20-fold over a KMQuant+ index calculated for the control sputum sample.

Another aspect of the invention relates to a method for diagnosing an exacerbation of chronic obstructive pulmonary disease (COPD) in a subject diagnosed with COPD, comprising: a) measuring an amount of mucin present in a first sputum sample taken from the subject at a first time point; b) measuring an amount of mucin in a second sputum sample taken from the subject at a subsequent time point; and c) comparing the amount of mucin in the first sputum sample to the amount of mucin in the second sputum sample, wherein an increase in the amount of mucin in the second sputum sample as compared to the first sputum sample diagnoses an exacerbation of COPD in the subject.

A further aspect of the invention relates to a method for diagnosing an exacerbation of chronic obstructive pulmonary disease (COPD) in a subject diagnosed with COPD, comprising: a) measuring an amount of each of (i) mucin, (ii) mucin 5AC (MUC5AC) and (iii) mucin 5B(MUC5B) in a first sputum sample taken from the subject at a first time point; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) mucin, (ii) MUC5AC and (iii) MUC5B in a second sputum sample taken from the subject at a time point subsequent to the first time point; e) calculating a second ratio of the measured amount of MUC5AC to the measured amount of MUC5B from the second sputum sample; f) calculating a second KMQuant index for the second sputum sample by multiplying the second ratio by the measured amount of mucin from the second sputum sample to provide a product and dividing the product by 100; and g) comparing the first KMQuant index calculated for the first sample (c) to the second KMQuant index calculated for the second sputum sample (f), wherein an increase in the KMQuant index calculated for the second sputum sample as compared to the KMQuant index calculated for the first sputum diagnoses an exacerbation of COPD in the subject.

In some embodiments, the method for diagnosing an exacerbation of chronic obstructive pulmonary disease (COPD) in a subject diagnosed with COPD, may further comprise: h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a KMQuant plus (+) index for the first sputum sample by multiplying the ratio of the measured amount of FCGBP to the measured amount of SPLUNC1 by the KMQuant index) measuring the amount of each of an IgGFc-binding protein (FCGBP) and a bactericidal/permeability-increasing fold-containing family member A1 (BPIFA1 (or SPLUNC1)) present in the second sputum sample from the subject; 1) calculating a ratio of the measured amount of FCGBP to the measured amount of SPLUNC1 in the second sputum sample; m) calculating a KMQuant+ index for the second sputum sample by multiplying the ratio of the measured amount of FCGBP to the measured amount of SPLUNC1 by the KMQuant index+; and n) comparing the KMQuant+ index calculated for the first sample (j) to the KMQuant+ index calculated for the second sputum sample (m), wherein an increase in the KMQuan+ index calculated for the second sputum sample as compared to the KMQuant+ index calculated for the first sputum diagnoses an exacerbation of COPD in the subject.

In some embodiments, when diagnosing an exacerbation of chronic obstructive pulmonary disease (COPD) in a subject diagnosed with COPD, the sputum sample that is taken from the subject may be taken at any time point prior to the second time point when the subject is not experiencing a suspected COPD exacerbation (e.g., a baseline COPD measurement). In some embodiments, the second time point is taken at any time point after the first time point during a time when the subject is experiencing a suspected COPD exacerbation.

In some embodiments, the invention provides a method of assessing the effectiveness of a treatment for CB in a subject, comprising: a) measuring an amount of each of mucin and/or mucin 5AC (MUC5AC) present in a first sputum sample taken from the subject at first time point prior to treatment for CB or during treatment of the subject for CB; b) measuring an amount of each of mucin and/or MUC5AC in a second sputum sample taken from the subject at a subsequent time point (e.g., subsequent to the first time point) during treatment of the subject for CB; and c) comparing the amount of mucin and/or the amount of MUC5AC from the first sputum sample (a) to the amount of mucin and/or the amount of MUC5AC from the second sputum sample (b), wherein an increase or no change in the amount of mucin or in the amount of MUC5AC in the second sputum sample as compared to the amount of mucin or the amount of MUC5AC in the first sputum sample indicates that the treatment is not effective, and a decrease in the amount of mucin or in the amount of MUC5AC in the second sputum sample as compared to the amount of mucin or the amount of MUC5AC in the first sputum sample indicates that the treatment is effective.

In some embodiments, a method of assessing the effectiveness of a treatment for CB in a subject is provided, the method comprising: a) measuring an amount of each of (i) mucin, (ii) mucin 5AC (MUC5AC), and (iii) mucin 5B(MUC5B) in a first sputum sample taken from the subject at a first time point prior to treatment for CB or during treatment for CB; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) mucin, (ii) MUC5AC and (iii) MUC5B in a second sputum sample taken from the subject at a subsequent time point during treatment of the subject for CB; e) calculating a second ratio of the measured amount of MUC5AC to the measured amount of MUC5B in the second sputum sample; f) calculating a second KMQuant index for the second sputum sample by multiplying the second ratio by the measured amount of mucin from the second sputum sample to provide a product and dividing the product by 100; and g) comparing the KMQuant index from the first sputum sample (c) to the KMQuant index from the second sputum sample (f), wherein an increase or no change in the KMQuant index calculated for the second sputum sample as compared to the KMQuant index calculated for the first sample indicates that the treatment is not effective, and a decrease in the KMQuant index calculated for the second sputum sample as compared to the KMQuant index calculated for the first sample indicates that the treatment is effective.

In some embodiments, the method of assessing the effectiveness of a treatment for CB in a subject may further comprise the steps of h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a KMQuant plus (+) index for the first sputum sample by multiplying the ratio of the measured amount of FCGBP to the measured amount of SPLUNC1 by the KMQuant index, k) measuring the amount of each of FCGBP and SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and (n) comparing the KMQuant+ index from the first sputum sample (j) to the KMQuant+ index from the second sputum sample (m), wherein an increase or no change in the KMQuant+ index calculated for the second sputum sample as compared to the KMQuant+ index calculated for the first sample indicates that the treatment is not effective, and a decrease in the KMQuant+ index calculated for the second sputum sample as compared to the KMQuant+ index calculated for the first sample indicates that the treatment is effective.

An additional aspect of the invention relates to a method of monitoring the progression of CB or a risk of developing CB in a subject, the method comprising: a) measuring an amount of each of (i) mucin, (ii) mucin 5AC (MUC5AC), and (iii) mucin 5B(MUC5B) in a first sputum sample taken from the subject at a first time point; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) mucin, (ii) MUC5AC and (iii) MUC5B in a second sputum sample taken from the subject at a subsequent time point (e.g., subsequent to the first time point); e) calculating a second ratio of the measured amount of MUC5AC to the measured amount of MUC5B in the second sputum sample; f) calculating a second KMQuant index for the second sputum sample by multiplying the second ratio by the measured amount of mucin from the second sputum sample to provide a product and dividing the product by 100; and g) comparing the KMQuant index from the first sputum sample (c) to the KMQuant index from the second sputum sample (f), wherein an increase in the KMQuant index calculated for the second sputum sample as compared to the KMQuant index calculated for the first sample indicates that CB in the subject is progressing, and a decrease in the KMQuant index calculated for the second sputum sample as compared to the KMQuant index calculated for the first sample indicates that CB in the subject is stable or improving.

In some embodiments, the method of monitoring the progression of CB or a risk of developing CB in a subject may further comprise: h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a KMQuant+ index for the first sputum sample by multiplying the ratio of the measured amount of FCGBP to the measured amount of SPLUNC1 by the KMQuant index); k) measuring the amount of each of an FCGBP and a SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and n) comparing the KMQuant+ index from the first sputum sample (j) to the KMQuant+ index from the second sputum sample (m), wherein an increase in the KMQuant+ index calculated for the second sputum sample as compared to the KMQuant+ index calculated for the first sample indicates that CB in the subject is progressing, and a decrease in the KMQuant+ index calculated for the second sputum sample as compared to the KMQuant+ index calculated for the first sample indicates that CB in the subject is stable or improving.

A further aspect of the invention relates to a method of diagnosing asthma and/or asthma severity, comprising: measuring the amount of each of (a) mucin, (b) the amount of mucin 5AC (MUC5AC), and (c) the amount mucin 5B(MUC5B) present in a sputum sample from the subject; calculating a ratio of the measured amount of MUC5AC to the measured amount of MUC5B from the sputum sample; calculating a KMQuant index by multiplying the ratio of the measured amount of MUC5AC to the measured amount of MUC5B by the measured amount mucin to provide a product and dividing the product by 100; and diagnosing the subject as having mild or moderate asthma when the KMQuant index calculated for the sputum sample is at least about 20 fold higher than a KMQuant index calculated for a control sputum sample, or diagnosing the subject as having severe asthma when the KMQuant index calculated for the sputum sample is about 100 fold higher than a KMQuant index calculated for a control sputum sample. In some embodiments, a control sputum sample may have a KMQant index of about 1. In some embodiments, the method of diagnosing asthma and/or asthma severity, may further comprise: measuring the amount of each of an IgGFc-binding protein (FCGBP) and a bactericidal/permeability-increasing fold-containing family member A1 (BPIFA1 (or SPLUNC1)) present in the sputum sample from the subject; calculating a ratio of the measured amount of FCGBP to the measured amount of SPLUNC1; calculating a MUCQuant plus (+) index (KMQuant+ index) by multiplying the ratio of the measured amount of FCGBP to the measured amount of SPLUNC1 by the Kesimer MUCQuant index (KMQuant index), and diagnosing the subject as having mild or moderate asthma when the KMQuant+ index calculated for the sputum sample is at least about 350 fold higher than a KMQuant+ index calculated for a control sputum sample, or as having severe asthma when the KMQuant+ index calculated for the sputum sample is about 6500 fold higher than a KMQuant+ index calculated for a control sputum sample.

In some embodiments, the present invention provides a method of guiding treatment of a subject diagnosed with COPD, the method comprising: a) measuring an amount of each of (i) mucin, (ii) mucin 5AC (MUC5AC) and (iii) mucin 5B(MUC5B) in a first sputum sample taken from the subject at a first time point; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) total mucin, (ii) MUC5AC and (iii) MUC5B in a second sputum sample taken from the subject at a subsequent time point (e.g., subsequent to the first time point); e) calculating a second ratio of the measured amount of MUC5AC to the measured amount of MUC5B from the second sputum sample; f) calculating a second KMQuant index for the second sputum sample by multiplying the second ratio by the measured amount of mucin from the second sputum sample to provide a product and dividing the product by 100; and g) comparing the first KMQuant index calculated for the first sample (c) to the second KMQuant index calculated for the second sputum sample (f), wherein an increase in the KMQuant index calculated for the second sputum sample as compared to the KMQuant index calculated for the first sputum sample indicates that the treatment is not effective and the treatment is discontinued or changed, and a decrease in the KMQuant index calculated for the second sputum sample as compared to the KMQuant index calculated for the first sputum sample indicates that the treatment is effective and the treatment is continued.

In some embodiments, the method of guiding treatment of a subject diagnosed with COPD may further comprise: h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a MUCQuant plus (+) index (KMQuant+ index) for the first sputum sample by multiplying the ratio of the measured amount of FCGBP to the measured amount of SPLUNC1 by the Kesimer MUCQuant index (KMQuant index); k) measuring the amount of each of an FCGBP and a SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and n) comparing the first KMQuant+ index from the first sputum sample (j) to the second KMQuant+ index from the second sputum sample (m), wherein an increase in the KMQuant+ index calculated for the second sputum sample as compared to the KMQuant+ index calculated for the first sputum sample indicates that the treatment is not effective and the treatment is discontinued or changed, and a decrease in the KMQuant+ index calculated for the second sputum sample as compared to the KMQuant+ index calculated for the first sputum sample indicates that the treatment is effective and the treatment is continued.

In some embodiments, a method of guiding treatment of a subject diagnosed with CB is provide, the method comprising: a) measuring an amount of each of mucin and/or mucin 5AC (MUC5AC) present in a first sputum sample taken from the subject at first time point prior to treatment for CB or during treatment of the subject for CB; b) measuring an amount of each of mucin and/or MUC5AC in a second sputum sample taken from the subject at a subsequent time point (e.g. subsequent to the first time point) during treatment of the subject for CB; and c) comparing the amount of mucin from the first sputum sample (a) to the amount of mucin from the second sputum sample (b), wherein an increase or no change in the amount of mucin or in the amount of MUC5AC in the second sputum sample as compared to the amount of mucin or the amount of MUC5AC in the first sputum sample indicates that the treatment is not effective and the treatment is discontinued or changed, and a decrease in the amount of mucin or in the amount of MUC5AC in the second sputum sample as compared to the amount of mucin or the amount of MUC5AC in the first sputum sample indicates that the treatment is effective and the treatment is continued.

In some embodiments, a method of guiding treatment of a subject diagnosed with CB is provided, the method comprising: a) measuring an amount of each of (i) mucin, (ii) mucin 5AC (MUC5AC), and (iii) mucin 5B(MUC5B) in a first sputum sample taken from the subject at a first time point prior to treatment for CB or during treatment for CB; b) calculating a first ratio of the measured amount of MUC5AC to the measured amount of MUC5B from the first sputum sample; c) calculating a first KMQuant index for the first sputum sample by multiplying the first ratio by the measured amount of mucin from the first sputum sample to provide a product and dividing the product by 100; d) measuring an amount of each of (i) mucin, (ii) MUC5AC and (iii) MUC5B in a second sputum sample taken from the subject at a subsequent time point (e.g., subsequent to the first time point) during treatment of the subject for CB; e) calculating a second ratio of the measured amount of MUC5AC to the measured amount of MUC5B in the second sputum sample; f) calculating a second KMQuant index for the second sputum sample by multiplying the second ratio by the measured amount of mucin from the second sputum sample to provide a product and dividing the product by 100; and g) comparing the first KMQuant index from the first sputum sample (c) to the second KMQuant index from the second sputum sample (f), wherein an increase or no change in the KMQuant index calculated for the first sample as compared to the KMQuant index calculated for the second sputum sample indicates that the treatment is not effective and the treatment is discontinued or changed, and a decrease in the KMQuant index calculated for the first sample as compared to the KMQuant index calculated for the second sputum sample indicates that the treatment is effective and the treatment is continued.

In some embodiment, the method of guiding treatment of a subject diagnosed with CB may further comprise: h) measuring the amount of each of an IgGFc-binding protein (FCGBP) and a bactericidal/permeability-increasing fold-containing family member A1 (BPIFA1 (or SPLUNC1)) present in the first sputum sample from the subject; i) calculating a ratio of the measured amount of FCGBP to the measured amount of SPLUNC1 in the first sputum sample; j) calculating a MUCQuant plus (+) index (KMQuant+ index) for the first sputum sample by multiplying the ratio of the measured amount of FCGBP to the measured amount of SPLUNC1 by the Kesimer MUCQuant index (KMQuant index), k) measuring the amount of each of an FCGBP and a SPLUNC1 present in the second sputum sample taken from the subject at a subsequent time point (e.g., subsequent to the first time point) during monitoring of the subject for CB; l) calculating a second ratio of the measured amount of MUC5AC to the measured amount of MUC5B in the second sputum sample; m) calculating a second KMQuant+ index for the second sputum sample by multiplying the second ratio by the measured amount of mucin from the second sputum sample to provide a product and dividing the product by 100; and comparing the first KMQuant+ index from the first sputum sample (j) to the second KMQuant+ index from the second sputum sample (m), wherein an increase in the KMQuant+ index calculated for the second sputum sample as compared to the KMQuant+ index calculated for the first sputum sample indicates that the treatment is not effective and the treatment is discontinued or changed, and a decrease in the KMQuant+ index calculated for the second sputum sample as compared to the KMQuant+ index calculated for the first sputum sample indicates that the treatment is effective and the treatment is continued.

The present invention additionally provides methods of treating chronic bronchitis. Thus, in some embodiments, a method of treating chronic bronchitis in a subject in need thereof is provided, comprising diagnosing the subject as having CB or being at risk of developing CB by the method of the present invention, and administering to the subject a therapeutically effective amount of an osmotic agent for airway surface hydration, an epithelial sodium channel (ENaC) blockers, an inhibitor of mucin secretion, an inhibitor of mucin, production, a cystic fibrosis transmembrane regulator (CFTR) corrector and/or a CTFR potentiator. An osmotic agent includes, but is not limited to, hypertonic saline or mannitol. In some embodiments, a CFTR corrector may be Lumacaftor (VX-809). In some embodiments, a CTFR potentiator may be Ivacaftor (VX-770, KALYDECO®). In some embodiments, treating may comprise administering a combination of a CFTR corrector and a CTFR potentiator (e.g., lumacaftor and ivacaftor, e.g., ORKAMBI™).

In some embodiments, a subject having been diagnosed as having CB or identifying the subject as being at risk of developing CB may be advised to cease smoking. Any number of methods are known in the art may be used to assist in the process of smoking cessation.

Diagnosing, monitoring the progression of disease, assessing the effectiveness of a treatment, or guiding treatment of a subject may be carried out over hours, days, weeks, months and/or years and may involve taking and/or comparing of one or more samples (e.g., 1, 2, 3, 4, 5, 6, 7, 8, 9, 10 or more).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

The present invention analyzed the relationship between mucin concentration and chronic bronchitis sputum production and disease severity using the SPIROMICS Cohort. This cohort has been extensively phenotyped, including chronic bronchitis diagnostic questionnaires, spirometry, CT scanning/analysis for emphysema, and induced sputum. Associations between mucin concentrations measured by SEC-MALLS/dRI techniques and sputum/phlegm production, characteristics and disease severity, as indexed by spirometry and exacerbation frequency, were tested. The potential etiologic pathways for raised mucin concentrations, including cigarette smoking and asthma, were also analyzed. Absolute levels of MUC5AC and MUC5B were measured by mass spectroscopy in a SPIROMICS subgroup and relationships of each mucin to chronic bronchitis and asthma evaluated. Finally, the utility of sputum mucin concentrations, as well as subcomponents of the mucin were assessed as objective biomarkers for chronic bronchitis diagnosis.

Methods and Materials

Study Design:

SPIROMICS is a 2,981 participant, 11 clinical site observational study of COPD. Participants were recruited into the following four groups (strata): (1) never-smoker (control) participants; (2) cigarette smokers without airway obstruction; (3) cigarette smokers with mild-moderate airway obstruction and, (4) cigarette smokers with severe airflow obstruction (Table 1). Cigarette smokers ("ever-smokers") were defined as >20 pack year past or current histories. Chronic bronchitis was defined using classic and SGRQ instruments, an emphysema was determined from volumetric multidetector-row computed lung tomography (MDCT). Induced sputum for mucin concentrations was collected from 917 participants, according to the protocol (Table 2 and Table 3) and ATS/ERS standards in participants with FEV1>35% predicted. Induced sputum samples were placed in 6M guanidine buffer, shipped to the SPIROMICS Biospecimen Processing Center, and stored at −4 C. The SPIROMICS protocol was approved by the individual participating universities, and participants provided written informed consent.

Classic chronic bronchitis questionnaire and induced sputum mucin data were also collected at an independent site in 94 never-smokers and ever-smokers with and without chronic bronchitis (Table 4). Sputum sample handling and measurement technologies were identical to SPIROMICS procedures.

Chronic Bronchitis:

Two definitions of chronic bronchitis were utilized, Classic chronic bronchitis and SGRQ chronic bronchitis.

A. "Classic" Chronic Bronchitis

The first definition is the "Classic" chronic bronchitis definition defined as having a cough that is present during most days or nights, is present for 3 consecutive months of the year for two and more consecutive years, and results in phlegm production. The presence of Classic chronic bronchitis was obtained from the participant's baseline respiratory disease questionnaire via the following questions:
1. Do you usually cough? (Exclude clearing of throat)
   a. If yes, do you usually cough as much as 4 times a day, 4 or more days out of the week?
2. Do you usually cough at all on getting up in the morning? (Y/N)
3. Do you usually cough at all during the rest of the day or night? (Y/N)
If yes to any of the above (1, 2, 3) answer the following:
   a. Do you cough like this on most days, for 3 consecutive months or more during the year? (Y/N)
   b. For how many years have you had this cough? (years)
4. Do you usually bring up phlegm from your chest? (Y/N)
   a. If yes, do you usually bring up phlegm like this as much as twice a day, 4 or more days out of the week? (Y/N)
5. Do you bring up phlegm from your chest on getting up, or first thing in the morning? (Y/N)
6. Do you bring up phlegm from your chest during the rest of the days or at night? (Y/N)
If yes, to any of the above (4, 5, 6), answer the following:
   a. Do you bring up phlegm like this on most days for 3 consecutive months or more during the year? (Y/N)
   b. For how many years have you had trouble with this phlegm?(years)

The diagnosis of chronic bronchitis is made if the answer to question 3a is "Yes," and the numerical value in 3b is "2 years or greater," and the participant answered "Yes" to question 6a and the duration of 6b is "greater than 2 years." If the participant answered "No" to questions 1, 2, or 3 or the duration of the symptoms was "less than 2 years" then the diagnosis was not made.

B. SGRQ Chronic Bronchitis

The second definition of chronic bronchitis used was based upon cough and phlegm questions from a modified St. George Respiratory Questionnaire (SGRQ). The diagnosis of chronic bronchitis was defined as having cough and phlegm almost every day or several times a week. The presence of chronic bronchitis was obtained from the participant's answers to the following questions.
1. Over the last 4 weeks, I have coughed:
   Almost every day
   Several days a week
   A few days a month
   Only with lung/respiratory infections
   Not at all
2. Over the last 4 weeks, I have brought up phlegm (sputum):
   Almost every day
   Several days a week
   A few days a month
   Only with lung/respiratory infections
   Not at all The diagnosis of chronic bronchitis was made when participants answered "Yes" to questions 1 (almost every day, or several days a week) and "Yes" to question 2 (almost every day, or several days a week).

Phlegm: The definition of phlegm used in the manuscript was based on the SGRQ.
1. I bring up phlegm
   Most days a week
   Several days a week
   A few days a month
   Only with respiratory infections
   Not at all The diagnosis of bringing up phlegm was determined by answering "Yes" to "most days a week" and/or "several days a week."

Phlegm Characteristics:

Characteristics were determined by technician who collected and processed the induced sputum. Technicians filled out a Sputum Processing Worksheet for each subject indicating consistency (watery, mucoid, purulent), and "plugs" (numerous, moderate, sparse).

Asthma:

The definition of current asthma is based on participants who self-report being diagnosed with asthma by a physician, either as a child (<18 years old) or in adulthood (>18 years old) and report still having it.

Never asthma is based on participants who self-report never being diagnosed with asthma either in childhood or adulthood.

Childhood asthma is based on participants self-report of having asthma in childhood. In any analysis involving current asthma, we excluded past asthma which was self-reporting a diagnosis of asthma by physician, but report no longer having it. In any analysis involving childhood asthma, we excluded any diagnosis of asthma made in adulthood only. If no age was specified, participants were also excluded from analysis. Note, all mucin concentration analysis were in gold stage 1, 2, 3 consistent with ACOS definition.

Exacerbation:

Exacerbation rates are calculated by dividing the count of exacerbations by follow-up time and multiplying by 365.

Severe Exacerbation: Any exacerbation that resulted in an emergency department visit or hospitalization.

Exacerbation requiring health care utilization: Any exacerbation that resulted in a contact with a health care provider, including emergency department and hospitalization.

Emphysema:

Emphysema was diagnosed from volumetric multidetector-row computed tomography (MDCT) of the lungs using an emphysema index of percent voxels in the lung field<−950 HU. Because MESA-lung utilized the same scan protocol as SPIROMICS, we were able utilize the normative equations established based upon 3,137 participants selected as "normal" from a prospective cohort from MESA (Hoffman et al., Annals of the American Thoracic Society 2014; 11:898-907). The normative equations served to adjust the emphysema index for current vs. former smokers, age, height sex, race/ethnicity*, scanner manufacturer, and BMI. If the participant is a current smoker, the equation is further adjusted by the number of cigarettes smoked per day in the time period of being studied. If the emphysema index is ≥upper limit of normal for a given participant, they were categorized as emphysema positive (Em+), otherwise they were considered emphysema negative (Em−). *=If the participant indicates they are Hispanic, regardless of the race selection, then they are adjusted for Hispanic ethnicity only (no race adjustment). If they are not Hispanic and indicate any black race (regardless of other race selections), then they are adjusted for black race only (regardless of any other race indicated). If participants indicate they are not Hispanic or black, and indicate Asian race or Asian and Pacific Islander, then the participant is adjusted for race using the Chinese values.

Additional Methods and Materials

Quantitation of all Types of Mucins (Total Mucin) in Sputum:

Mucins in sputum were determined by size exclusion chromatography/differential refractometry (SEC-MALLS/dRI) measurements. Sputum samples were diluted 1:5 in PBS and subjected to SEC/dRI mucin concentration measurements. A 250 µL aliquot of diluted sputum was injected into a CL2B size exclusion column (2×5 ml, GE Life Sciences) to separate mucin from other proteins and eluted with PBS. The column effluent was passed through an in-line enhanced optimal system laser photometer (Dawn Heleos II; Wyatt Technology) coupled to a digital signal-processing inferometric refractometer (Optilab t-REX; Wyatt Technology) to continuously measure light scattering and sample concentrations, respectively. The MALLS detector identified and quantitated mucin peaks. Data were analyzed using Astra (v6.1.1.7, Wyatt Technology). A dn/dc of 0.165 ml/g was used for mucins. Total respiratory mucins include the secreted gel forming mucins MUC5B and MUC5AC (>90% total and a small component of shed tethered mucins, e.g. MUC1, MUC4, MUC16, and MUC2).

Stable Isotope Dilution Mass Spectrometry for Mucin Quantitation:

A Novel Parallel Ion Monitoring (PRM) based method was developed for mucin quantitation. 50 µl of sputum from each sample were denatured with 900 µl of 6M GuHCl (pH 8.0). Samples were reduced by adding DTT to a final concentration of 20 mM for 1 hour at 65 degree. After reduction, samples were alkylated with iodoacetamide (Sigma) at a final concentration of 50 mM for 1 h at 25° C. in the dark. 1.5 ml of the reduced and alkylated samples was subjected to a HiTrap Desalting column (Sephadex G-25, Amersham Biosciences) to exchange the buffer to 50 mM ammonium hydrogen carbonate ($NH_4HCO_3$). Two ml of eluents were collected. 0.5 µg modified trypsin (proteomics grade, Sigma) was added to samples, and then incubated 18 h at 37° C. Large glycopeptides were removed by centrifugal filtration with a molecular weight cutoff of 10 kDa (Millipore, Bedford, USA). Samples were vacuum dried to remove bicarbonate salts. The digest peptides were resolubilized in 20 µL 0.1% formic acid water or were stored −30° C. until MS experiments.

For MS-PRM mucin quantitation, six heavy labeled peptide internal standards (see below) from different regions of MUC5B and MUC5AC were synthesized at concentrations of 5 pmol/µL±25% with purity>97% (HeavyPeptides AQUA QuantPro; Thermo Fisher, Ulm, Germany). All six peptides were mixed and spiked into sputum digests at final concentrations of 100 fmol/µL. A 1 µl aliquot from each digested sample was subjected to tSIM-DIA analysis using a hybrid quadrupole Orbitrap mass spectrometer with a Nano spray source (Q-Exactive, Thermo Fisher, Bremen, Germany) via a Dionex ultimate 3000 RSLCnano system.

For liquid chromatography, samples were loaded into a trap column Acclaim PepMap 100, 100 m×2 cm, nanoViper C18 5 µm 100 Å, at 5 µL/min with aqueous solution containing 0.1% (v/v) trifluoroacetic acid and 2% acetonitrile. The column used for peptides separation was an Acclaim PepMap RSLC, 75 Cpm×15 cm, nanoViper C18 2 µm 100 Å.

For Mass spectrometry, peptides were analyzed by a target method combining a tSIM scan method with a time-scheduled duplexed DIA method. For targeting SIM (tSIM) event, data were acquired at resolution of 70,000 at m/z 200, target AGC value of 5e5, maximum fill times of 200 ms, a multiplex degree of 6 with an isolation width of 3 m/z. The subsequent DIA scan was triggered by a time scheduled inclusion list with 0±5 min retention time windows. The scan was performed at a resolution of 35,000, individual isolation windows of 3.0 m/z, target AGC values of 2e5, maximum fill times set to auto with equal individual fill times, and a multiplex degree of 2. Fragmentation was performed with a normalized collision energy of 27.

Data Processing:

All raw files obtained from tSIM-DIA analyses of sputum digest samples were processed by Skyline (version v1.4). For each peptide the ratio between the corresponding endogenous and internal standard peak areas of each precursor (MS) and top 3 most intensity product ions (MS/MS) was calculated. Ratios from three peptides were averaged and MUC5B and MUC5AC concentrations were calculated as follows:

$$\text{Protein concentration} = [L/H \times C \times a/b \times c/d]$$

Where L/H is the average area ratio between light and heavy peptides, C concentration of the internal standard injected in the LC (100 fmol/µL), a is the volume used to resuspend the peptides (20 µL), b is the sample starting volume (50 µL), c/d is the dilution factor for mixing sample and internal standard (10/8). The peptides chosen for MUC5B and MUC5AC are provided below, in which the heavy isotope is designated.

MUC5B
TWL[Val(13C5; 15N)]PDSR
LTPLQFGNLQ[Lys(13C6; 15N2)]
LTDPNSAFS[Arg(13C6; 15N4)]
MUC5AC
AEDAPGVPL[Arg(13C6; 15N4)]
GTFLDDTG[Lys(13C6; 15N2)]
GTDSGDFDTLENL[Arg(13C6; 15N4)

Label free quantitative (LFQ) mass spectrometery was essentially performed as previously described. An aliquot from sputum (50 uL) was reduced, alkylated and digested with trypsin and glycopeptides were removed using a Superdex 200 column with $NH_4HCO_3$ 50 mM. The peptides were freeze-dried, dissolved in 50 µL of formic acid 0.1% and analyzed by LC-MS-MS. Peptides were subjected to label free proteomic analysis for all proteins detected. The data were acquired using a hybrid quadrupole orbitrap mass spectrometer with a Nano spray source (Q-Exactive, Thermo Fisher, Bremen, Germany). For liquid chromatography, 1 µL of the sample was loaded into a trap column Acclaim PepMap 2 cm×75 µm [i.d., C18, 3 µm, 100 A (Dionex)] at 5 µL/min with aqueous solution containing 0.05% (v/v) trifluoroacetic acid and 2% acetonitrile. Peptide mass spectra were analyzed by a data-dependent top 10 method dynamically choosing the most abundant precursor ions from the survey scan (300-1650 Th) for HCD fragmentation.

LFQ of Alpha Amylase, MUC5AC, and MUC5B was performed with Scaffold 4.6.1, and it was based on Total Precursor Intensity Quantitation, which uses the peak area in the MS1 chromatogram, providing a measure of the relative abundance of the corresponding peptide in each sample.

MS/MS spectra were used to identify peptides and they were matched to the corresponding MS1 peaks in each LC-MS/MS run. The areas under these peaks were calculated and used as measure of the relative abundance of the peptides in different samples. Relative quantities of proteins were estimated by summing the precursor intensities of the constituent peptides. All the graph and statistical analysis were performed with GraphPad Prism Version 6.07.

Additional Statistical Methods:

Statistical analyses were performed using SAS 9.4 software (SAS Institute, Cary, NC). Mucin concentrations and MUC5B and MUC5AC absolute quantifications were normalized with a natural log transformation. Normality of the data was verified using an ensemble of tests (Shapiro-Wilk, Kolmogorov-Smirnoff and Anderson-Darling). Homogeneity of variance was verified using the F-test of equality of two variance or Levene's Test when more than 2 groups when compared. ANOVA were used to determine the effect of categorical variables on mucin concentration, MUC5B, and MUC5AC. Multiple factors ANOVA were used to check the interactions of variables of interest, which were all found not-significant. All pairwise comparisons between individual groups were adjusted with the Tukey-Kramer method. The Chi-Square test for independence was used to determine the association of 2 categorical variables. Effects of continuous variables on mucin concentration were analyzed with scatterplot, Spearman correlation, and linear regression.

The effect of mucin concentration on the association with CB was established with a logistic regression, with control for potential confounders. All tests were two-sided with a significant level of alpha=0.05

The associations of COPD disease severity and MUC5B and MUC5AC concentrations were analyzed via Strata (recruitment group), in order to maintain sufficient power (above 0.7).

Example 2

Mucin Quantitation:

Sputum samples were subjected to SEC-MALLS/dRI mucin concentration measurements. Aliquots were injected into size exclusion columns to separate mucins from other proteins and effluents passed through an in-line enhanced optimal system laser photometer (HELEOS-II; Wyatt) coupled to a refractometer (T-rEx, Wyatt). Data were analyzed using Astra (v6.1.1.7, Wyatt).

A Mass Spectrometry Parallel Reaction Monitoring (PRM) labeled mucin quantitation technique quantitated MUC5B and MUC5AC. Briefly, 50 µl from sputum samples were reduced, alkylated, digested with trypsin, and six MUC5B and MUC5AC heavy labeled peptide internal standards spiked into digests at final concentrations of 100 fmol/µL. Samples were subjected to tSIM-DIA analysis using a hybrid quadruple Orbitrap mass spectrometer with a Nano spray source (Q-Exactive™, Thermo).

To assess salivary contamination, 86 samples randomly selected from all groups were subjected to label free proteomics. The abundance of peptides representing the salivary protein amylase was analyzed.

Statistical Methods:

Statistical analyses were performed using SAS 9.4 software. Concentrations of mucin, MUC5B and MUC5AC were normalized via natural log transformations. ANOVAs were used to determine the effect of categorical variables on mucin, MUC5B, and MUC5AC concentrations. All pairwise comparisons between individual groups were adjusted with the Tukey-Kramer method. All tests were two-sided with a significant level of alpha=0.05. Effects of continuous variables on mucin concentration were analyzed with scatter plots, correlations, and regression analyses. Analysis of sputum mucin diagnostic utility for chronic bronchitis utilized receiver operating characteristics curve techniques.

Characteristics of the participants in the mucin concentration (N=917) and absolute levels of MUC5B/AC (N=149) measurement group across the recruitment cohort are found in Tables 1-3, above. Characteristics of the 94 single site cohorts are displayed in Table 4, above.

Mucin Concentrations and Sputum/Phlegm Production, and Quality.

Figure 1B:
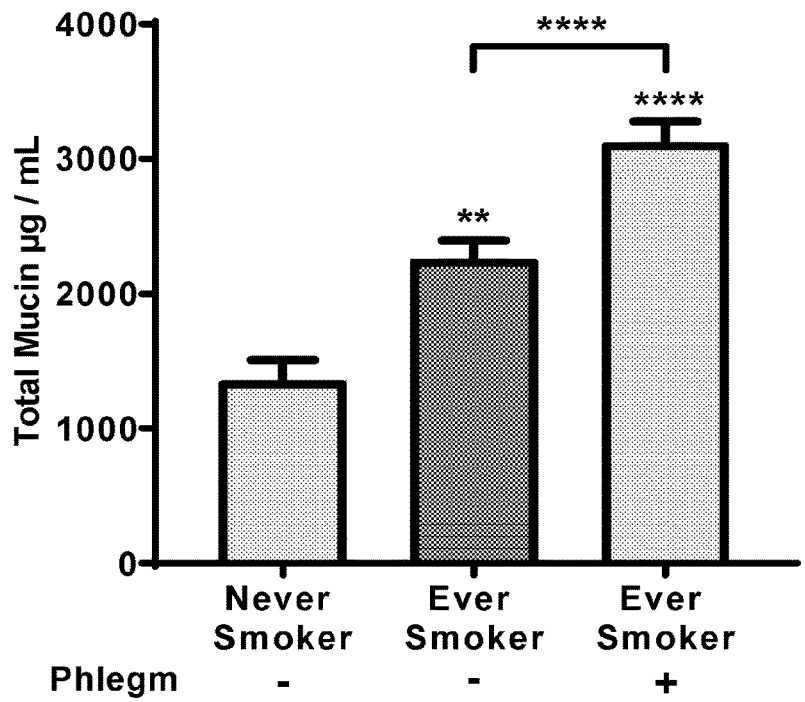
Figure 1C:
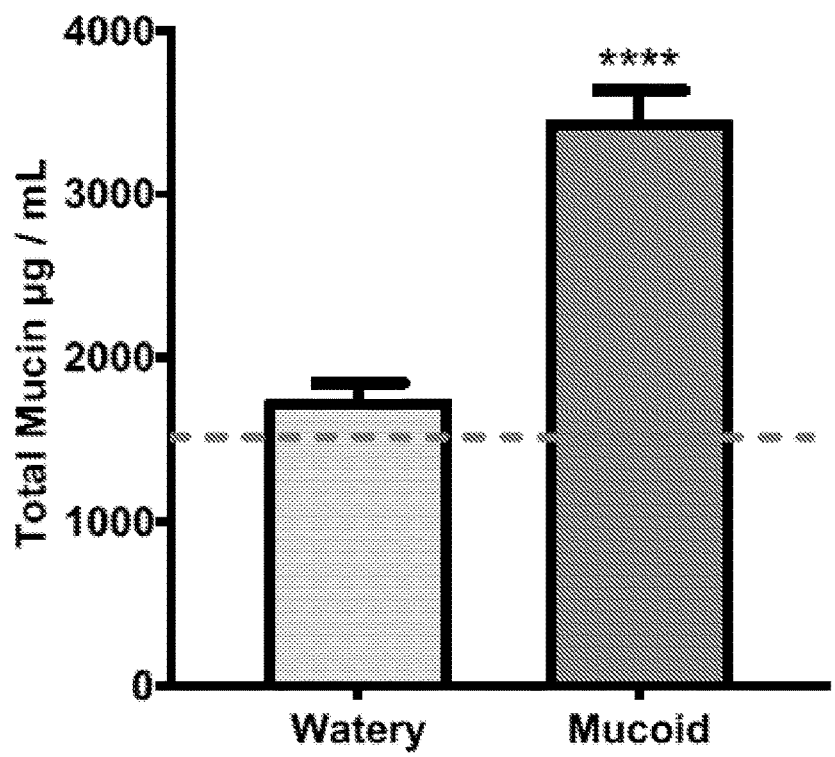
Figure 1D:
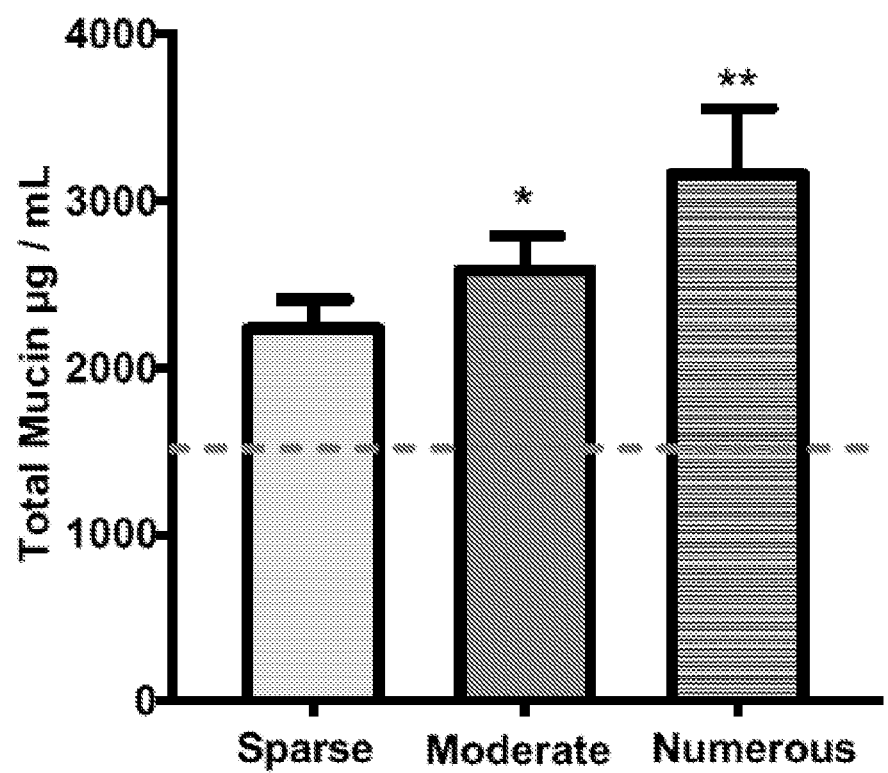

We first tested the relationships predicted by the two-gel hypothesis between total sputum mucin concentrations and sputum/phlegm production and properties (FIG. 1A). Consistent with predictions of this hypothesis, sputum mucin concentrations were raised in the SPIROMICS ever-smokers who reported sputum/phlegm production compared to normal (never-smoker) participants or ever-smokers with no phlegm production (FIG. 1B). The relationship between mucin concentration and phlegm production remained significant after correcting for cough, smoking status, asthma status, and exacerbation frequency (Table 5). Associations were also found between mucin concentrations and the mucoid, gel-like appearance of sputum samples and the numbers of gel-like plugs in sputum samples (FIGS. 1C-1D).

Salivary contamination in sputum could bias observed mucin concentration-sputum relationships. However, mass spectroscopy analyses of salivary amylase of 86 randomly selected sputum samples revealed no differences in amylase values per group, nor correlations between amylase and mucin levels.

Figure 2A:
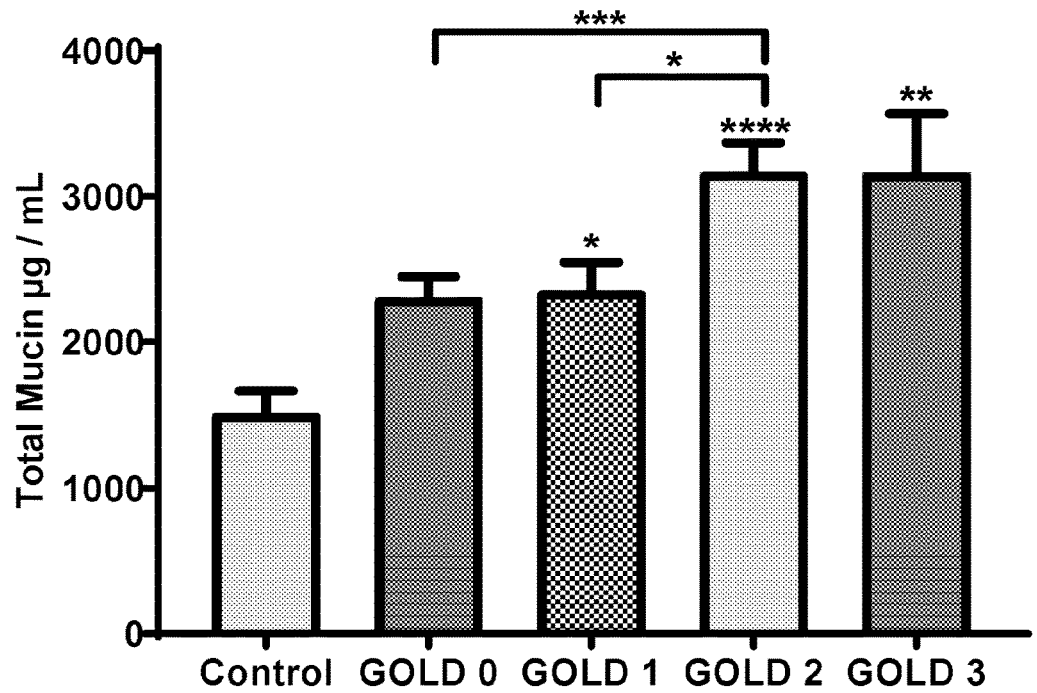
FIGS. 2A-2D are graphs showing the mucin concentration as it relates to disease severity and pathogenesis of COPD.
Figure 2B:
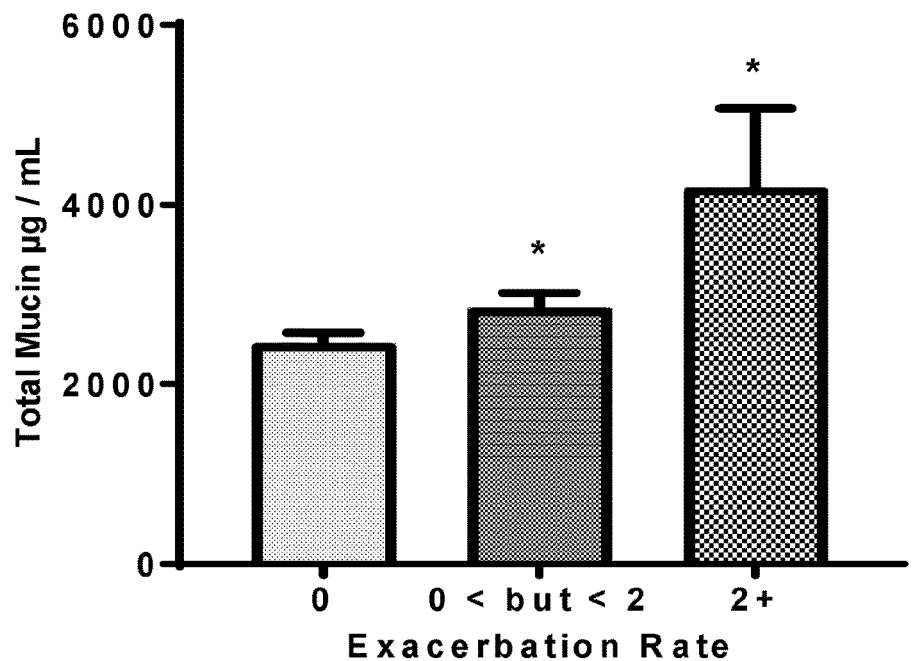
Figure 5:
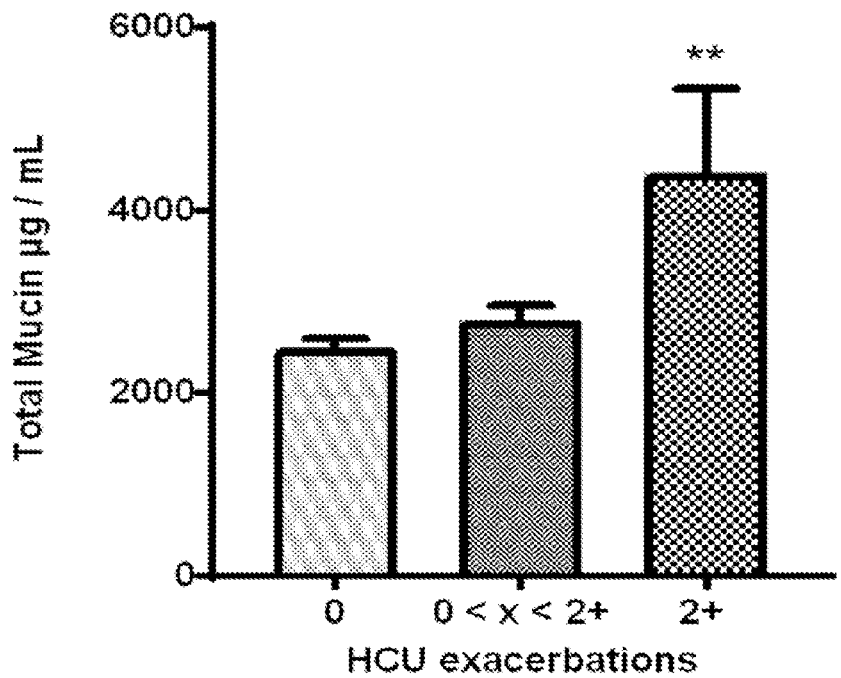
FIG. 5 is a graph showing the relationship between mucin concentrations and exacerbations requiring health care utilization. HCU is defined as exacerbation requiring contact with a healthcare provider including emergency department visits or hospitalization. Participants with 2 or more HCU exacerbations (N=34) have higher mucins compared to those with less than 2 (N=249) and significantly higher than those with none (N=611). **P value=0.0049.

Mucin Concentrations and Disease Status:

Relationships predicted by the two-gel hypothesis between mucin concentration and chronic bronchitis disease progression/severity were tested, including airflow obstruction and exacerbations. Analyses of SPIROMICS participants revealed that mucin concentrations were associated with disease severity as indexed by the spirometric criteria established by the Global Initiative for Obstructive Lung Disease (GOLD) (FIG. 2A). The correlation between mucin concentrations and GOLD status remained significant when inhaled bronchodilator and corticosteroid use were included in ANOVA models (p=0.0013). Relationships between mucin concentrations and prospective total exacerbation frequencies revealed that SPIROMICS participants with two or more exacerbations/year exhibited mucin concentrations higher than participants with fewer than two exacerbations/year (FIG. 2B). Similar associations were observed for frequencies of exacerbations requiring interactions with healthcare providers (FIG. 5).

Figure 2C:
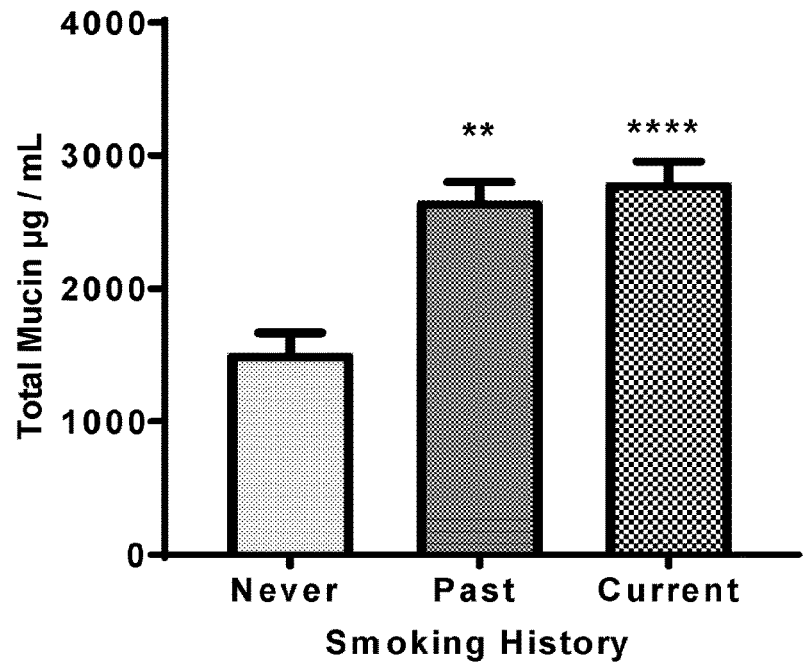
Figure 2D:
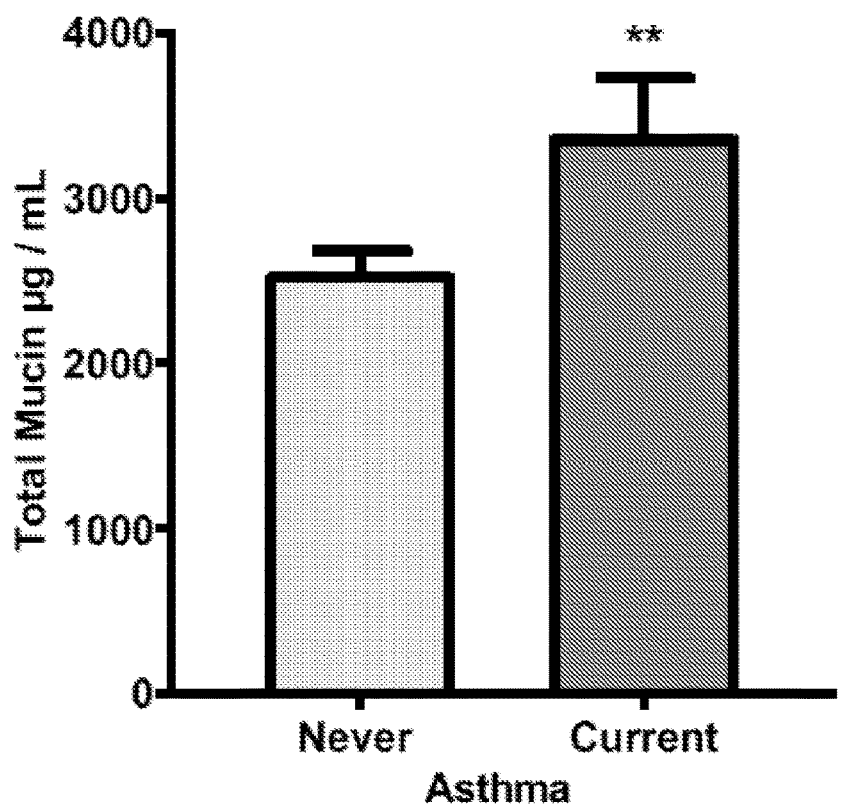

Etiology of Raised Chronic Bronchitis Mucin Concentrations—Cigarette Smoke Exposure and Asthma:

Laboratory data suggest that cigarette smoke exposure decreases airway surface hydration and stimulates mucin secretion, both predicted to increase mucin concentrations (FIG. 1A). In the SPIROMICS cohort, history of cigarette use, both past and current, was significantly associated with mucin concentrations (FIG. 2C).

Next, based on reports that asthma is associated with mucin hypersecretion, the relationships between a self-report diagnosis of current asthma and mucin concentration were tested. Approximately 15% of the ever-smoker SPIROMICS cohort reported current asthma (Table 2), and those participants exhibited increased mucin concentrations (FIG.

Figure 6:
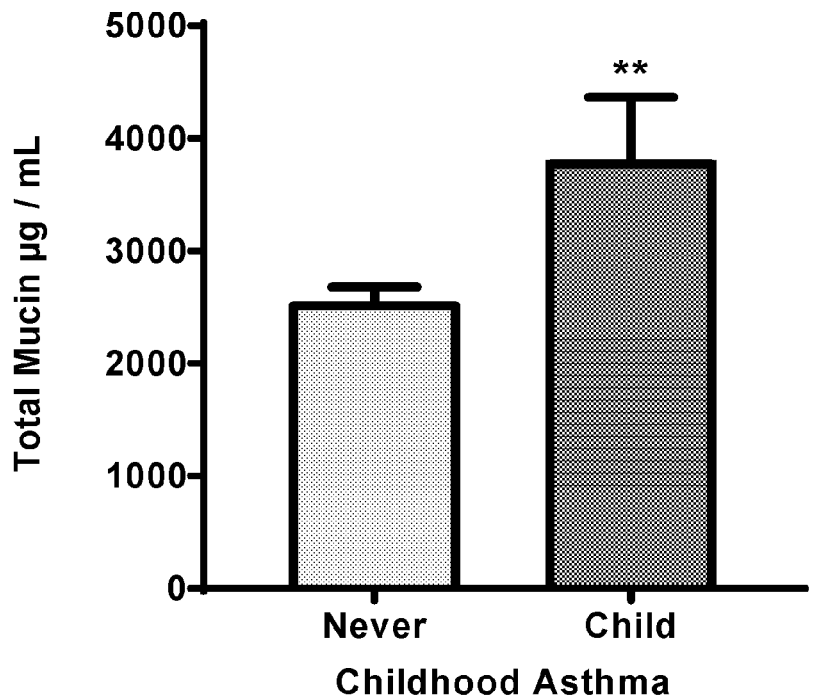
FIG. 6 is a graph showing the relationship between mucin concentrations and patient self-report of childhood asthma. Mucin concentration in participants never diagnosed with asthma (N=389) compared to participants diagnosed with asthma in childhood (N=52, <18 yrs old). Mucin concentrations were significantly higher for childhood asthma. **P value=0.004.

2D). The influence of asthma on mucin concentration was maintained after correcting for cigarette smoking history (P=0.0023). Similar relationships were observed for childhood asthma diagnosis (FIG. 6). Mucin concentrations of the SPIROMICS participants did not exhibit significant associations with asthma biomarkers, including increased sputum eosinophils, blood eosinophils and blood IgE. These findings are consistent with reductions in asthma biomarker predictability in asthma subjects who smoke.

Sensitivity analyses of mucin concentrations based on extremes of concentrations were also performed in ever-smokers, and the correlations were consistent with the analyses shown in FIGS. 1 and 2, Table 6.

Figure 3A:
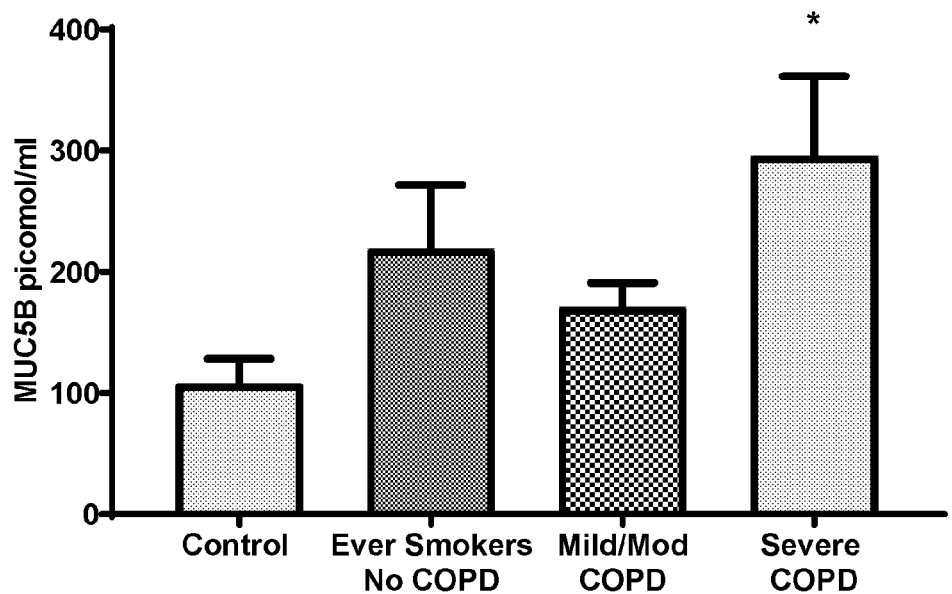
FIGS. 3A-3D are graphs showing the absolute mucin MUC5B and MUC5AC concentrations related to disease severity and smoking history.
Figure 3B:
Figure 3C:
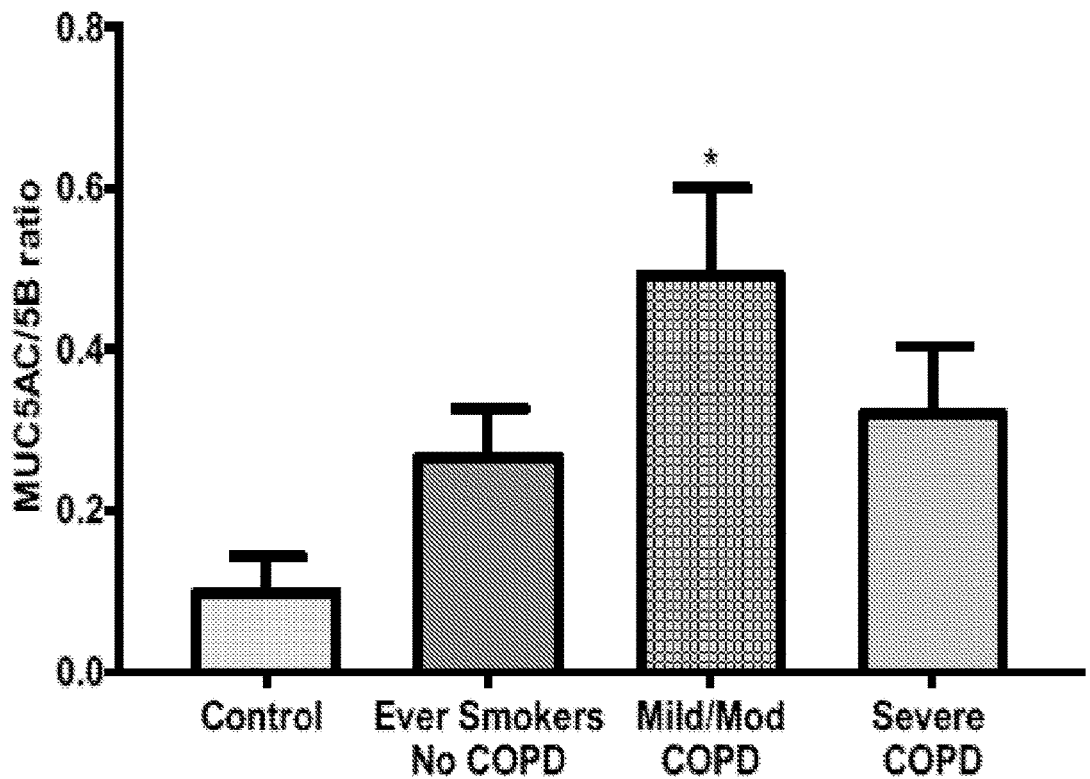

Absolute Concentrations of MUC5B and MUC5AC:

Two observations were evident from the analyses of the relative individual contribution of each of the two secreted airway mucins. First, MUC5B was the dominant secreted mucin in control participants, with concentrations about 10 fold higher than MUC5AC (FIGS. 3A-3B). Second, in disease MUC5B levels rose proportionately (about 3 fold), whereas MUC5AC levels rose disproportionately (>10 fold), with mucin concentration and COPD severity (FIGS. 3A-3B). Accordingly, the MUC5AC/MUC5B ratio was significantly increased in mild/moderate COPD participants, but MUC5B remained the predominant mucin at all levels of disease severity (FIG. 3C).

Figure 3D:
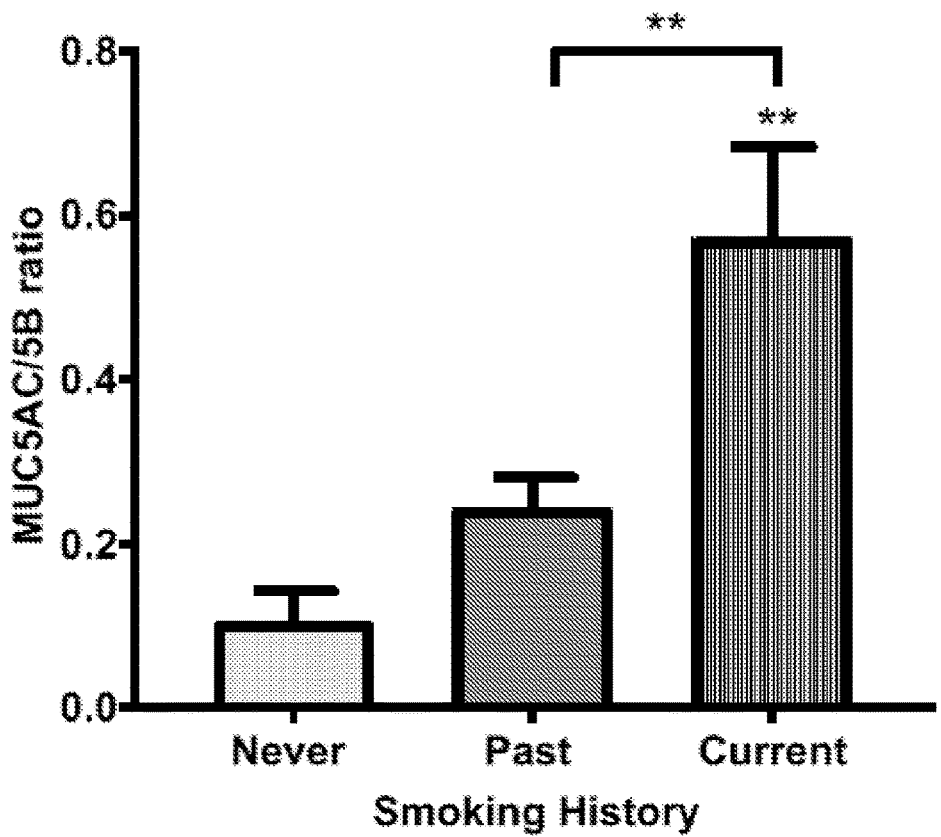
Figure 7A:
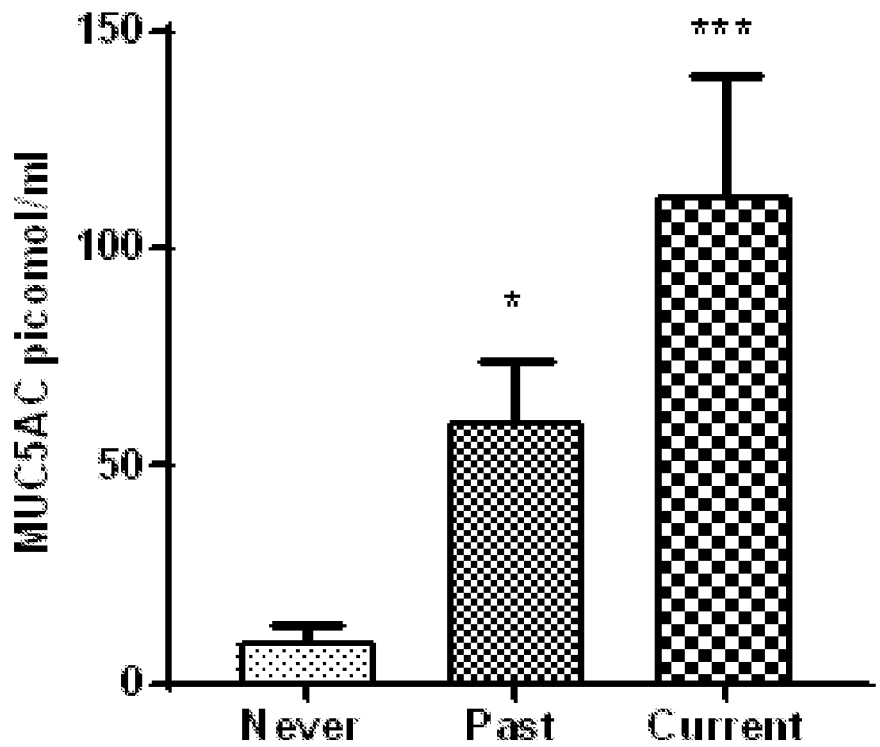
FIGS. 7A-7C are graphs showing the relationship of MUC5AC and MUC5AC/MUC5B ratios to smoking history with asthma subjects removed and MUC5AC concentration to asthma status.
Figure 7B:
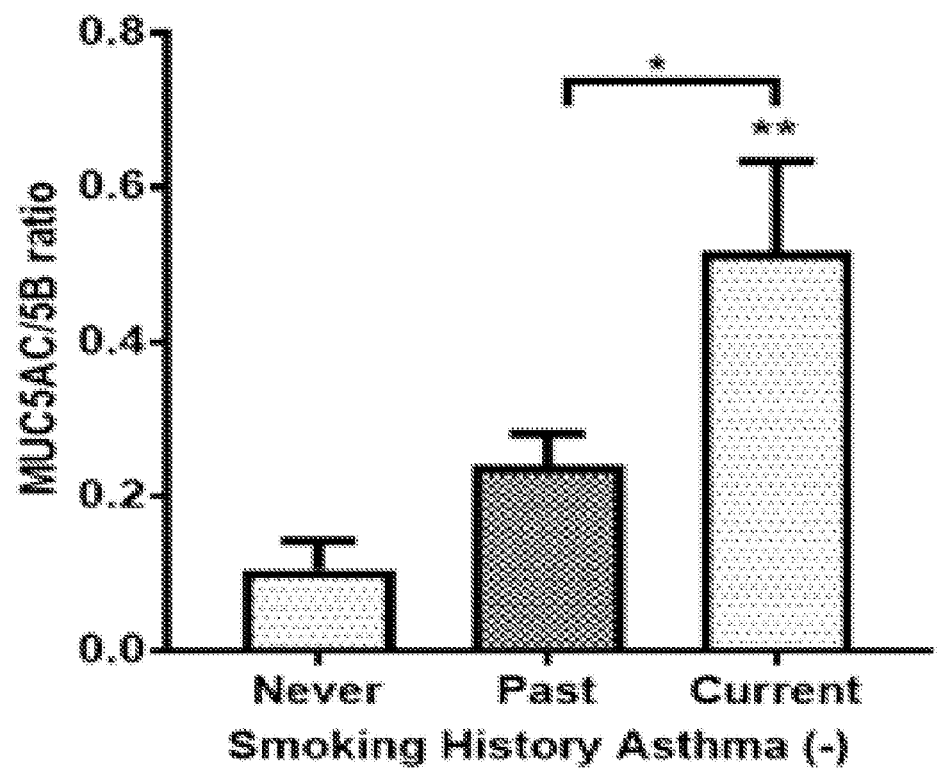
Figure 7C:
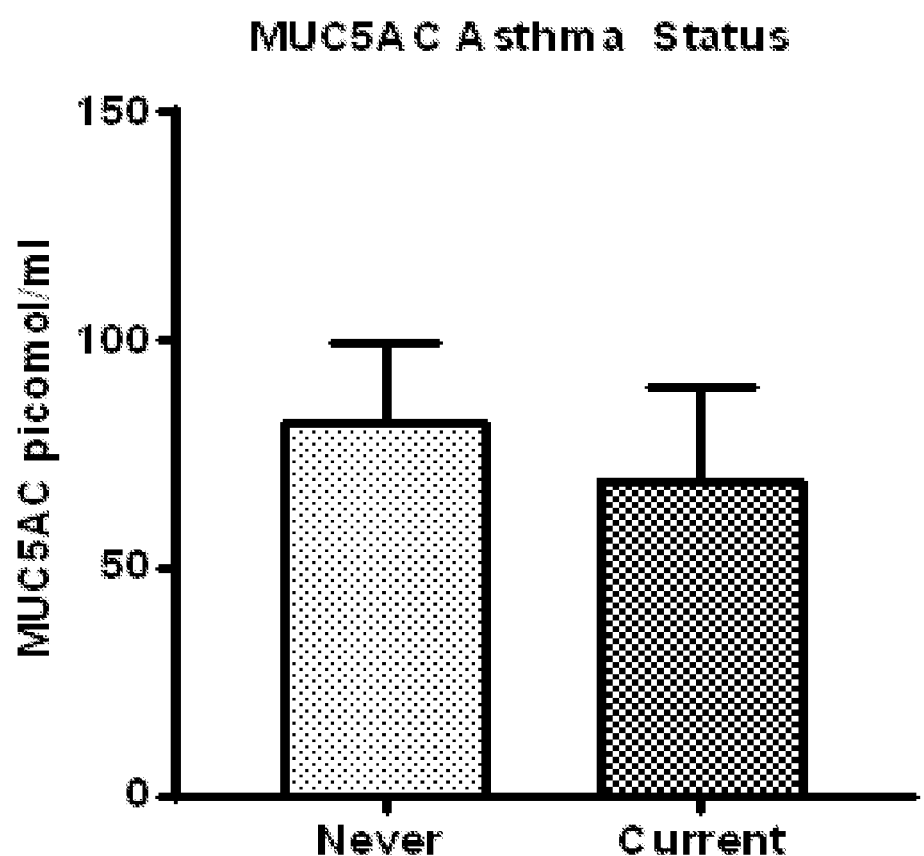

Relationships Between Sputum MUC5AC Concentrations, Cigarette Smoking and Asthma:

To assess whether MUC5AC may be a biomarker for asthma within a cigarette smoking/COPD population, i.e., to assist in the definition of asthma-COPD overlap syndrome subjects, relationships between cigarette smoking, asthma, and MUC5AC mucin concentrations were investigated. The absolute concentration of MUC5AC (FIG. 7A) and the ratio of MUC5AC/B were increased with cigarette smoking (FIG. 3D). This association persisted when asthma participants were removed from the analysis (FIG. 7B) and when asthma history was analyzed as a covariate (MUC5AC P value=0.0008, and Ratio P value=0.0004). In contrast, participants with high MUC5AC levels did not exhibit associations with asthma history (FIG. 7C) nor sputum eosinophil or blood IgE levels. Thus, MUC5AC levels did not predict asthma status in this population.

Figure 4A:
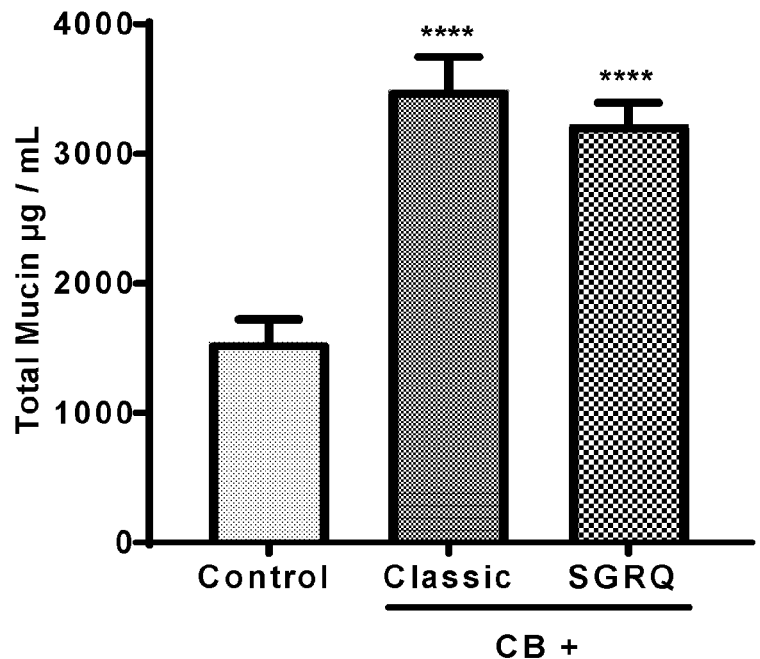
FIGS. 4A-4F are graphs showing the mucin concentration and absolute mucin MUC5B and MUC5AC concentrations related to chronic bronchitis diagnosis and receiver operating characteristics for mucin concentration and chronic bronchitis diagnosis.
Figure 4B:
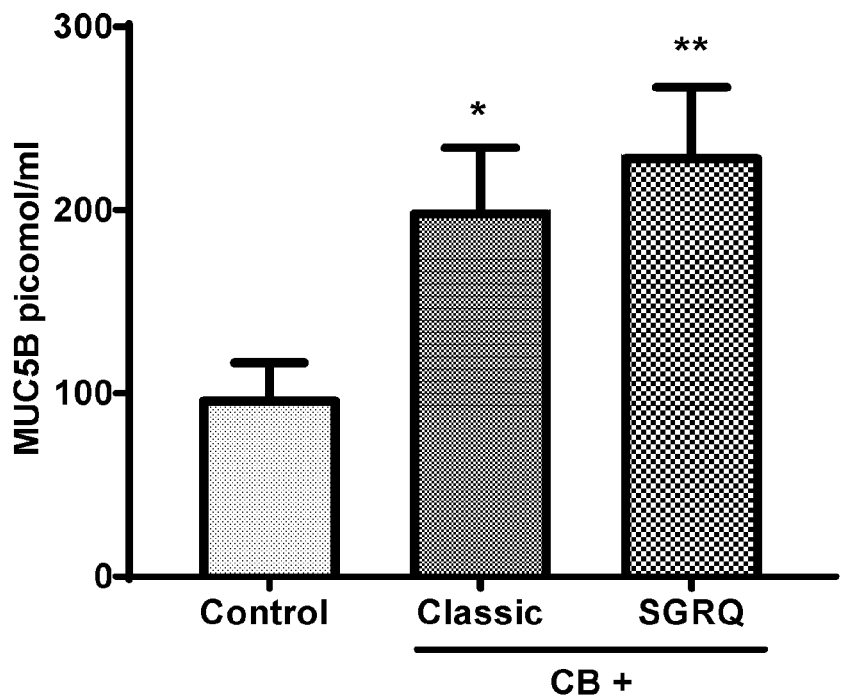
Figure 4C:
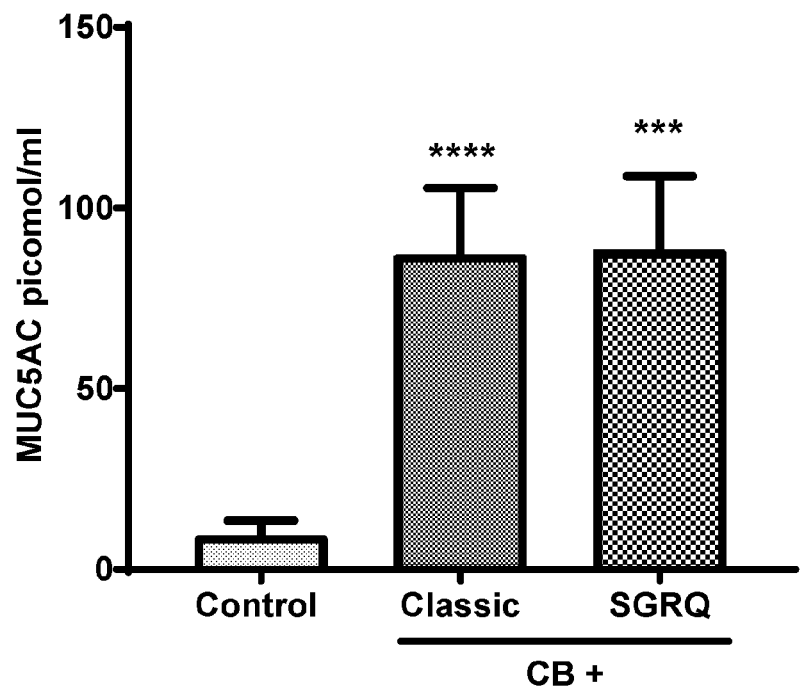

Relationships Between Sputum Total, MUC5B, and MUC5AC Concentrations and the Diagnosis of CB:

The observations suggesting that mucin concentrations are linked to the pathophysiology of chronic bronchitis raised the possibility that mucin concentrations may be a candidate chronic bronchitis biomarker. Accordingly, we tested whether sputum mucin concentrations were raised in participants with classic or SGRQ defined chronic bronchitis and observed significant associations with both definitions (FIG. 4A). Like mucin concentrations, both raised MUC5B and MUC5AC concentrations were also associated with classic and SGRQ defined chronic bronchitis (FIGS. 4B-C).

Figure 4D:
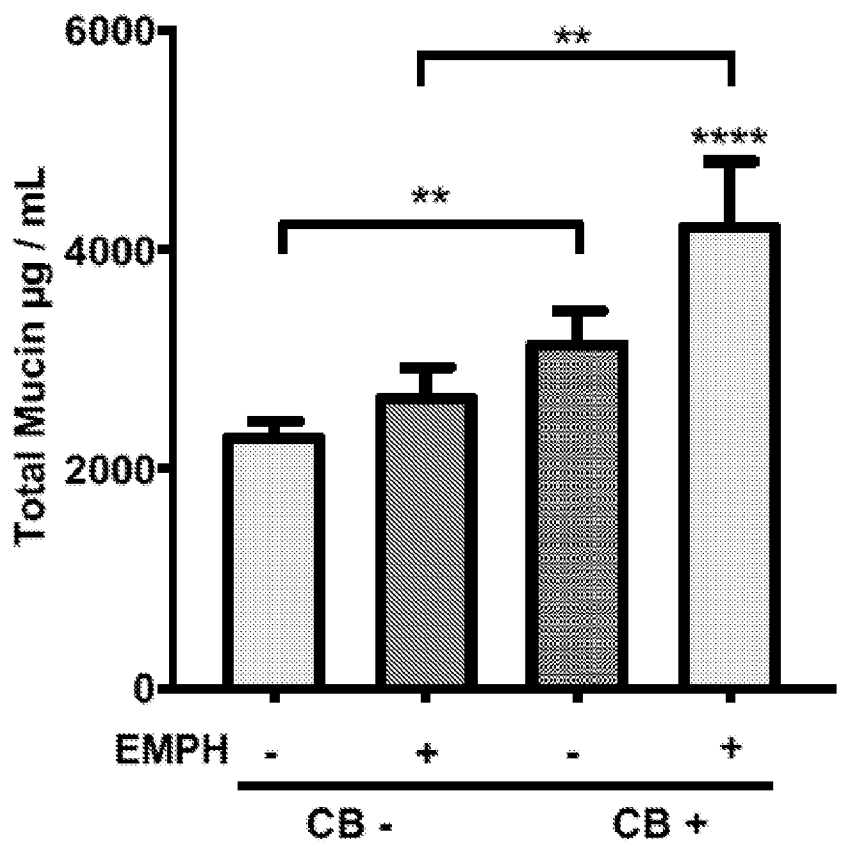
Figure 4E:
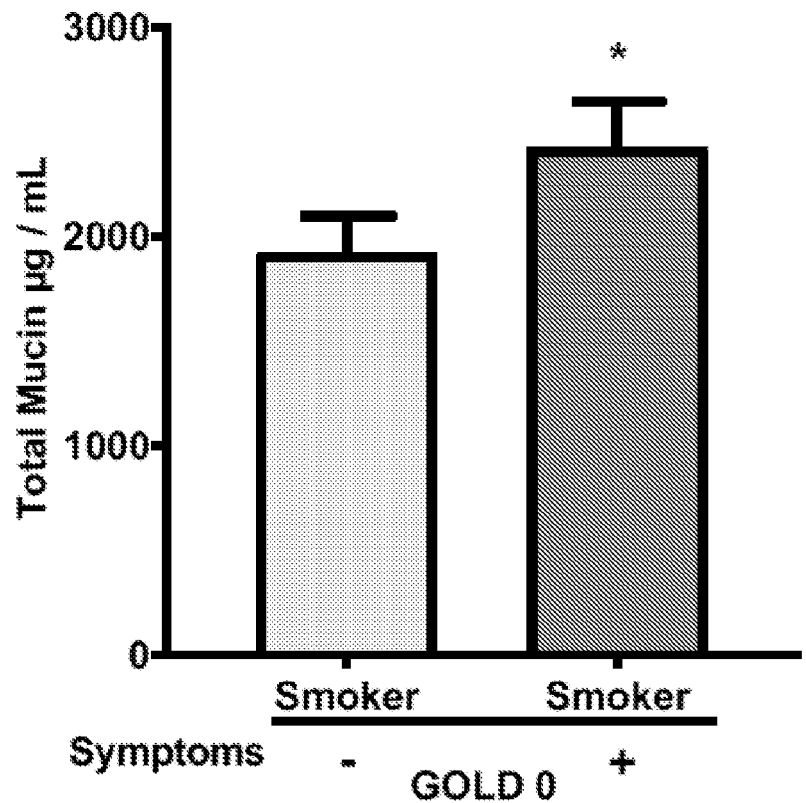
Figure 8A:
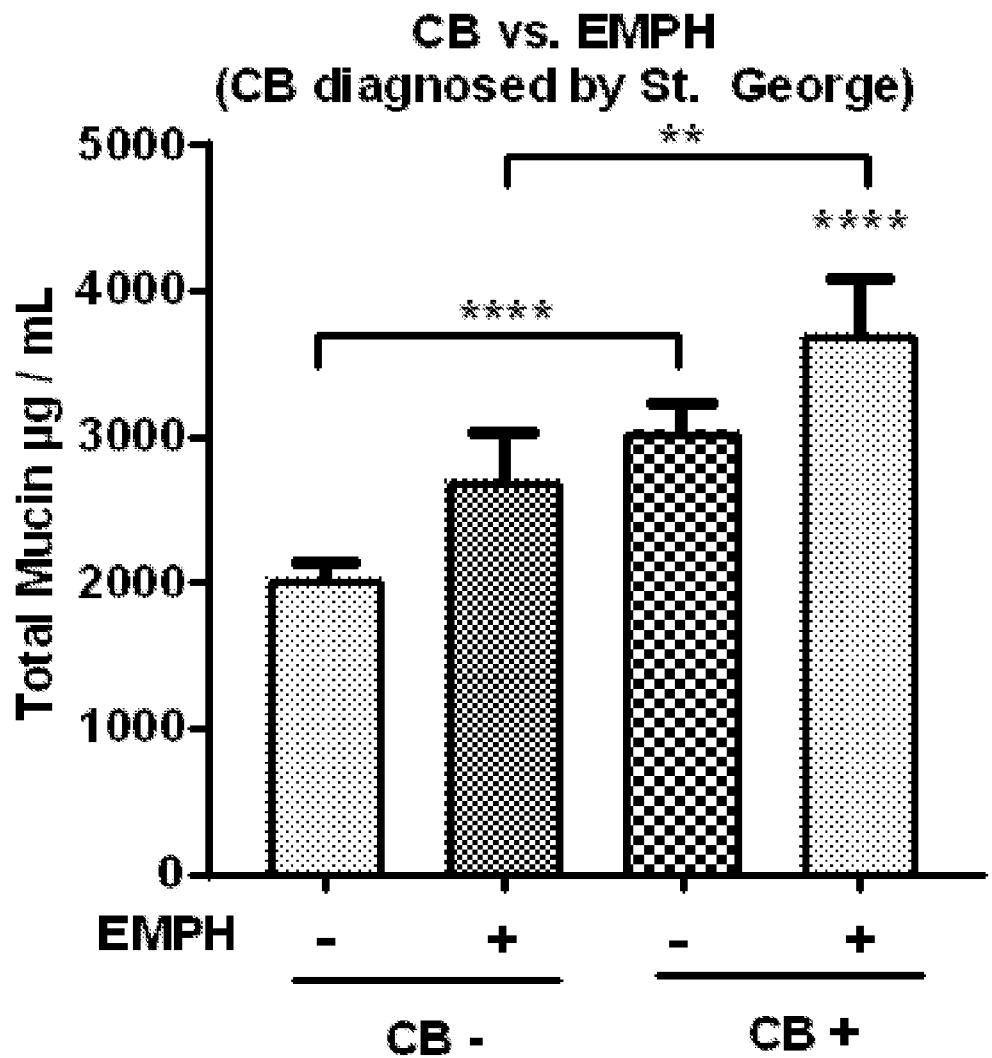
FIGS. 8A-8B are graphs showing the mucin concentration relationship to chronic bronchitis and emphysema using the St. George Questionnaire definition of chronic bronchitis.
Figure 8B:
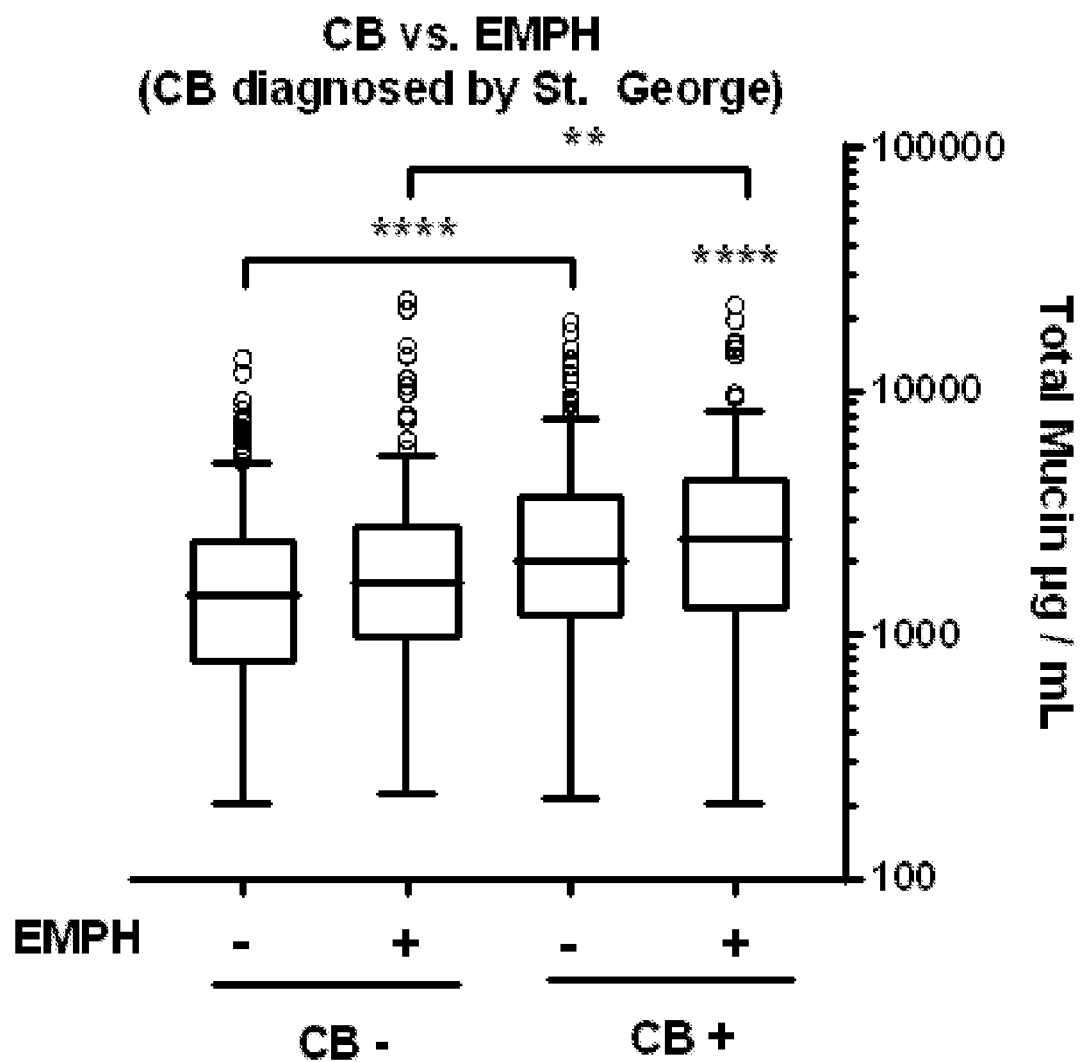

The association between sputum mucin concentration and chronic bronchitis diagnosis were tested in two additional analyses. First, based on the observations that mucins are produced by airways, not alveoli, we tested the hypothesis that the chronic bronchitis rather than the emphysema component of COPD dominated sputum mucin concentration. Utilizing data from ever-smokers, chronic bronchitis positive (classic or SGRQ defined) participants, with or without CT-defined emphysema, exhibited higher mucin concentrations than chronic bronchitis-negative participants with or without emphysema, respectively (FIG. 4D and FIGS. 8A-8B). Second, a recent study reported that symptoms, including phlegm production, in smokers with normal spirometry identified a population with a chronic bronchitis-like phenotype, e.g., increased respiratory exacerbations and activity limitations. Higher mucin concentrations were associated with spirometrically normal ever-smokers participants with symptoms compared to those without symptoms (FIG. 4E).

Figure 4F:
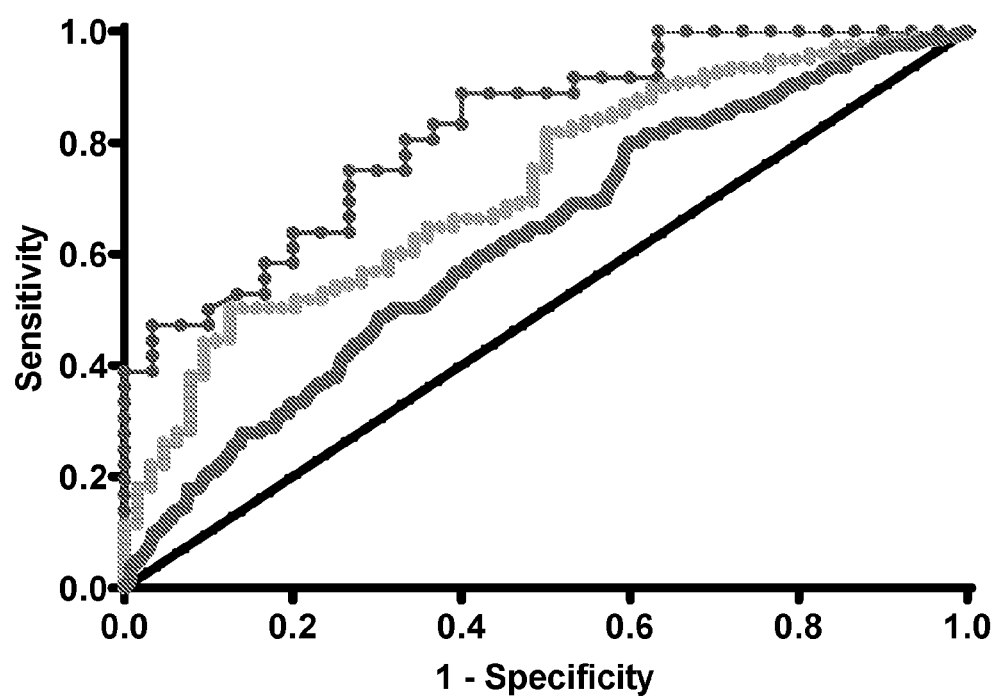
Figure 11:
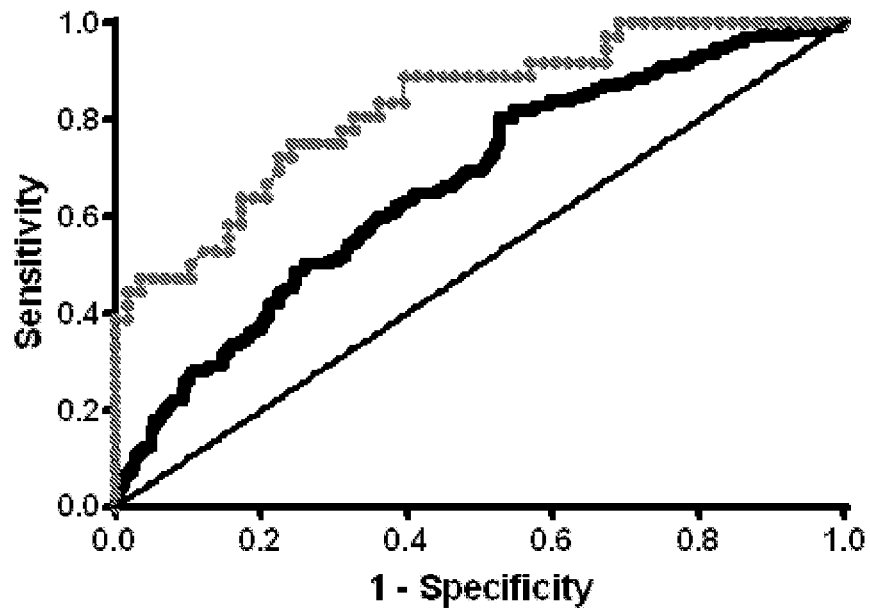
FIG. 11 is a graph showing the receiver operating curves for mucin concentration as related to chronic bronchitis. Here, the panel shows receiver-operating-characteristics curves for mucin concentration in CB positive subjects diagnosed with the classic questionnaire, compared to the never-smoker controls and ever-smokers without airflow obstruction in the SPIROMICS cohort (Black, area under the curve=0.666 [0.6182 to 0.7137]) and in the independent study (Grey, AUC=0.8271 [0.7428 to 0.9115]).

Finally, the sensitivity and specificity of sputum mucin concentration as a biomarker for chronic bronchitis was explored utilizing receiver operating curves (ROC) in both the SPIROMICS and independent cohorts. Utilizing healthy and classic chronic bronchitis SPIROMICS participant data as shown in FIG. 4A, the area under the curve for total sputum mucin concentrations versus classic chronic bronchitis diagnosis was 0.72 (FIG. 4F). The area under the curve for equivalent participant populations in the independent cohort was 0.82 (FIG. 4F). Similar relationships were observed when smokers without symptom defined chronic bronchitis were included in the analyses (FIG. 11). ROC analyses were also performed on the entire spectrum of SPIROMICS participants (area under the curve=0.62, FIG. 4F). Receiver operating curves for mucin concentration and sputum neutrophil counts as related to chronic bronchitis diagnosis are provided in FIG. 10A-10D.

Example 3

The chronic bronchitis component of COPD is defined symptomatically by chronic mucus production and pathologically by airways inflammation, airways remodeling with mucus cell hyperplasia, and mucus plugging. Clinically, the presence of the chronic bronchitis phenotype is associated with accelerated loss of lung function and increased exacerbation frequencies.

The two-gel hypothesis predicts that increased mucin concentration will be the hallmark of the failed mucus transport and intrapulmonary mucus accumulation central to chronic bronchitis pathogenesis. This hypothesis posits that there are two hydrogels on the airway surface that compete for hydration as a function of their mucin concentration-dependent osmotic pressures. In health, a well-hydrated periciliary layer, populated by membrane tethered mucins and other glycoconjugates, lubricates the transport of the overlying mucus layer comprised of secreted mucins (FIG. 1A). In chronic bronchitis, the concentration of the mobile mucus layer increases, reflecting increases in mucin secretion and/or reduced airway surface hydration. Note, the mucus layer osmotic pressures scale to the third power of mucin concentration, making the system sensitive to modest (2-3 fold) increases in mucin concentration. When the mucus layer concentrations and osmotic pressures exceed those of the periciliary layer, i.e., the threshold value, the mucus layer compresses the cilia/periciliary layer and produces mucus stasis and adhesion. Once mucus stasis occurs, mucus accumulation produces the intraluminal material that is expectorated as sputum with cough. Hence, we predicted that mucin concentration is a parameter underlying the biophysical basis of sputum (phlegm) production and the mucoid (gel-like) properties of chronic bronchitis sputum.

The cross-sectional data from the SPIROMICS cohort are consistent with these predictions (Table 8). Specifically, raised mucin concentrations were associated with both self-reports of sputum/phlegm production and the mucus gel-like (mucoid) properties of the expectorated material. Raised mucin concentrations were also associated with both the classic and SGRQ definitions of chronic bronchitis, consistent with the inclusion of sputum/phlegm production in these definitions. Raised mucin concentrations were also associated with the patient population with symptom-based (including phlegm) evidence of airway disease in the absence of spirometrically-defined airway obstruction.

The adherent intra-pulmonary mucus not clearable by cough is predicted to contribute to airflow obstruction and exacerbation frequency in chronic bronchitis (FIG. 1A). Increases in GOLD-status defined airflow obstruction were observed as a function of increased mucin concentrations in SPIROMICS participants. Because exacerbation frequency appears to drive the loss of lung function in COPD, the relationship between mucin concentrations and the frequency of prospective exacerbations was also investigated. Raised mucin concentrations were associated with both increased total exacerbation rates and exacerbations requiring interactions with health care systems.

The SPIROMICS cross-sectional sputum analysis allows testing of associations, but not mechanistic links, between mucin concentration and disease pathogenesis/severity. It should be noted that previous studies of COPD participants related an increase in mucus concentration to reductions in mucociliary clearance, as predicted by the two-gel model. The hypothesis that mucin concentration drives chronic bronchitis pathogenesis is also consistent with animal model data, which have demonstrated that dehydration of airway surfaces, with concomitant mucin hyperconcentration, produced the pathology of COPD-like lung disease in mice. Consequently, we postulate that increased mucin concentration may quantitate the severity of a disease causing pathway in COPD.

The SPIROMICS data showed that both cigarette smoking history and self-report asthma history were associated with raised mucin concentrations, consistent with previous in vitro, animal model, and clinical reports. The observation that a history of asthma was associated with increased mucin concentrations suggests that mucin concentration may be a final common pathway associated with the worsened outcome of patients with asthma-COPD overlap syndrome (ACOS).

With respect to the relative contributions of the two secreted mucins to disease pathogenesis, the increase in MUC5B as a function of COPD disease severity is consistent with previous reports of the MUCSB pre-dominance in COPD. However, the disproportionate increase in MUC5AC levels as a function of disease severity was striking. Interestingly, the rise in MUC5AC levels was dominated by associations with cigarette smoking status rather than asthma history or asthma biomarkers, suggesting that MUC5AC levels may not help define ACOS in this population. These data also suggest that rates of MUC5AC secretion in most SPIROMICS participants was regulated by cigarette smoke-triggered pathways directly and/or indirectly via IL1α/β, IL17, and/or EGF-R, rather than asthma-dominant Th2 pathways.

Figure 9:
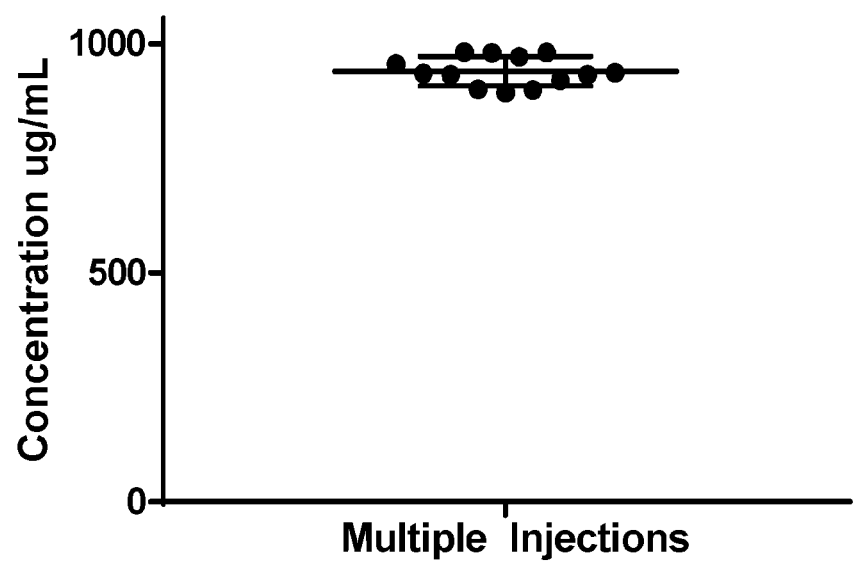
FIG. 9 is a graph showing the coefficient of variation for mucin measurements. To test the reliability of our measurement technique, we injected 13 samples consecutively from the same mucin standard solution curated in the lab. The CV=3.4%. The solid line represents the mean mucin concentration=940 µg/mL. The dotted line represents two standard deviations above and below the mean.
Figure 10A:
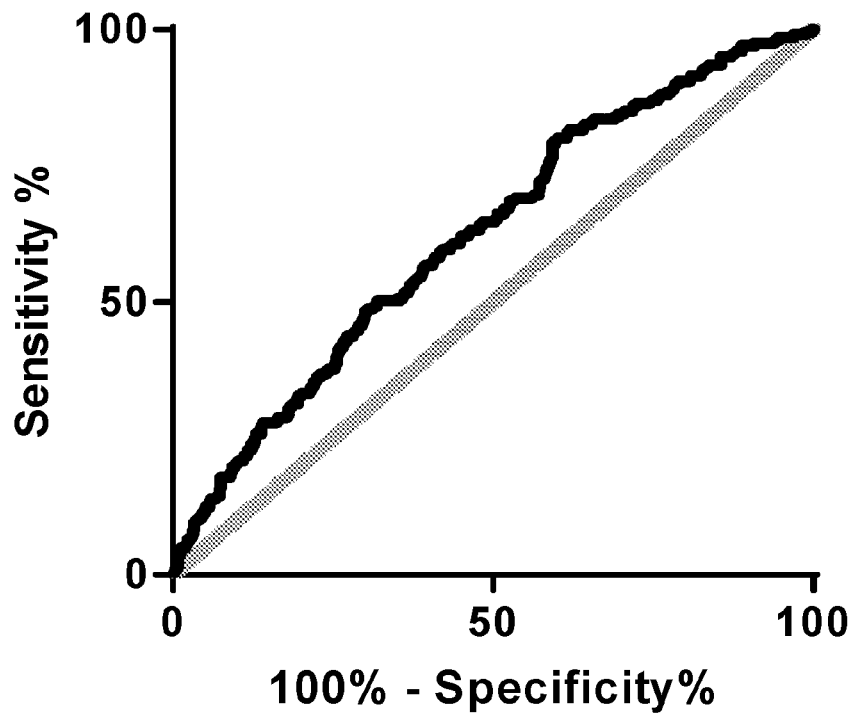
FIGS. 10A-10D are graphs showing the receiver operating curves for mucin concentration and sputum neutrophil counts as related to chronic bronchitis diagnosis.
Figure 10B:
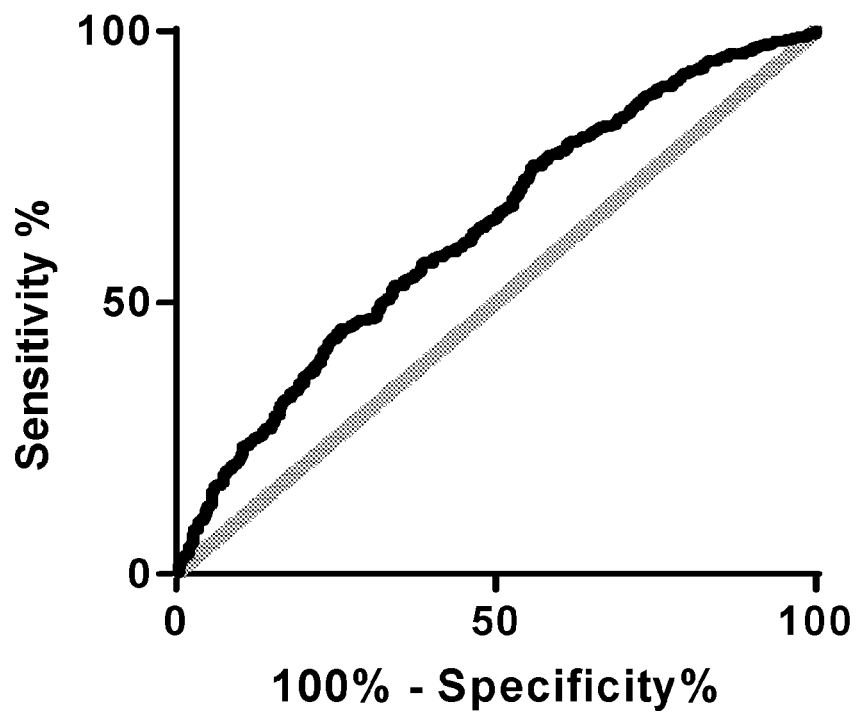
Figure 10C:
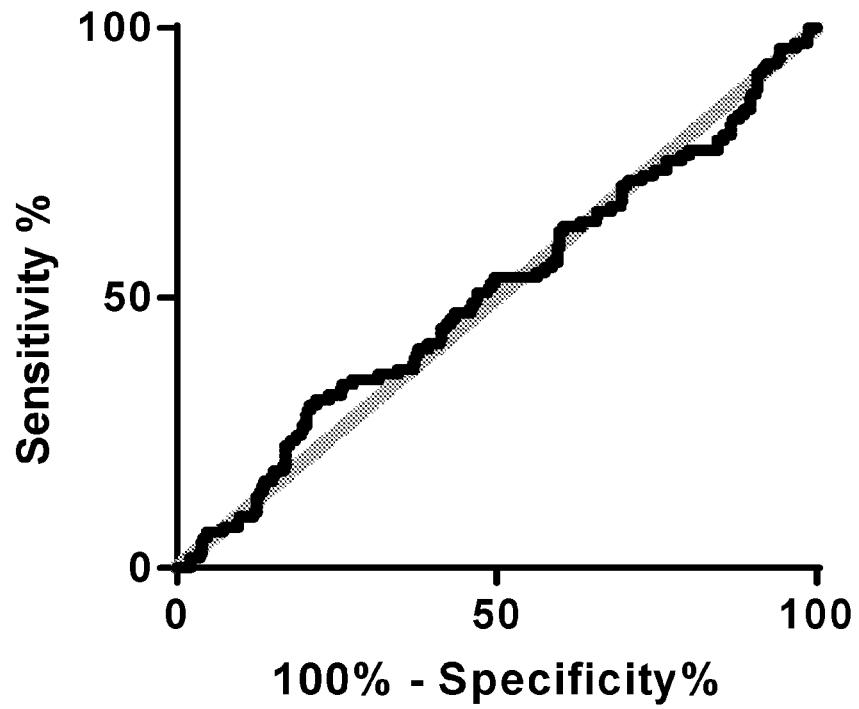
Figure 10D:
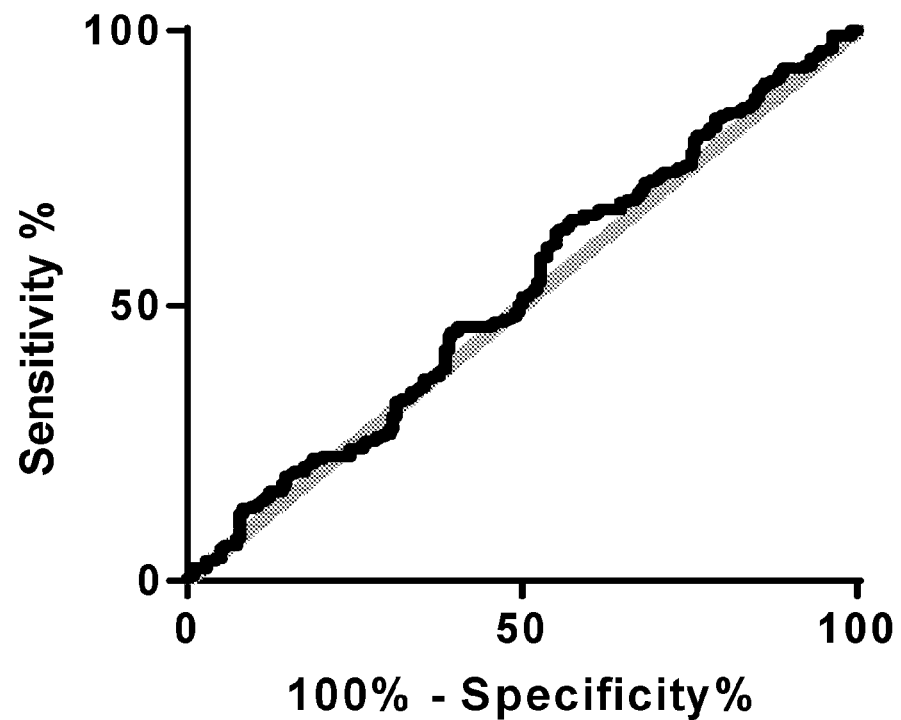

There are inherent limitations to large scale studies of sputum. First, collection of sputum in all study participants is challenging. Sputum induction was performed to maximize the likelihood of generating samples. The acceptance, safety, and efficacy of sputum induction were high, but the cost was an increment in study visit time. Second, saliva contains low and variable MUC5B, but not MUC5AC, and inevitably contaminates expectorated lower airway samples. Because there are no validated screening criteria for salivary contamination of biochemical analyses, we assessed salivary contamination with salivary amylase measurements in a randomly selected subset. Contamination was observed, was modest, and importantly, was equally distributed amongst the strata, suggesting it did not bias our results. Finally, substantial variability in mucin concentration measurements was observed. Because the technical variance of the measurement was low (FIG. 9) and the physical measurement of mucin concentration avoids the artifacts of immunologic methods, biologic or collection based sputum sample variability per se likely dominated this observation.

The associations between mucin concentrations and chronic bronchitis pathogenesis raised the question of the diagnostic utility of this metric as a quantitative biomarker for chronic bronchitis. In the SPIROMICS cohort, total sputum mucin concentrations were associated with both classic and SGRQ questionnaire based diagnosis of chronic bronchitis. The ROC curves for mucin concentration and SPIROMICS participants with patient reported outcome (PRO) based chronic bronchitis diagnosis versus control subjects (FIG. 4A) yielded a "fair" outcome (AUC=0.72). A similar analysis performed in an independent, single site cohort provided a "good" outcome (AUC=0.82). The congruence of ROC outcomes argues for the potential utility of this measure, but the lower area under the curve for the SPIROMICS participants suggests that variability introduced in multi-site studies might be significant. When ROC analyses were applied to the entire SPIROMICS cohort, i.e. including ever-smokers with or without PRO based diagnosis of chronic bronchitis, the area under the curve was "poor" (0.62). Part of this poorer performance may be related to the known variability in chronic bronchitis self-reported diagnosis, which was also observed in a SPIROMICS Repeatability sub-study in which classic chronic bronchitis repeatability over a 4-6 week interval was 0.61 (Kappa score).

Finally, our results have implications for therapy of the chronic bronchitis component of COPD. Our data demonstrate the increases in mucin concentrations were associated with cigarette smoke exposure and asthma, suggesting that targeting upstream components of these pathways to inhibit MUC5B and MUC5AC expression may be useful. Similarly, the reports that acute exposure to hypertonic saline diluted mucin concentrations and accelerated mucus clearance in chronic bronchitis participants suggest therapies designed to hydrate airway surfaces and reduce mucin concentrations may also be effective. Importantly, airway mucin concentrations may serve as a relevant biomarker for the development of such novel chronic bronchitis therapeutics.

Example 4

Subjects and Material:

Induced sputum was collected from 883 subjects at 11 SPIROMICS clinical centers according to the protocol and ATS/ERS standards. All patients gave written informed consent. Sputum induction was performed in patients with a screening visit FEV>35% predicted. Induced sputum samples were placed in 6M guanidine extraction buffer, shipped to the SPIROMICS Biospecimen Processing Center, and stored at −4 C.

Figure 12:
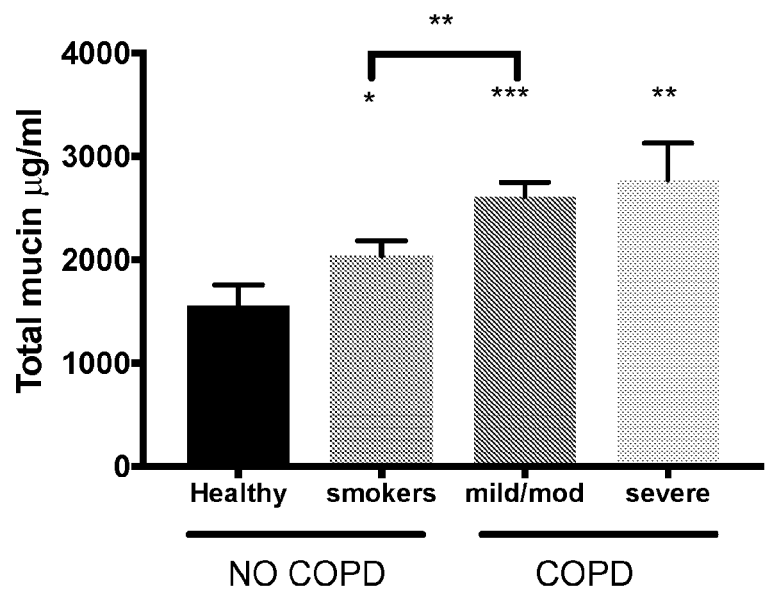
FIG. 12 is a graph showing sputum mucin concentrations in smokers and nonsmokers not diagnosed with COPD, in subjects diagnosed with mild or moderate (mild/mod) COPD, and those diagnosed with severe COPD.

Sputum Mucin Concentrations Tract Smoking Status and CB Severity:

Diluted sputum samples (10-50 times) were subjected to SEC-MALLS/dRI mucin concentration measurements. Aliquots were injected into size exclusion columns to separate mucins from other proteins and effluents passed through an in-line enhanced optimal system laser photometer (HE-LEOS-II; Wyatt Technology) coupled to T-rEx refractometer (Wyatt). Data were analyzed using Astra (v6.1.1.7, Wyatt). Mucin concentrations were associated with smoking status and disease severity of COPD as indexed by the spirometric evaluation classification (FIG. 12, Table 9)

Individual MUC5AC Concentration and MUC5B Concentration and their Ratio in Sputum Tract Smoking Status and CB Severity:

A Mass Spectrometry Parallel Reaction Monitoring (PRM) labeled mucin quantitation technique was used to quantitate MUC5B and MUC5AC mucins. Briefly, 50 μl from each sputum sample was reduced, alkylated and digested with trypsin. Six heavy labeled peptide internal standards from MUC5B and MUC5AC were spiked into sputum digests at final concentrations of 100 fmol/μL. Samples were subjected to tSIM-DIA analysis using hybrid quadrupole Orbitrap mass spectrometer with a Nano spray source (Q-Exactive™, Thermo).

Figure 13:
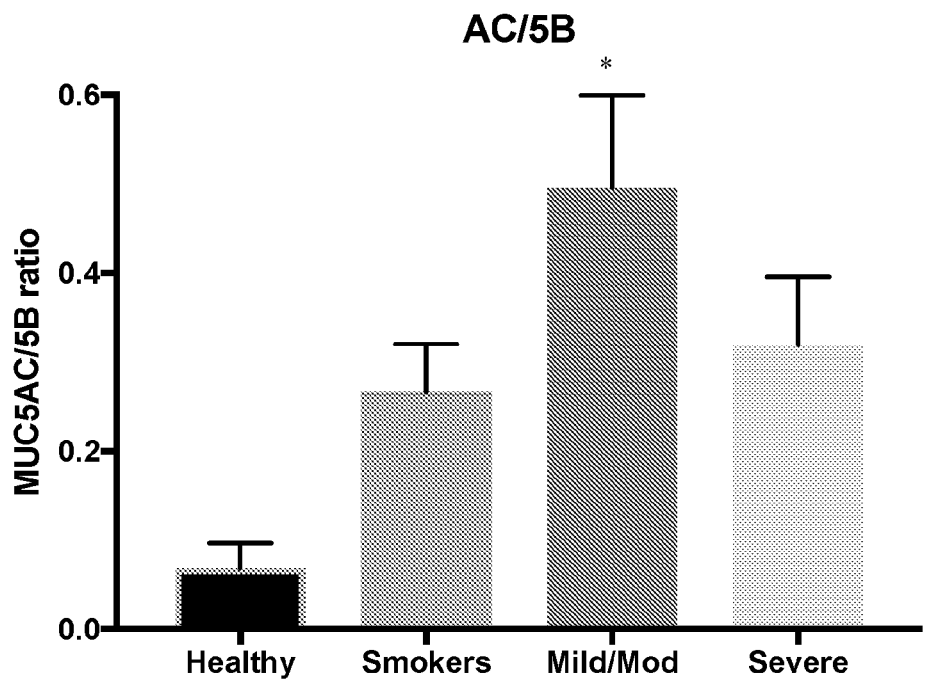
FIG. 13 is a graph showing the ratio of MUC5AC and MUC5B levels in sputum samples from healthy subjects, smokers, subjects having mild or moderate COPD, and those having severe COPD. subjects. MUC5AC levels and MUC5B levels were quantitated using a mass spectrometry parallel reaction monitoring labelled mucin quantitation techniques. *$P=0.05$-0.01.

Multiple observations were evident from the MUC5B and MUC5AC individual concentration data (FIGS. 3A-3B, Table 10). First, similar to mucin concentrations, raised MUC5B and MUC5AC concentrations were associated with increased disease severity of COPD. Second, MUC5B was the dominant secreted mucin in a sputum sample from control subjects, with levels about 10 fold higher than MUC5AC. Third, MUC5B levels increased with disease severity (up to 3 fold) (FIG. 3A). Fourth, MUC5AC levels rose disproportionately (>10 fold) with disease severity. The MUC5AC/MUC5B ratio was significantly increased in mild/moderate COPD (FIGS. 3C-3D, FIG. 13). The MUC5AC/MUC5B ratio was also increased in current smokers.

Kesimer Mucin Index:

On the basis of the investigations described herein, the present inventor has developed a unique, novel metric for better and more resolved diagnosis of bronchitis and the smoking status. Using the combination of mucin concentrations of the same individuals and the ratio of individual mucin concentrations, MUC5AC/5B gives us much better and resolved quantitative metric, that is called Kesimer mucin index (KMi), or Kesimer MUCQuant index (KMQuant index or KMQi) (MUCQ score or MUCQ index), the formula being the following:

KMQuant index=(Mucin concentration (microgram/ml))×the ratio of MUC5AC/MUC5B)÷100

Figure 14:
FIG. 14 is a graph showing the use of a mucin index (i.e., Kesimer MUCQuant Index (KMQuant index)) to track smoking status and severity of CB. The KMQuant index provides better resolution than mucin levels (FIG. 12) and or MUC5AC levels (FIGS. 13A-13C). *$P=0.05$-0.01, **$P=0.001$-0.0099

As shown in FIG. 14 and Table 11) the KMQi is associated with increased disease severity of COPD with much better resolving power of diagnostic metric than mucin concentration and the concentration of each of the individual mucins alone. The index is about 10 fold higher in smokers, and 20 fold higher in midl/moderate COPD comparing to healthy non-smokers.

Example 5

Airways' Macin Index, MUCQuant and MUCQuant Plus (+): An Objective Diagnostic and Prognostic Biological Metric for Muco-Obstructive Respiratory Diseases.

Chronic lung diseases, characterized by airway obstruction, persistent cough, and infection and inflammation, such as chronic bronchitis, bronchiectasis, and asthma altogether affects more than 45 million diagnosed patients and many more who remain undiagnosed or at risk. Although, there has been a longstanding interest in the pathogenesis of these pulmonary diseases, studies relating the changes in the mucus properties (quality and quantity) and clearance to disease pathogenesis are limited. More importantly, currently, there is no objective biological marker to diagnose and/or predict the risk of chronic hyper-secretory, muco-obstructive lung diseases such as chronic obstructive pulmonary disease (COPD), bronchiectasis, and/or asthma. The diagnosis of chronic bronchitis (CB), a component of COPD, currently relies on patient questionnaires to assess cough and phlegm history. Additionally, there is no metric to gauge the risk of developing these lung diseases. A "bronchitic" metric may be used to identify and monitor at-risk populations and provide them the opportunity to modify their behavior and reduce their exposure before the onset and progression of disease. Such behavioral adaptations may allow subjects to enjoy a higher quality of life and reduce the economic burden on the healthcare system.

Our recent observations indicate that both the concentration and the type of mucins, the large gel forming component of mucus, are closely associated with the progression and symptoms of mucoobstructive lung diseases, such as CB, i.e. when they concentrate on the airway surfaces due to airway dehydration it leads to the accumulation of mucus in the lung that produces the chronic airflow infection, airways infection, and phlegm production typical of chronic bronchitic subjects1. We have also demonstrated that mucin concentrations may be utilized as an objective test for chronic bronchitis (Kesimer et al. *N Engl J Med* 377:911-922 (2017)). On the basis of this work, a novel quantitative metric (below) was formularized that combines total airway mucin concentrations and the ratio of the two dominant airway mucins, MUC5AC and MUC5B, into a personalized mucin score, termed MUCQuant or KMQuant (Kesimer MUCQuant) index, which characterized the health/disease status of the airway mucus.

KMQuant: [Mucin]×([MUC5AC]÷[MUC5B])÷100

Figure 15A:
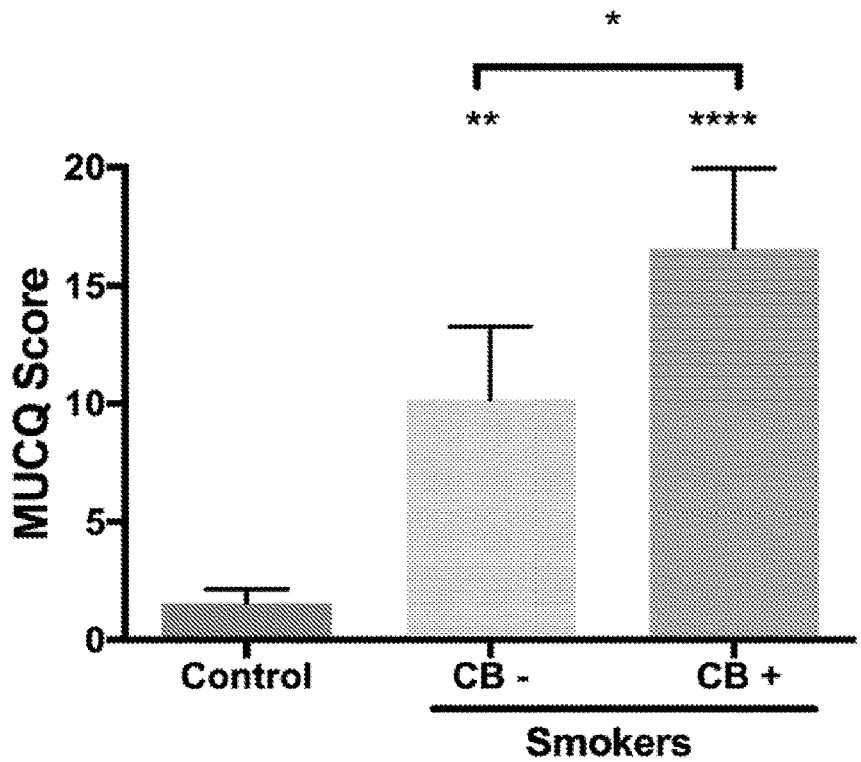
FIGS. 15A-15C show the Kesimer mucin index (MUCQuant) in a COPD cohort. The Kesimer mucin score/index tracks CB symptoms (FIG. 15A), cigarette smoking and pack history (FIG. 15B) and the severity of airway obstruction (FIG. 15C) in the SPIROMICS cohort. TCORS (30+/−2 yo) and SPIROMICS (60+/−5 yo) and the severity of COPD (GOLD 1 and 2). *$P=0.05$-0.01, $P=0.001$-0.0099, *$P=0.0001$-0.00099, ****$P<0.0001$.
Figure 15B:
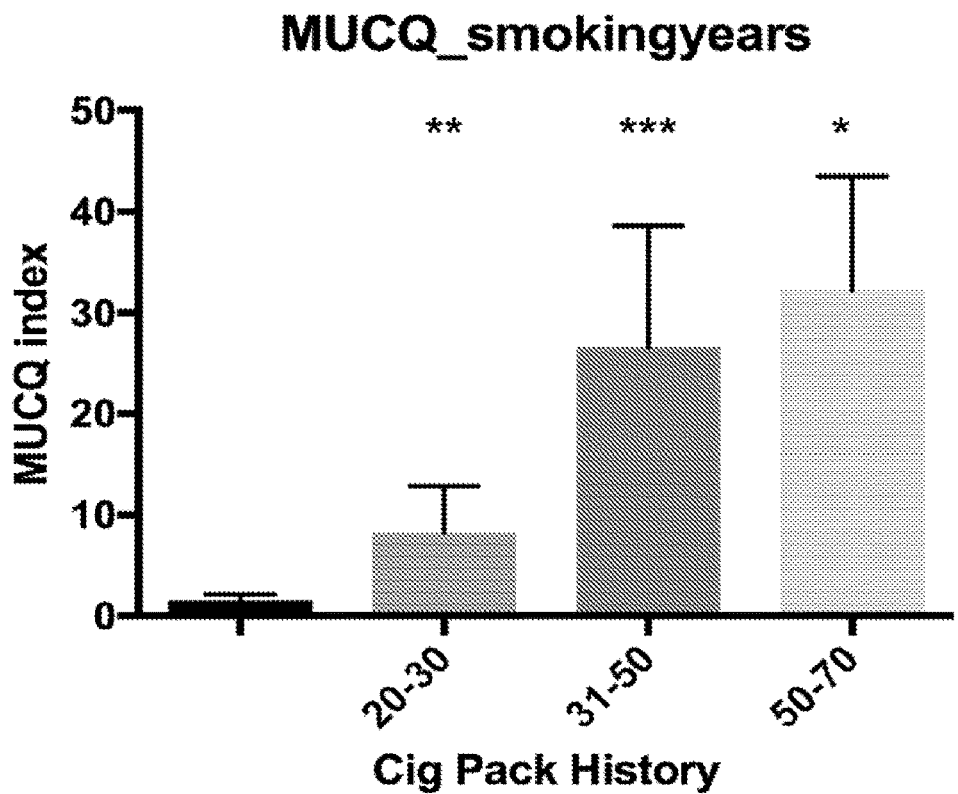
Figure 15C:
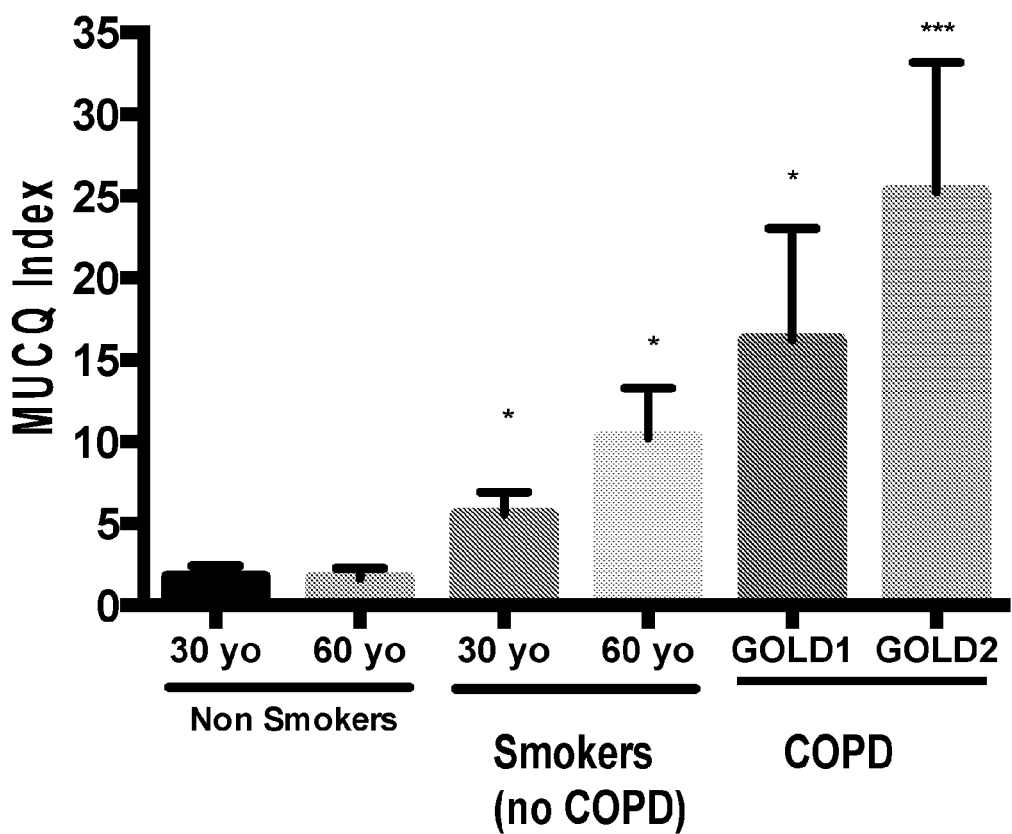
Figure 16:
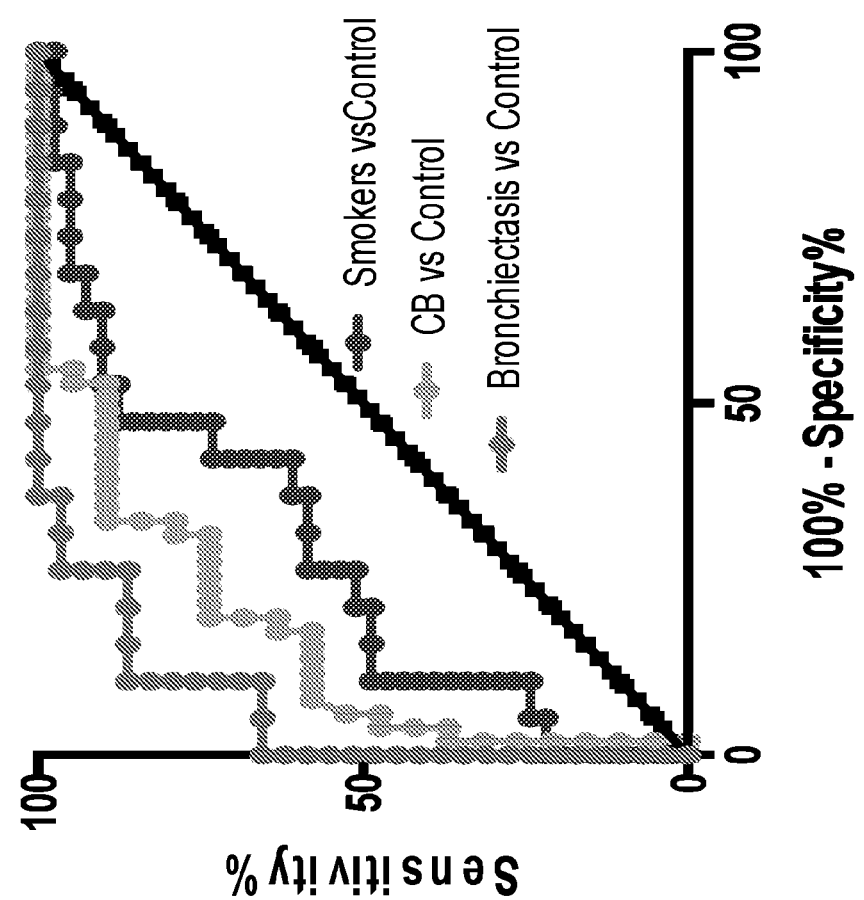
FIG. 16 shows the MUCQuant score and its diagnostic power. Panel A shows mean MUCQ score for never smokers (control, N=19), smokers with no airway disease (N=41), CB (N=51) and non-CF bronchiectasis (N=29). Panel B shows receiver operating characteristics (ROC) curves for MUCQ score for these groups comparing to health controls. Subjects diagnosed with CB (using questionnaires) (Second from the top, area, under the curve, AUC=0.84) and diagnosed with non-CF bronchiectasis (using history, symptoms and chest CT) (Top, AUC=0.94) and smokers with no-disease compared to healthy controls (third from the top, AUC=0.73). *$P=0.05$-0.01, $P=0.001$-0.0099, *$P=0.0001$-0.00099, ****$P<0.0001$.
Figure 16:
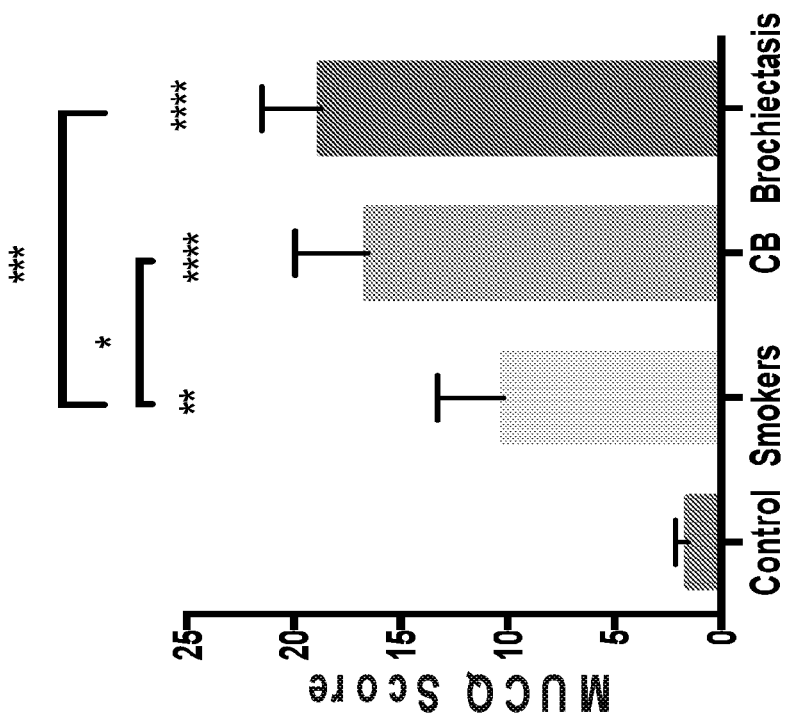

Applying this novel mucin metric to the data obtained from our previous study, we realized that this metric provides superior, quantitative, personalized snapshot of the lung in health and disease in comparison to the total and individual mucin concentrations alone. Our current data clearly indicates that the mean MUCQuant score can differentiate between diverse chronic lung diseases and could potentially function as a categorical disease specific marker (FIGS. 15A-15C, FIG. 16 and Table 12). Specifically, FIGS. 15A-15C show the Kesimer mucin index (MUCQuant) in a COPD cohort. The Kesimer mucin score/index tracks CB symptoms (FIG. 15A), cigarette smoking and pack history (FIG. 15B) and the severity of airway obstruction (FIG. 15C) in the SPIROMICS cohort. MUCQ score can also predict the risk of cigarette smoking and differentially indicate the risk between younger (30+/−2 years old) and older (60+/−5 years old) smokers with no disease in two independent cohorts. FIG. 16 shows the MUCQuant score and its diagnostic power. Table 1 provides MUCQuant and MUCQuant plus score in health and muco-obstructive lung diseases.

Moreover, preliminary observations indicated that in response to different stimulus, e.g., type 1, type2 and type 17, allergic individuals have categorically distinct responses to these different immunological allergic conditions. For instance, bactericidal/permeability-increasing fold-containing family member A1 (BPIFA1 (or SPLUNC1)) dramatically decreases, while IgGFc-binding proteins (FCGBP) increase significantly in allergic asthma type$^2$ (IL13) response.

Figure 17A:
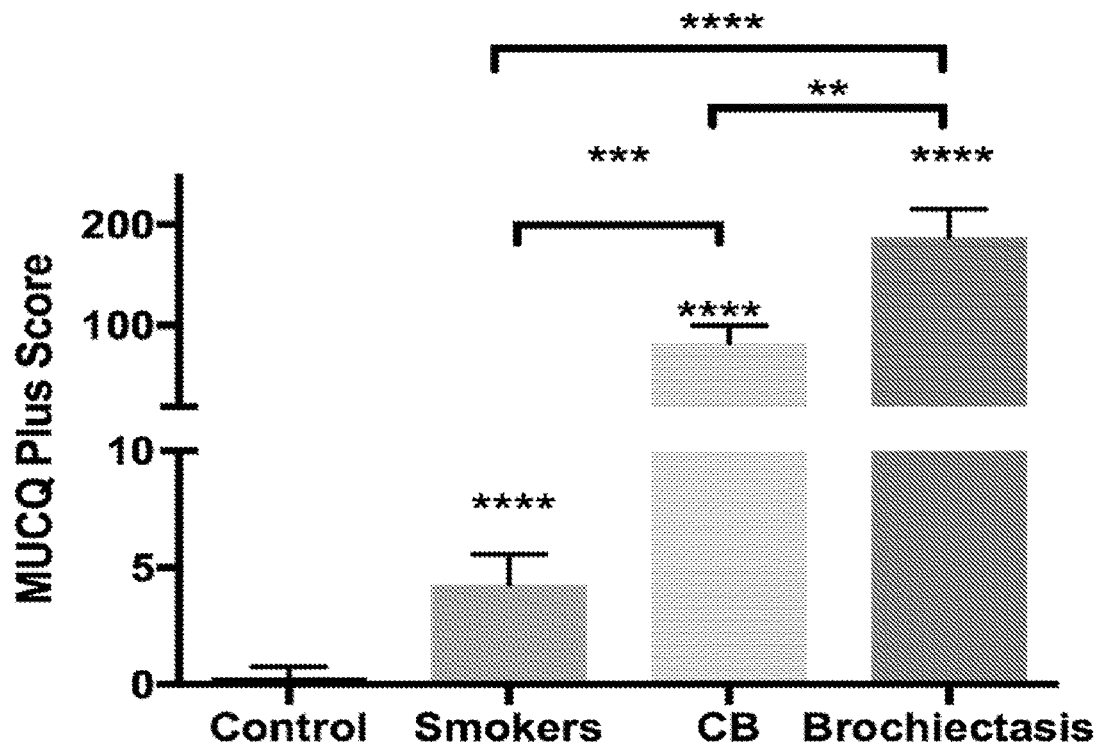
FIGS. 17A-17B shows MUCQuant Plus scores and their diagnostic power.
Figure 17B:
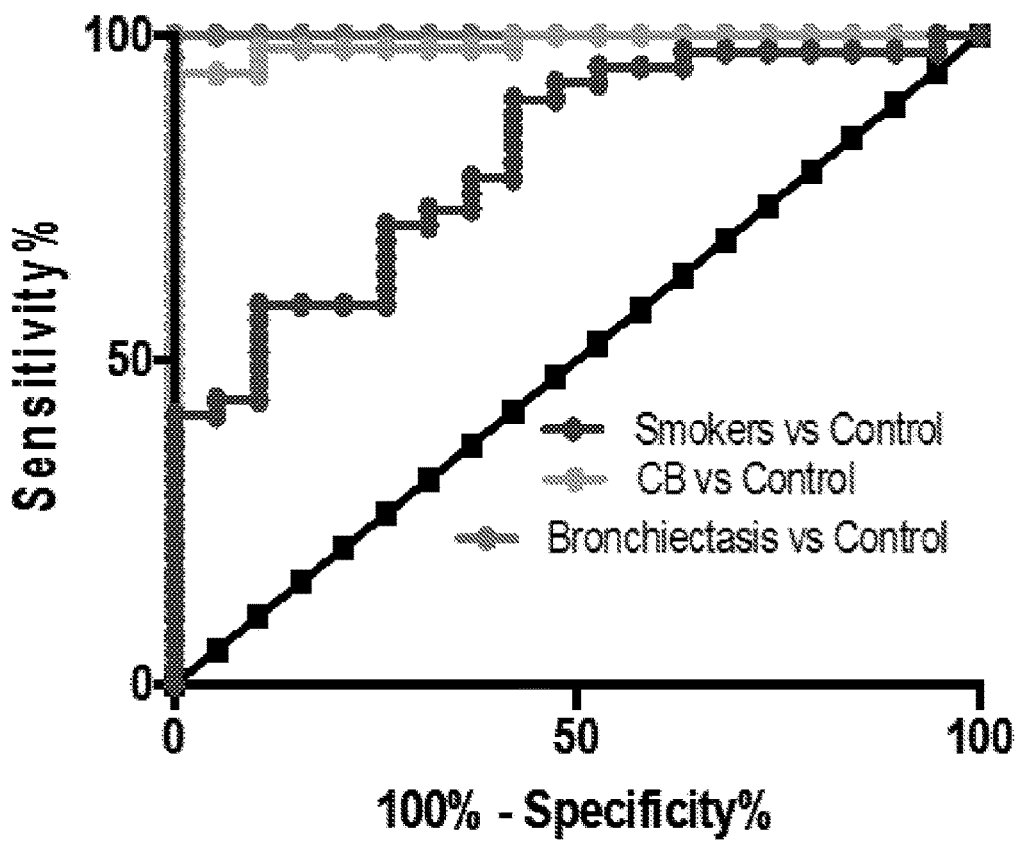

We found that the ratio of these two proteins characteristically reflects the pathogenetic disease specific background in the airways. For instance, the ratio of FCGBP/SPLUNC1 is under 0.1 in healthy individuals and is 0.5 in smokers and increases dramatically with the muco-obstructive, chronic inflammatory, and allergic-asthmatic diseases. The ratio is approximately 5 in COPD and type 1 inflammation such as bronchitis and PCD. The ratio is approximately 10 in non-CF bronchiectasis and dramatically increases to 20 in type 2 inflammations, e.g., in asthma challenges (Table 12). Accordingly, we integrated the ratio of the concentration of these two proteins into our metric and named it the MUCQuant Plus (+) index or score or the Kesimer MUCQuant+ index or score (KMQuant+) (FIGS. 17A-17B and Table 12).

$$KMQuant+=[mucin]\times([MUC5AC]+[MUC5B])+100\times(FCGBP \div SPLUNC1).$$

The associations between MUCQuant and MUCQuant+ indices and the pathogenesis of hypersecretory lung diseases suggests that these indices could operate as quantitative biomarker indexes for both differential diagnosis and prognosis. The ROC curves for the MUCQuant index with questionnaire based diagnosis versus control subjects yielded a "fair" outcome (AUC=0.72) for smokers, a "good" outcome (AUC=0.84) for CB, and an "excellent" outcome (AUC=0.94) for non-CF bronchiectasis (FIG. 16).

The ROC curves for MUCQuant+ index revealed a further improved diagnostic outcome. The association between the MUCQuant+ index with questionnaire and symptom-based-diagnosis versus control subjects yielded a "good" outcome (AUC=0.81) for smokers, an "excellent" outcome for both CB and non-CF bronchiectasis (AUC=0.98 and AUC=1 respectively) (FIGS. 17A-17B).

The present invention provides a diagnostic and prognostic objective measurement of muco-obstructive lung diseases, comparable to blood sugar level for diagnosing diabetes or to serum cholesterol levels for predicting cardiovascular risk. Furthermore, the mucin score of the present invention should also assist in elucidating the underlying biological pathways involved in the pathogenesis of specific endotypes of muco-obstructive lung diseases, leading to more effective and personalized therapeutic agents.

In hypersecretory, muco-obstructive lung diseases such as COPD, asthma, CF, and non-CF bronchiectasis including PCD, and other hypersecretory diseases of the upper respiratory systems such as allergic rhinitis, different types of chronic sinusitis, the mechanism of the mucus obstruction is not known and there is no metric for these diseases to understand the pathogenesis for proper treatments. Therefore, it is of interest to adapt the mucin metric, MUCQuant and MUCQuant+, to understand the cause of mucus accumulation in the airways and to diagnose a diverse array of diseases characterized by mucus accumulation including CB, bronchiectasis, asthma spectrum (type 1 vs type 2), primary ciliary dyskinesia (PCD), cystic fibrosis (CF), and other chronic hypersecretory diseases of the upper airways such as allergic rhinitis and chronic sinusitis.

COPD:

Using airway mucus samples (induced/spontaneous sputum, mucus brushes and BAL samples) from a nationwide COPD study called SPIROMICS, we determined the MUCQuant and MUCQuant+ index of sputum samples from healthy control subjects, cigarette smokers (at risk population) with no COPD, or subjects with COPD, CB and/or emphysema. In addition, the index will be used to evaluate smokers with CB symptoms that have not yet developed CB and for the severity of airway obstruction.

Our preliminary data indicate that SPLUNC1 and FCGBP proteins are inversely correlated to each other in response to different inflammatory stimulus. With this, we are in the process of creating individual MUCQuant+ score for each subject to understand the disease progression and the severity of the bronchitis. Personalized MUCQuant and MUCQuant+ scores will be important for understanding how the epithelial response to chronic stimuli and the characteristics of mucus relate to disease severity and symptoms in these disorders. Eventually these personalized scores will be useful for detecting subjects at risk for COPD, and for developing new therapies for COPD. The present invention will also be helpful for identifying which subjects will benefit most from different treatments.

Asthma:

Asthma affects people of all ages and often starts during childhood. In the United States, more than 25 million people are known to have asthma. Asthma has a much broader spectrum than any other lung disease because of the complexity of the immunological response to different stimulus and not all asthma is developed in response to allergen sensitization. Therefore, determination of the pathways involved in these individual responses that leads to differing spectrum of asthmatic responses requires a personalized biological and objective marker such as that provided by the mucin metrics of the present invention. These tools will help to identify new and effective therapeutic targets for personalized therapies. Our preliminary data indicates that the MUCQ and especially MUCQ+ score is quite distinctive in asthma comparing to other bronchiectatic diseases (Table 12). Also, the mucin indices of the present invention may distinguish between type1 (mild) and type 2 (severe, IL13 type) asthma, the MUCQ+ score is ~18 fold increased in type 2 asthmatics than in type 1, more than 25 fold when compared to bronchitis and more than 1000 fold compared to healthy individuals (Table 12). Thus, the MUCQuant and MUCQuant+ scores may be personalized for each subject to understand the disease progression and the severity of the airway obstruction. Personalized MUCQuant and MUCQuant+ scores will be important in understanding the epithelial response to allergens and establishing how the characteristics of mucus relate to the asthma spectrum and airway remodeling. Eventually, these personalized scores should assist in the detection of people at risk for asthma, in discovery of new targets for new therapies and may be helpful in predicting those persons who will benefit most from different treatments.

Bronchiectasis:

Bronchiectasis generally results from an infection that permanently damages the airway walls, compromises the mucociliary clearance, and eventually results in with airway obstruction. Bronchiectasis is most commonly seen in genetic diseases such as CF and PCD, which are characterized by airway dehydration, persistent infection and inflammation.

Non-CF bronchiectasis is characterized by chronic production of sputum and chronic infection. Although the inflammation plays a role in the pathogenesis of non-CF bronchiectasis, the underlying pathways that lead to airway damage and mucus over production are not known. Our preliminary data indicated that although the sputum characteristics (mucoid vs fluid like) perceptions are similar in CB and non-CF bronchiectasis patients, mucin dynamics and mucin scores, especially the MUCQ+ score of the sputum from non-CF bronchiectasis are significantly different than the sputum from CB patients (FIG. 17A-17B), which suggest a different mechanism/pathway involved in the pathogenesis of these diseases.

Personalized MUCQuant and MUCQuant+ scores will be important for understanding the epithelial response to chronic damage, and how the characteristics of mucus relate to disease severity and symptoms. Eventually, personalized MUCQuant and MUCQuant+ scores will be useful for identifying pathways that activate mucin/mucus production and secretion, for factors that influence mucus obstruction, and for linking the types of mucin so as to provide new insights into effective treatments that enhance mucociliary clearance and airway function in bronchiectasis and other chronic airway diseases. Although, CF and PCD type bronchiectatic diseases have a known genetic basis, understanding the pathways causing the mucus hypersecretion and mucus obstruction via the personalized mucin indices of the present invention will be helpful in developing better treatments.

TABLE 1

Enrollment Criteria for SPIROMICS and Distribution of the SPIROMICS cohort, Mucin Concentration Study and MUC5B/AC Study by Strata (recruitment group)

| μM | Strata 1<br>Non-Smokers | Strata 2<br>Smokers No COPD | Strata 3<br>Mild/Moderate COPD | Strata 4<br>Severe COPD |
|---|---|---|---|---|
| Enrollment Criteria | | | | |
| Smoking Status | <1 pack-year | >20 pack-years | >20 pack-years | >20 pack-years |
| Bronchodilator Status for Assessing Lung Function | Pre-bronchodilator | Post-bronchodilator | Post-bronchodilator | Post-bronchodilator |
| FEV1/FVC Ratio criteria* | FEV1/FVC > .7 | FEV1/FVC > .7 | FEV1/FVC < .7 | FEV1/FVC < .7 |
| Other Lung Function Criteria)† | FVC > LLN | FVC > LLN | FEV1 > 50% pred. | FEV1 < 50% pred. |
| Distribution | | | | |
| Entire SPIROMICS Cohort¶ | N = 200 (6.8%) | N = 936 (31.7%) | N = 1199 (40.6%) | N = 434 (20.9%) |
| Mucin Concentration Study | N = 69 (7.5%) | N = 308 (33.6%) | N = 451 (49.2%) | N = 89 (9.7%) |
| MUC5B/AC Study | N = 19 (12.84%) | N = 42 (28.38%) | N = 59 (38.86%) | N = 28 (18.92%) |

*FEV1 denotes forced expiratory volume in one second, FVC denotes forced vital capacity.
†LLN denotes lower limit of normal.
¶Limited to the participants with complete clinical data available at the time of Mucin Study Closure (N = 2769).

TABLE 2

Distribution by recruitment groups (Strata) of 917 participants for the Mucin Concentration Study when sputum mucin concentrations were measured

| | Strata 1<br>Non-Smokers | Strata 2<br>Smokers No COPD | Strata 3<br>Mild/Moderate COPD | Strata 4<br>Severe COPD |
|---|---|---|---|---|
| N (%) | 69 (7.5%) | 308 (33.6%) | 451 (49.2%) | 89 (9.7%) |
| Age | 56.7 ± 10.4 | 60.3 ± 9.9 | 65.4 ± 8 | 66.5 ± 7.6 |
| Sex (Male, %) | 32 (46.4%) | 169 (54.9%) | 282 (62.5%) | 50 (56.2%) |
| Body Mass Index | 28.8 ± 5.1 | 29.2 ± 5.1 | 28.2 ± 5.1 | 27.1 ± 5 |
| Currently Smoking (YES, %) | 0 (0%) | 164 (53.2%) | 184 (40.8%) | 26 (29.2%) |
| Smoking Pack - years | 0 ± 0 | 42.7 ± 21 | 54.1 ± 28.1 | 51.2 ± 23.2 |
| Asthma Status (Current, %) | 0 | 30 (10.6%) | 72 (18.27%) | 11 (14.29%) |
| Asthma Diagnosed (Childhood, %) | 0 | 22 (8.0%) | 46 (12.50%) | 5 (7.04%) |
| FEV1/FVC (% predicted Post BD) | 103.8 ± 5.7 | 100.1 ± 6.4 | 77.2 ± 10.6 | 55.2 ± 5.7 |

*BD denotes bronchodilator
± denotes standard deviation

TABLE 3

Distribution by recruitment groups of 148 randomly selected participants for the MUC5B/AC study whose MUC5B and MUC5AC values were measured by mass spectroscopy

| | Strata 1<br>Non-Smokers | Strata 2<br>Smokers No COPD | Strata 3<br>Mild/Moderate COPD | Strata 4<br>Severe COPD |
|---|---|---|---|---|
| N (%) | 19 (12.84%) | 42 (28.38%) | 59 (38.86%) | 28 (18.92%) |
| Age | 59.16 ± 8.9 | 60.04 ± 9.7 | 64.22 ± 8.7 | 67.21 ± 6.9 |
| Sex (Male, %) | 9 (47.36%) | 20 (47.61%) | 42 (71.18%) | 16 (57.14%) |

TABLE 3-continued

Distribution by recruitment groups of 148 randomly selected participants for the MUC5B/AC study whose MUC5B and MUC5AC values were measured by mass spectroscopy

|  | Strata 1 Non-Smokers | Strata 2 Smokers No COPD | Strata 3 Mild/Moderate COPD | Strata 4 Severe COPD |
|---|---|---|---|---|
| Body Mass Index | 27.6 ± 4.7 | 28.2 ± 4.9 | 28.8 ± 5.5 | 27.9 ± 3.9 |
| White, % | 17 (89.47%) | 28 (66.66%) | 49 (83.05%) | 22 (78.57%) |
| Black, % | 0 | 12 (28.57%) | 8 (13.56%) | 3 (10.71%) |
| Other, % | 2 (10.52%) | 2 (4.76%) | 2 (3.89%) | 3 (10.71%) |
| Currently Smoking (YES, %) | 0 (0%) | 25 (59.52%) | 24 (40.67%) | 7 (25.00%) |
| Smoking Pack - years | 0 ± 0 | 40.17 ± 17.9 | 56.21 ± 27.77 | 54.42 ± 17.79 |
| Chronic Bronchitis Only, Yes (%) SGRQ | 0 (0%) | 20 (47.61%) | 19 (32.20%) | 3 (10.71%) |
| Emphysema Only, Yes (%) | 2 (10.52%) | 3 (7.14%) | 9 (15.25%) | 14 (50.00%) |
| Asthma Status (Current, %) | 0 | 6 (15.38%) | 10 (18.18%) | 4 (15.38%) |
| Asthma Diagnosed (Childhood, %) | 0 | 3 (8.33%) | 4 (8.16%) | 3 (12.00%) |
| Both Chronic Bronchitis (SGRQ) and Emphysema, Yes (%) | 0 (0%) | 5 (11.90%) | 16 (27.11%) | 10 (35.71%) |
| FEV1 (% predicted Post BD) | 100.62 ± 14.07 | 94.42 ± 12.51 | 76.82 ± 15.49 | 43.89 ± 4.16 |
| FVC (% predicted Post BD) | 95.19 ± 10.47 | 95.20 ± 13.34 | 99.83 ± 18.04 | 83.01 ± 14.92 |
| FEV1/FVC (% predicted Post BD) | 105.12 ± 5.29 | 100.83 ± 7.21 | 77.23 ± 11.02 | 54.15 ± 9.98 |

TABLE 4

Distribution by groups of 94 selected participants for the independent cohort

|  | Never Smoker Control | Current Smoker Control | Ever Smoker CB (+) |
|---|---|---|---|
| N | 30 | 28 | 36 |
| Age | 27.3 ± 6.1 | 29.5 ± 7.2 | 60.7 ± 9.1 |
| Gender (%) | 17/30 (57%) | 13/28 (46%) | 20/36 (56%) |
| Race (White, %) | 22/30 (73%) | 17/28 (61%) | 31/36 (86%) |
| Race (Black, %) | 4/30 (13%) | 8/28 (29%) | 5/36 (14%) |
| Smoking Status (Current, %) | 0/30 (0%) | 28/28 (100%) | 17/36 (47%) |
| Pack Year (# Participants who answered pack year questionnaire) | 0 ± 0 (14) | 7.2 ± 4.9 (11) | 44.1 ± 26.9 (36) |
| Mean Mucin Concentration | 1603.3 ± 1040.8 (30) | 1691.7 ± 827.4 (28) | 3867.7 ± 2296.6 (36) |
| FEV1% predicted * (number of participants who had available FEV1% data) | 96 ± 10.5 (22) | 96 ± 11.3 (24) | 59.1 ± 19.9 (35) |
| FVC % predicted * (number of participants who had FVC % data) | 98 ± 11 (22) | 95.6 ± 22.7 (24) | 80.1 ± 14.8 (35) |

* Pre-bronchodilators for Controls, Post-bronchodilators for CB+
± indicates standard deviation

TABLE 5

Detailed multiple regression analysis for phlegm and chronic bronchitis in 917 participants

|  | Model 1 | | | Model 2 | | | Model 3 |
|---|---|---|---|---|---|---|---|
| Explanatory Variable | OR | 95% CI | P-value | OR | 95% CI | P-value | OR |
| Multiple Regression for Phlegm | | | | | | | |
| Mucin Concentration (log) | 1.689 | [1.448, 1.97] | <.0001 | 1.579 | [1.339, 1.861] | <.0001 | 1.598 |
| BMI | | | | 1.03 | [1, 1.06] | 0.0481 | 1.022 |
| Age | | | | 1.018 | [0.999, 1.037] | 0.0662 | 1.021 |
| Smoking Status | | | | | | <.0001 | |
| Past vs None | | | | 5.469 | [2.097, 14.267] | | 5.196 |

TABLE 5-continued

Detailed multiple regression analysis for phlegm and chronic bronchitis in 917 participants

| Explanatory Variable | OR | 95% CI | P-value | OR |
|---|---|---|---|---|
| Current vs None | 18.084 | [6.952, 47.04] | | 19.186 |
| SEX | 0.774 | [0.576, 1.041] | 0.0905 | 0.703 |
| RACE† | | | 0.8822 | |
| American Indian vs White | 0.948 | [0.121, 7.411] | | 2.661 |
| Asian vs White | 1.47 | [0.381, 5.674] | | 1.072 |
| Mixed vs White | 0.699 | [0.259, 1.888] | | 0.419 |
| Black vs White | 0.878 | [0.59, 1.307] | | 0.744 |
| ETHNICITY Hispanic vs Non-Hispanic | 0.879 | [0.443, 1.748] | 0.7137 | 0.71 |
| GERD | | | | 1.226 |
| Asthma Status (Current vs No Asthma) | | | | 1.767 |
| Total Exacerbations Rate | | | | |

Multiple Regression for Chronic Bronchitis

| Explanatory Variable | OR | 95% CI | P-value | OR |
|---|---|---|---|---|
| Mucin Concentration (log) | 1.65 | [1.377, 1.978] | <.0001 | 1.609 | [1.323, 1.957] | <.0001 | 1.527 |
| BMI | | | | 1.008 | [0.975, 1.042] | 0.629 | 0.994 |
| AGE | | | | 0.992 | [0.971, 1.013] | 0.4499 | 0.999 |
| Smoking Status | | | | | | <.0001 | |
| Past vs None | | | | 5.027 | [1.177, 21.476] | | 3.394 |
| Current vs None | | | | 12.911 | [3.077, 54.174] | | 9.949 |
| SEX | | | | 1.131 | [0.802, 1.596] | 0.4822 | 1.053 |
| RACE | | | | | | 0.2398 | 1.66 |
| American Indian vs White | | | | 0.728 | [0.07, 7.571] | | |
| Asian vs White | | | | 1.67 | [0.389, 7.165] | | 1.796 |
| Mixed vs White | | | | 1.042 | [0.361, 3.01] | | 1.041 |
| Black vs White | | | | 0.59 | [0.367, 0.947] | | 0.51 |
| ETHNICITY Hispanic vs Non-Hispanic | | | | 1.11 | [0.507, 2.432] | 0.7936 | 0.837 |
| GERD | | | | | | | 1.398 |
| Asthma Status (Current vs No Asthma) | | | | | | | 2.635 |
| Total Exacerbations Rate | | | | | | | |

| | Model 3 | | Model 4 | | |
|---|---|---|---|---|---|
| Explanatory Variable | 95% CI | P-value | OR | 95% CI | P-value |

Multiple Regression for Phlegm

| Explanatory Variable | 95% CI | P-value | OR | 95% CI | P-value |
|---|---|---|---|---|---|
| Mucin Concentration (log) | [1.34, 1.907] | <.0001 | 1.515 | [1.264, 1.814] | <.0001 |
| BMI | [0.991, 1.054] | 0.1651 | 1.023 | [0.991, 1.055] | 0.1573 |
| Age | [1.001, 1.042] | 0.0355 | 1.022 | [1.002, 1.043] | 0.033 |
| Smoking Status | | <.0001 | | | <.0001 |
| Past vs None | [1.789, 15.092] | | 4.527 | [1.554, 13.194] | |
| Current vs None | [6.618, 55.623] | | 17.365 | [5.983, 50.4] | |
| SEX | [0.512, 0.966] | 0.0296 | 0.66 | [0.477, 0.915] | 0.0125 |
| RACE | | 0.3425 | | | 0.6437 |
| American Indian vs White | [0.21, 33.724] | | 1.733 | [0.088, 34.314] | |
| Asian vs White | [0.252, 4.56] | | 1.234 | [0.289, 5.281] | |
| Mixed vs White | [0.139, 1.26] | | 0.495 | [0.158, 1.556] | |
| Black vs White | [0.486, 1.139] | | 0.796 | [0.514, 1.233] | |
| ETHNICITY Hispanic vs Non-Hispanic | [0.332, 1.521] | 0.3783 | 0.701 | [0.32, 1.537] | 0.3752 |
| GERD | [0.875, 1.72] | 0.2368 | 1.146 | [0.809, 1.623] | 0.4432 |
| Asthma Status (Current vs No Asthma) | [1.107, 2.82] | 0.017 | 1.564 | [0.963, 2.541] | 0.0708 |
| Total Exacerbations Rate | | | 1.61 | [1.238, 2.093] | 0.0004 |

Multiple Regression for Chronic Bronchitis

| Explanatory Variable | 95% CI | P-value | OR | 95% CI | P-value |
|---|---|---|---|---|---|
| Mucin Concentration (log) | [1.24, 1.88] | <.0001 | 1.429 | [1.153, 1.772] | 0.0011 |
| BMI | [0.959, 1.03] | 0.7275 | 0.995 | [0.959, 1.032] | 0.7883 |
| AGE | [0.977, 1.022] | 0.9499 | 1.002 | [0.979, 1.025] | 0.8949 |
| Smoking Status | | <.0001 | | | <.0001 |
| Past vs None | [0.786, 14.666] | | 2.702 | [0.621, 11.757] | |
| Current vs None | [2.351, 42.1] | | 8.652 | [2.039, 36.701] | |
| SEX | [0.725, 1.529] | 0.785 | 0.926 | [0.63, 1.363] | 0.6977 |
| RACE | | 0.1056 | <0.001 | | 0.1855 |
| American Indian vs White | [0.132, 20.818] | | | [<0.001, >999] | |
| Asian vs White | [0.374, 8.625] | | 2.054 | [0.421, 10.03] | |
| Mixed vs White | [0.321, 3.369] | | 0.916 | [0.266, 3.159] | |
| Black vs White | [0.305, 0.853] | | 0.543 | [0.321, 0.919] | |
| ETHNICITY Hispanic vs Non-Hispanic | [0.344, 2.04] | 0.6956 | 0.956 | [0.381, 2.397] | 0.9233 |
| GERD | [0.945, 2.068] | 0.0936 | 1.233 | [0.822, 1.85] | 0.3112 |
| Asthma Status (Current vs No Asthma) | [1.62, 4.288] | <.0001 | 2.347 | [1.411, 3.903] | 0.001 |
| Total Exacerbations Rate | | | 1.77 | [1.37, 2.286] | <.0001 |

TABLE 6

Sensitivity analysis - comparison of different descriptive variables between the interquartile range (normal) and extreme (lower 25%; higher 25%) quartiles of mucin concentration in GOLD stage 0, 1, 2, 3

|  | LOW 25% Mucin < 946.925 N = 211 | NORMAL N = 423 | HIGH 25% Mucin ≥ 3314.133 N = 212 | P values |
|---|---|---|---|---|
| MUCIN CONCENTRATION (ug/mL) | 597.67 +/- 206.11 | 1859.59 +/- 633.83 | 6481.47 +/- 3794.36 |  |
| Phlegm Yes/Total (%) | 81/208 (28.9%) | 219/414 (52.9%) | 132/207 (63.8%) | <0.0001 |
| Consistency of sputum (mucoid) | 44/186 (23.7%) | 191/353 (54.1%) | 127/173 (73.4%) | <0.0001 |
| Presence of plugs   Moderate | 55/173 (31.8%) | 113/329 (34.4%) | 56/145 (38.6%) | 0.0144 |
| Numerous | 18/173 (10.4%) | 113/329 (18.9%) | 30/145 (20.7%) |  |
| CB*   SGRQ CB | 68/206 (33.01%) | 190/410 (46.34%) | 123/202 (60.89%) | <0.0001 |
| Classic CB | 29/203 (14.29%) | 103/409 (25.18%) | 66/203 (32.51%) | <0.0001 |
| FEV1 (% predicted post BD)* | 84.24 +/- 21.7 | 80.16 +/- 20.97 | 74.17 +/- 20.12 | <0.0001 |
| FEV1/FVC (% predicted post BD)* | 86.46 +/- | 83.38 +/- 16.63 | 80.05 +/- 17.49 | <0.0001 |
| Total rate of exacerbations | 0.27 +/- | 0.37 +/- 0.8 | 0.47 +/- 0.96 | <0.0001 |
| Exacerbations requiring HCU | 0.23 +/- | 0.34 +/- 0.75 | 0.43 +/- 0.94 | <0.0001 |
| Asthma: any diagnosis | 33/202 (16.34%) | 75/404 (18.56%) | 53/194 (27.32%) | <0.0001 |

*BD denotes bronchodilator.

TABLE 7

Subgroup analysis of mucin concentration in chronic bronchitis negative (CB- by Classic questionnaire) group in the bottom (LOW) versus top (HIGH) 25% total sputum mucin concentration levels in ever-smokers (GOLD stage 0, 1, 2, 3)

|  | LOW CB- N = 174 | HIGH CB- N = 137 | P-value HIGH CB- vs. LOW CB- |
|---|---|---|---|
| Mucin Concentration (ug/mL) | 571 +/- 198 | 5890 +/- 3374 |  |
| Phlegm Yes/Total (%) | 52/171 (30.4%) | 66/132 (50%) | 0.0005 |
| Consistency of sputum (mucoid) | 37/156 (23.7%) | 84/115 (73%) | <0.0001 |
| Number of plugs   Moderate | 44/140 (31.4%) | 36/90 (40%) | 0.0039 |
| Numerous | 13/140 (9.3%) | 19/90 (21.1%) |  |
| FEV1% (% predicted post BD) | 85.44 +/- 21.95 | 76.86 +/- 20.68 | 0.0005 |
| FEV1/FVC % (% predicted post BD | 87.47 +/- 16.37 | 81.94 +/- 16.89 | 0.0038 |

TABLE 8

Characteristics of Mucin Concentration Study Compared to Entire SPIROMICS Cohort at Baseline.

| | Mucin Concentration Study | | | | | | |
|---|---|---|---|---|---|---|---|
| Variable | Never Smokers FEV1/FVO > .7 | GOLD Stage 0 Ever Smokers No COPD FEV1/FVO > .7 | GOLD Stage 1 Mild COPD *FEV1/FVC < .7 and FEV1 ≥ 80% predicted | GOLD Stage 2 Moderate COPD *FEV1/FVC < 0.7 and 50% ≤ FEV1 < 80% predicted | GOLD Stage 3 Severe COPD *FEV1/FVC < 0.70 and 30% ≤ FEV1 < 50% predicted | Total | SPIROMICS COHORT |
| N | 69 | 303 | 165 | 293 | 85 | 917 | 2770 |
| Age | 56.7 ± 10.5 | 60.2 ± 9.9 | 66.4 ± 8.4 | 64.8 ± 7.8 | 66.8 ± 8.4 | 63.1 ± 9.4 | 63 ± 9.3 |
| Sex (Male, %) | 32 (46.4%) | 167 (55.1%) | 109 (66.1%) | 177 (60.4%) | 46 (54.1%) | 533 (58.1%) | 1449 (52.3%) |
| BMI | 28.8 ± 5.1 | 29.2 ± 5.1 | 28.1 ± 4.8 | 28.3 ± 5.3 | 27.2 ± 4.6 | 28.5 ± 5.1 | 28 ± 5.2 |
| White, % | 45 (65.2%) | 197 (65%) | 134 (81.2%) | 246 (84%) | 69 (81.2%) | 692 (75.5%) | 2102 (75.9%) |
| Black, % | 19 (27.5%) | 86 (28.4%) | 25 (15.2%) | 37 (12.6%) | 10 (11.8%) | 178 (19.4%) | 540 (19.5%) |
| Current Smoker (YES, %) | 0 | 161 (53.1%) | 58 (35.2%) | 130 (44.4%) | 24 (28.2%) | 374 (40.8%) | 1055 (38.1%) |

TABLE 8-continued

Characteristics of Mucin Concentration Study Compared to Entire SPIROMICS Cohort at Baseline.

| | Mucin Concentration Study | | | | | | |
|---|---|---|---|---|---|---|---|
| Variable | Never Smokers FEV1/FVO > .7 | GOLD Stage 0 Ever Smokers No COPD FEV1/FVO > .7 | GOLD Stage 1 Mild COPD *FEV1/FVC < .7 and FEV1 ≥ 80% predicted | GOLD Stage 2 Moderate COPD *FEV1/FVC < 0.7 and 50% ≤ FEV1 < 80% predicted | GOLD Stage 3 Severe COPD *FEV1/FVC < 0.70 and 30% ≤ FEV1 < 50% predicted | Total | SPIROMICS COHORT |
| Smoking Pack-years | 0 | 42.6 ± 21 | 50.5 ± 24.7 | 55.9 ± 29.6 | 51.6 ± 23.2 | 45.9 ± 28 | 45.5 ± 29 |
| Chronic Bronchitis (%) | 2 (2.9%) | 57 (18.8%) | 30 (18.2%) | 89 (30.4%) | 22 (25.9%) | 201 (21.9%) | 549 (19.8%) |
| Emphysema (%) | 3 (4.3%) | 24 (7.9%) | 45 (27.3%) | 123 (42%) | 62 (72.9%) | 259 (28.2%) | 875 (31.6%) |
| Asthma Status (Current, %) | 0 | 29 (10.39%) | 26 (18.06%) | 47 (18.50%) | 11 (14.67%) | 113 (13.80%) | 401 (15.20%) |
| Asthma Diagnosed (Childhood, %) | 0 | 21 (7.75%) | 18 (13.24%) | 30 (12.66%) | 4 (5.88%) | 73 (9.37%) | 245 (9.87%) |
| FEV1 (% of predicted value) | 101.5 ± 12.1 | 96.7 ± 14.3 | 91.7 ± 10.3 | 65.9 ± 8.3 | 43.2 ± 4.1 | 81.2 ± 21.5 | 78.4 ± 23.9 |
| FVC (% of predicted value) | 97.3 ± 10.4 | 96.2 ± 14.1 | 109.2 ± 13.5 | 90.5 ± 12.7 | 80.5 ± 15.4 | 95.3 ± 15.6 | 93.7 ± 16.4 |

*Plus-minus values are means ± SD.
FEV1 denotes forced expiratory volume in one second; FVC denotes forced vital capacity. Body-mass index (BMI) is the weight in kilograms divided by the square of the height in meters. Current smoking status indicates smoking referenced to self-report of smoking for the three months prior to baseline visit. Smoking pack years were calculated by multiplying the participant-reported number of packs of cigarettes smoked per day by the number of years the person reported smoking. Chronic bronchitis (CB) diagnosed based on Classical definition of CB defined by the Medical Research Council (MRC) as chronic cough and sputum production for 3 months a year for 2 consecutive years. Emphysema was diagnosed from volumetric multidetector-row computed tomography (MDCT) of the lungs using an emphysema index (EI) of percent voxels in the lung field < −950 HU. Normalized equations from the MESA study were used to establish emphysema (Supplementary Appendix); if the EI is ≥ upper limit of normal for a given participant, they were categorized as emphysema positive, otherwise they are emphysema negative.

TABLE 9

Mucin concentrations, smoking status and disease severity of COPD as indexed by the spirometric evaluation classification.

| | Healthy N = 73 | Smokers with no COPD N = 279 | Mild and Moderate COPD N = 389 | Severe COPD N = 84 |
|---|---|---|---|---|
| Mucin Concentration (mean) ug/ml | 1560 | 2042 | 2610 | 2772 |
| Std Error of Mean | 195 | 139 | 141 | 357 |

TABLE 10

Concentrations of MUC5AC and MUC5B, and the ratio of MUC5AC/MUC5B in sputum samples from sputum from healthy subjects as compared to smokers with no COPD and smokers with mild/moderate or severe COPD.

| | Healthy N = 17 | Smokers with no COPD N = 42 | Mild and Moderate COPD N = 60 | Severe COPD N = 30 |
|---|---|---|---|---|
| MUC5AC picomol/ml +/− SEM | 13 | 40 | 80 | 108 |
| MUC5B picomol/ml +/− SEM | 110 | 173 | 184 | 314 |
| MUC5AC/B | 0.068 | 0.27 | 0.50 | 0.32 |

TABLE 11

KMQant index calculated for healthy subjects (never smokers) as compared to smokers without COPD and subjects diagnosed with varying degrees of COPD and asthma.

| | Healthy N = 17 | Smokers with no COPD N = 42 | Mild and Moderate COPD N = 60 | Severe COPD N = 30 | Asthma (Mild/moderate) N = 10 | Asthma (Severe) N = 5 |
|---|---|---|---|---|---|---|
| Kesimer Mucin index (MUCQ) | 1.2 (+/−0.5) | 10.2 (+/−3) | 21.4 (+/−5) | 10.7 (+/−3) | 20 (+/−8) | 90 (+/−10) |

TABLE 12

MUCQuant and MUCQuant plus score in health and mucoobstructive lung diseases.

| | Healthy N = 17 | Smokers (No CB) N = 42 | Chronic Bronchitis N = 51 | Bronchiectasis N = 14 | Asthma (mild) N = 5 | PCD N = 12 | Asthma (severe) N = 5 |
|---|---|---|---|---|---|---|---|
| Kesimer Mucin index (MUCQ) (mean +/− SEM) | 1.2 +/− 0.6 | 10 +/− 3.1 | 17 +/− 3.3 | 18 +/− 2.7 | 20 +/− 1.7 | 50 +/− 2.2 | 90 +/− 3.7 |
| Kesimer Mucin plus index (MUCQ plus) (mean +/− SEM) | 0.28 +/− 0.1 | 4.3 +/− 1.2 | 85 +/− 1.6 | 180 +/− 18 | 100* | 250 +/− 20 | 1800* |

MUCQuant: [Mucin] × ([MUC5AC] ÷ [MUC5B]) ÷ 100
MUCQuant plus: [Mucin] × ([MUC5AC] ÷ [MUC5B]) ÷ 100 × (FCGBP ÷ SPLUNC1)
*data obtained from human primary airway epithelial cell culture (HTBE) secretions after challenged with a type 2 cytokine (IL13).

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of treating a subject comprising:
   diagnosing or identifying a risk of developing chronic bronchitis (CB) in the subject, comprising:
   measuring an amount of each of (a) mucin, (b) mucin 5AC (MUC5AC) and (c) mucin 5B(MUC5B) in a sputum sample from the subject;
   calculating a ratio of the measured amount of MUC5AC to the measured amount of MUC5B;
   calculating a Kesimer MUCQuant index (KMQuant index) by multiplying the ratio by the measured amount of mucin to provide a product and dividing the product by 100 mucin×(MUC5AC÷MUC5B))÷100);
   diagnosing the subject as having CB or identifying the subject as being at risk of developing CB when the KMQuant index calculated for the sputum sample from the subject is increased as compared to a KMQuant index calculated for a control sputum sample; and
   treating the subject diagnosed as having CB or identified as having an increased risk of developing CB, wherein the treating comprises administering a therapeutically effective amount of an osmotic agent for airway surface hydration, an epithelial sodium channel (ENaC) blocker, an inhibitor of mucin secretion, an inhibitor of mucin production, a cystic fibrosis transmembrane regulator (CFTR) corrector, a CFTR potentiator, or any combination thereof.

2. The method of claim 1, wherein the subject diagnosed as having CB or identified as being at risk of developing CB has a KMQuant index that is increased by about 5-fold to about 10-fold over the KMQuant index calculated for the control sputum sample.

3. The method of claim 1, further comprising
   measuring an amount of each of an IgGFc-binding protein (FCGBP) and a bactericidal/permeability-increasing fold-containing family member A1 (BPIFA1 (or SPLUNC1)) present in the sputum sample from the subject;
   calculating a ratio of the measured amount of FCGBP to the measured amount of SPLUNC1; and
   calculating a KMQuant plus (+) index (MUCQuant+ index) by multiplying the ratio of the measured amount of FCGBP to the measured amount of SPLUNC1 by the KMQuant index ([mucin]×([MUC5AC]÷[MUC5B])÷100×(FCGBP÷SPLUNC1)), wherein the subject is diagnosed as having CB has a KMQuant+ index that is increased by about 250-fold to about 350-fold as compared to a KMQuant+index calculated for the control sputum sample or the subject is identified as being at risk of developing CB has a KMQuant+ index that is increased by about 10-fold to about 20-fold over a KMQuant+index calculated for the control sputum sample.

4. The method of claim 1, wherein measuring the amount of mucin comprises measuring all gel forming mucins present in the sputum sample.

5. The method of claim 1, wherein measuring mucin comprises measuring the amount of mucin 5B (MUC5B) and mucin 5AC (MUC5AC).

6. The method of claim 1, wherein the subject is a current or a past smoker.

7. A method for diagnosing and treating an exacerbation of chronic obstructive pulmonary disease (COPD) in a subject diagnosed with COPD, comprising:
   a) measuring an amount of each of (i) mucin, (ii) mucin 5AC (MUC5AC) and (iii) mucin 5B(MUC5B) in a first sputum sample taken from the subject at a first time point;
   b) calculating a first ratio of the measured amount of MUC5AC to the measured amount of MUC5B from the first sputum sample;
   c) calculating a first KMQuant index for the first sputum sample by multiplying the first ratio by the measured amount of mucin from the first sputum sample to provide a product and dividing the product by 100;
   d) measuring an amount of each of (i) mucin, (ii) MUC5AC and (iii) MUC5B in a second sputum sample taken from the subject at a time point subsequent to the first time point;
   e) calculating a second ratio of the measured amount of MUC5AC to the measured amount of MUC5B from the second sputum sample;
   f) calculating a second KMQuant index for the second sputum sample by multiplying the second ratio by the measured amount of mucin from the second sputum sample to provide a product and dividing the product by 100;
   g) comparing the first KMQuant index calculated for the first sample (c) to the second KMQuant index calculated for the second sputum sample (f), wherein an increase in the KMQuant index calculated for the second sputum sample as compared to the KMQuant index calculated for the first sputum diagnoses an exacerbation of COPD in the subject; and treating the subject diagnosed as having an exacerbation of COPD, wherein the treating comprises administering a therapeutically effective amount of an osmotic agent for airway surface hydration, an epithelial sodium channel (ENaC) blocker, an inhibitor of mucin secretion, an inhibitor of mucin, production, a cystic fibrosis transmembrane regulator (CFTR) corrector, a CFTR potentiator, or any combination thereof.

8. The method of claim 7, further comprising
h) measuring an amount of each of an IgGFc-binding protein (FCGBP) and a bactericidal/permeability-increasing fold-containing family member A1 (BPIFA1 (or SPLUNC1)) present in the first sputum sample from the subject;
i) calculating a ratio of the measured amount of FCGBP to the measured amount of SPLUNC1 in the first sputum sample;
j) calculating a KMQuant plus (+) index for the first sputum sample by multiplying the ratio of the measured amount of FCGBP to the measured amount of SPLUNC1 by the KMQuant index,
k) measuring the amount of each of an IgGFc-binding protein (FCGBP) and a bactericidal/permeability-increasing fold-containing family member A1 (BPIFA1 (or SPLUNC1)) present in the second sputum sample from the subject;
l) calculating a ratio of the measured amount of FCGBP to the measured amount of SPLUNC1 in the second sputum sample;
m) calculating a KMQuant+index for the second sputum sample by multiplying the ratio of the measured amount of FCGBP to the measured amount of SPLUNC1 by the KMQuant index+; and
n) comparing the KMQuant+index calculated for the first sample (j) to the KMQuant+index calculated for the second sputum sample (m), wherein an increase in the KMQuan+index calculated for the second sputum sample as compared to the KMQuant+index calculated for the first sputum diagnoses an exacerbation of COPD in the subject.

9. The method of claim 7, wherein measuring the amount of mucin comprises measuring all gel forming mucins present in the sputum sample.

10. The method of claim 7, wherein measuring mucin comprises measuring the amount of mucin 5B (MUC5B) and mucin 5AC (MUC5AC).

11. The method of claim 7, wherein the subject is a current or a past smoker.

* * * * *

UNITED STATES PATENT AND TRADEMARK OFFICE
CERTIFICATE OF CORRECTION

PATENT NO. : 12,078,640 B2
APPLICATION NO. : 16/609282
DATED : September 3, 2024
INVENTOR(S) : Mehmet Kesimer It is certified that error appears in the above-identified patent and that said Letters Patent is hereby corrected as shown below:

On the Title Page

Item (56) References Cited, PUBLICATIONS, Right Column, 6th Reference cited:
Please correct "Rademacher et al. "Bronchlectasis-Diagnosis and Treatment" Deutsches Aerzteblatt Online, 108(48):809-816 (2011)." to read --Rademacher et al. "Bronchiectasis-Diagnosis and Treatment" Deutsches Aerzteblatt Online, 108(48):809-815 (2011).--

Item (57) ABSTRACT, Line 17: Please correct "p monitoring" to read --monitoring--

In the Specification

Column 13, Line 26: Please insert a paragraph break between "-0.0099" and "FIGS. 15A-15C"

Column 20, Line 8: Please correct "3000 Ag/ml" to read --3000 µg/ml--

Column 20, Line 53: Please correct "MUCSB;" to read --MUC5B;--

Column 31, Line 65: Please correct "100 mx2 cm," to read --100 µm x 2 cm,--

Column 32, Line 2: Please correct "75 Cpmx15 cm," to read --75 µm x 15 cm,--

Column 37, Line 43: Please correct "MUCSB" to read --MUC5B--

Column 40, Line 61: Please correct "type$^2$" to read --type2--

Column 41, Line 12: Please correct "+[MUC5B]) +" to read --÷[MUC5B]) ÷--

Column 49, TABLE 8, under Mucin Concentration Study, 2$^{nd}$ column., Line 3: Please correct "FEV1/FVO > .7" to read --FEV1/FVC>.7--

Signed and Sealed this
Tenth Day of December, 2024

Katherine Kelly Vidal
*Director of the United States Patent and Trademark Office*

Column 49, TABLE 8, under Mucin Concentration Study, 3rd column., Line 5: Please correct "FEV1/FVO > .7" to read --FEV1/FVC>.7--

Column 51, TABLE 8-continued, under Mucin Concentration Study, 2nd column., Line 3: Please correct "FEV1/FVO > .7" to read --FEV1/FVC>.7--

Column 51, TABLE 8-continued, under Mucin Concentration Study, 3rd column., Line 5: Please correct "FEV1/FVO > .7" to read --FEV1/FVC>.7--